(12) United States Patent
Wang et al.

(10) Patent No.: US 12,293,823 B2
(45) Date of Patent: May 6, 2025

(54) HEALTH ADMINISTRATION METHOD, APPARATUS, AND SYSTEM, AND DATA COLLECTION APPARATUS

(71) Applicants: BEIJING BOE HEALTH TECHNOLOGY CO., LTD., Beijing (CN); BOE TECHNOLOGY GROUP CO., LTD., Beijing (CN)

(72) Inventors: Zhou Wang, Beijing (CN); Yang Peng, Beijing (CN); Tongbo Wang, Beijing (CN); Zigang Liu, Beijing (CN); Feng Qi, Beijing (CN); Guilong Yang, Beijing (CN); Yuan Gao, Beijing (CN); Yang Han, Beijing (CN); Haiyun Cui, Beijing (CN)

(73) Assignees: BEIJING BOE HEALTH TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 554 days.

(21) Appl. No.: 17/419,459

(22) PCT Filed: Nov. 25, 2020

(86) PCT No.: PCT/CN2020/131512
§ 371 (c)(1),
(2) Date: Jun. 29, 2021

(87) PCT Pub. No.: WO2021/104310
PCT Pub. Date: Jun. 3, 2021

(65) Prior Publication Data
US 2022/0076814 A1    Mar. 10, 2022

(30) Foreign Application Priority Data

Nov. 25, 2019  (CN) .......................... 201911168012.4
Jun. 9, 2020   (CN) .......................... 202010526828.6

(51) Int. Cl.
*G16H 40/20*   (2018.01)
*G06F 16/903*  (2019.01)
(Continued)

(52) U.S. Cl.
CPC ....... *G16H 40/20* (2018.01); *G06F 16/90335* (2019.01); *G16H 15/00* (2018.01);
(Continued)

(58) Field of Classification Search
CPC .............................. G16H 40/20; G16H 40/67
See application file for complete search history.

(56) References Cited

U.S. PATENT DOCUMENTS

| 8,868,681 B2 * | 10/2014 | Xu ........................ G16H 10/60 709/217 |
| 2008/0058615 A1 | 3/2008 | Clapp et al. |

(Continued)

FOREIGN PATENT DOCUMENTS

| CN | 101926675 A | 12/2010 |
| CN | 104715128 A | 6/2015 |

(Continued)

OTHER PUBLICATIONS

Extended European Search Report from European Patent Application No. 20892331.8 dated Jan. 2, 2023.

(Continued)

*Primary Examiner* — Jay M. Patel
(74) *Attorney, Agent, or Firm* — Dilworth & Barrese, LLP.; Michael J. Musella, Esq.

(57) ABSTRACT

A health administration method, a health administration apparatus, a health administration system, and a data collection apparatus are provided. The health administration method involves a plurality of objects and a plurality of devices, and includes: generating a device usage record of at least one object based at least on identity information of the (Continued)

at least one object among the plurality of objects and data generated by a device used by the at least one object (S10), and providing the device usage record of the at least one object to a memory associated with a health administration apparatus (S20). The health administration method, the health administration apparatus, the health administration system, and the data collection apparatus can improve work efficiency of medical workers.

19 Claims, 36 Drawing Sheets

(51) Int. Cl.
    *G16H 10/20*     (2018.01)
    *G16H 10/60*     (2018.01)
    *G16H 15/00*     (2018.01)
    *G16H 40/67*     (2018.01)
    *G06K 7/14*     (2006.01)
    *G06K 19/06*     (2006.01)

(52) U.S. Cl.
    CPC ........... *G16H 40/67* (2018.01); *G06K 7/1413* (2013.01); *G06K 19/06028* (2013.01); *G16H 10/20* (2018.01); *G16H 10/60* (2018.01)

(56) References Cited

U.S. PATENT DOCUMENTS

| | | | | |
|---|---|---|---|---|
| 2018/0096104 A1* | 4/2018 | Maley | ................... | G16H 40/67 |
| 2018/0295186 A1* | 10/2018 | Schlapfer | ................ | H04L 67/02 |
| 2018/0365383 A1* | 12/2018 | Bates | ..................... | G16H 50/20 |
| 2019/0058764 A1* | 2/2019 | Cai | ......................... | H04L 67/12 |
| 2019/0392930 A1* | 12/2019 | Dyell | .................... | G16H 40/63 |

FOREIGN PATENT DOCUMENTS

| | | |
|---|---|---|
| CN | 105653856 A | 6/2016 |
| CN | 106156454 A | 11/2016 |
| CN | 108010562 A | 5/2018 |
| JP | 2009519549 A | 5/2009 |
| JP | 2009289067 A | 12/2009 |
| JP | 2013156919 A | 8/2013 |
| JP | 2015008913 A | 1/2015 |
| JP | 2018084862 A | 5/2018 |

OTHER PUBLICATIONS

Japanese Office Action from Japanese Patent Application No. 2022-506398 mailed Jan. 7, 2025.

* cited by examiner

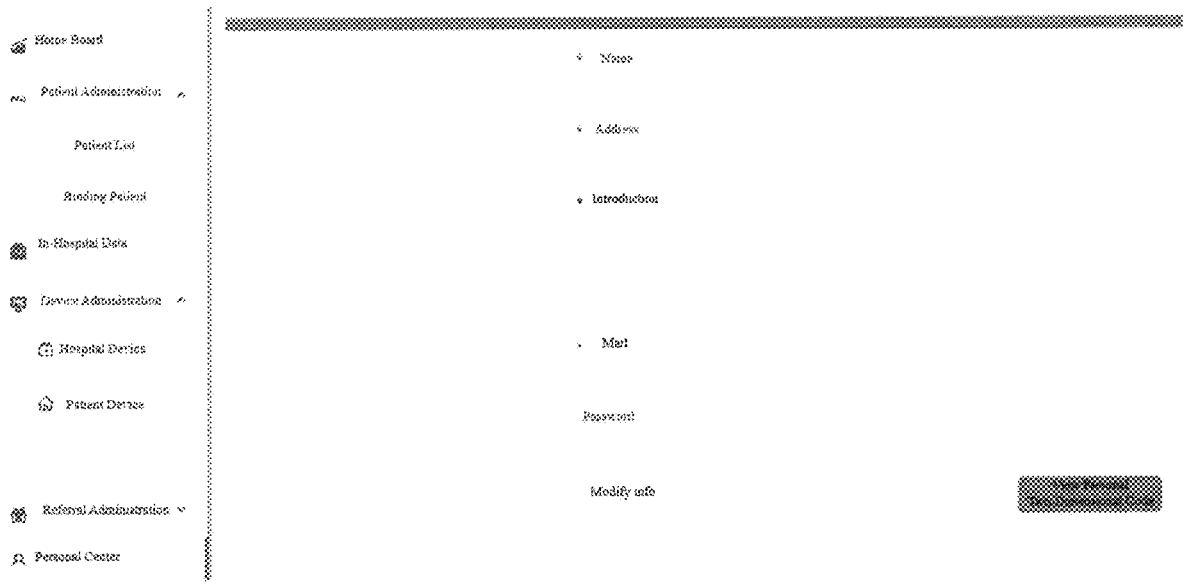
FIG. 3C
FIG. 3D
FIG. 3E

9: 17 pm

*Please fill in following information if use for the first time*

Name      Please enter your name

Identity Card NO.    Please enter your Identity Card NO.

Phone number     181xxxx1581

Age      Please enter your age

Please enter SMS verification code    Send verification code

Gender      Select

Disease type      Select

Height    Please enter height (cm)    cm

Weight    Please enter weight (kg)    kg

Register

FIG. 3H

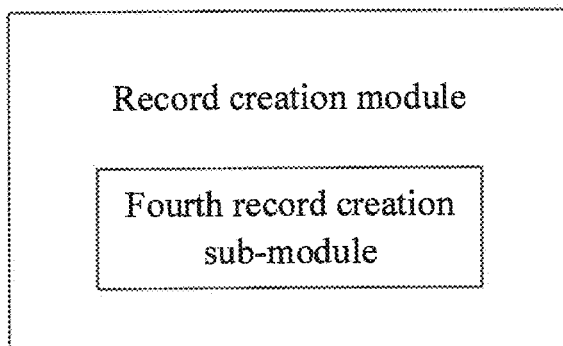
FIG. 7
```
┌─────────────────────────────────────────┐
│         Record creation module          │
│   ┌─────────────────────────────────┐   │
│   │    Fourth record creation       │   │
│   │         sub-module              │   │
│   └─────────────────────────────────┘   │
└─────────────────────────────────────────┘
```
FIG. 8
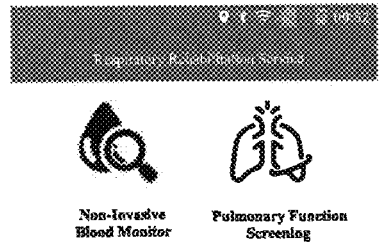
FIG. 9A

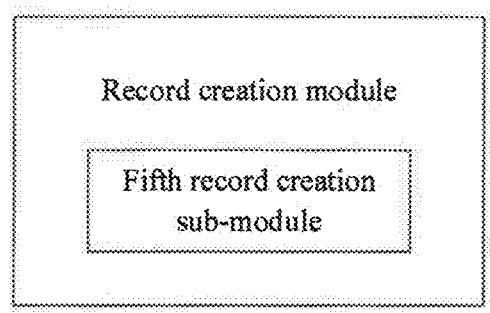
FIG. 12F
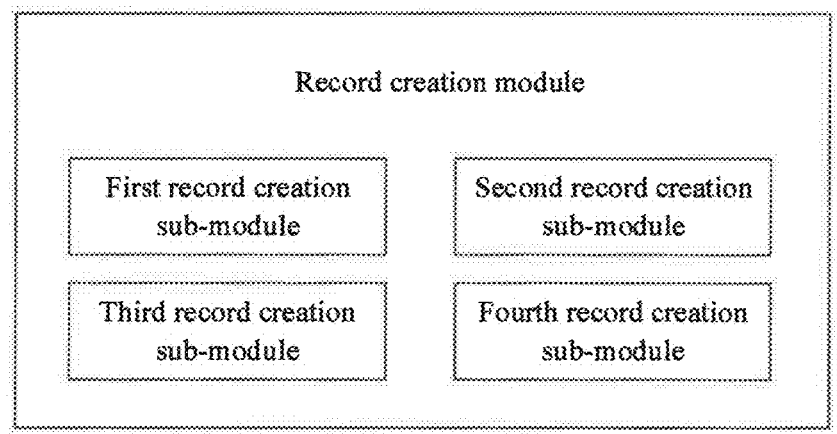
FIG. 13
FIG. 14

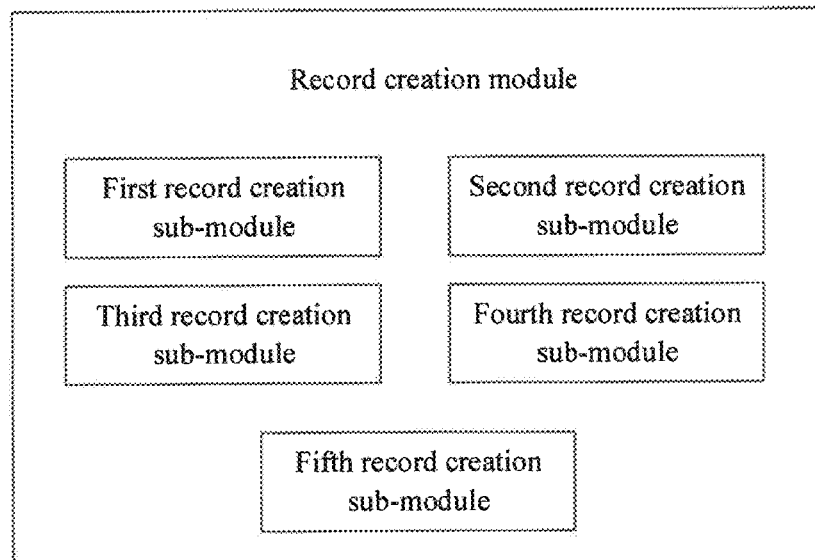
FIG. 15
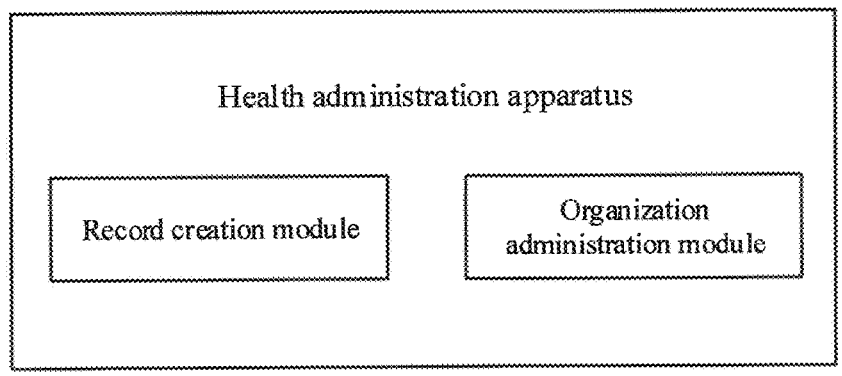
FIG. 16
FIG. 17

| Internal Serial No. | Referring Doctor | Referred-to Doctor | Patient Name | Patient Identity No. | Referral Status | Operation |
|---|---|---|---|---|---|---|
| 18 | BOE Organization Administrator | Qi Feng | Wang Yongbo 222 | 000004********1234 | Referral completed | |
| 17 | Liu Zigang | Qi Feng | Wang Yongbo 222 | 000004********1234 | Referral completed | |

HEALTH ADMINISTRATION METHOD, APPARATUS, AND SYSTEM, AND DATA COLLECTION APPARATUS

CROSS-REFERENCE TO RELATED APPLICATIONS

The present patent application claims priority of Chinese Patent Application No. 201911168012.4 filed on Nov. 25, 2019, and Chinese Patent Application No. 202010526828.6 filed on Jun. 9, 2020, the disclosure of which is incorporated herein by reference in its entirety as part of the present disclosure for all purposes.

TECHNICAL FIELD

Embodiments of the present disclosure relate to a health administration method, a health administration apparatus, a health administration system, and a data collection apparatus.

BACKGROUND

With economic development and improvement of living standards, more and more people suffer from chronic disease of varying degrees. Common chronic disease (or chronic non-communicable disease) mainly includes cardiovascular and cerebrovascular disease, cancer, diabetes, and chronic respiratory disease, etc.; and cardiovascular and cerebrovascular disease includes hypertension, stroke and coronary heart disease, etc. Data shows that there are more and more Chinese citizens suffering from chronic disease such as hypertension, diabetes, and dyslipidemia, etc. Data shows that one of the causes of the chronic disease is an unhealthy lifestyle. For example, unhealthy lifestyles include irrational diet, insufficient exercise, tobacco use, and excessive alcohol intake, etc.

A two-way referral system is an important measure taken by China to promote rational allocation of medical resources and solve the current problems of "difficult and expensive medical care" of the people, in which, on the one hand, due to limitations of medical measurement devices and techniques in subordinate hospitals (e.g., basic-level hospitals or community hospitals), patients with urgent or critical illness conditions in the subordinate hospitals may be transferred to superior hospitals (e.g., urban general hospitals) for treatment; on the other hand, patients with mild illness conditions in the superior hospitals (e.g., patients with common disease, patients diagnosed and treated for frequently-occurring illness, patients undergoing post-illness recovery treatment and nursing care, etc.) may be encouraged to transfer to the subordinate hospitals to make full use of service functions and network resources of the subordinate hospitals, so that medical resources at respective levels of hospitals can be effectively integrated and efficiently utilized, to avoid idleness and waste of medical resources.

SUMMARY

At least one embodiment of the present disclosure provides a health administration method, which involves a plurality of objects and a plurality of devices and includes: generating a device usage record of at least one object based at least on identity information of the at least one object among the plurality of objects and data generated by a device used by the at least one object, and providing the device usage record of the at least one object to a memory associated with a health administration apparatus.

For example, in at least one example of the health administration method, the generating the device usage record of the at least one object based at least on the identity information of the at least one object among the plurality of objects and the data generated by the device used by the at least one object, comprises: acquiring a first identification code of a current object among the plurality of objects and an identification code of a first current device, the first current device being a device that has been used by the current object; using the identification code of the first current device to query the memory associated with the health administration apparatus, to acquire latest device-related data originating from the first current device and transferred to the memory; using the first identification code of the current object to query the memory, to acquire identity information of the current object; and associating the identity information of the current object with the latest device-related data to generate the device usage record of the current object.

For example, in at least one example of the health administration method, the acquiring the first identification code of the current object among the plurality of objects and the identification code of the first current device comprises: acquiring the first identification code of the current object and the identification code of the first current device from an object service module of a terminal for the current object.

For example, in at least one example of the health administration method, the health administration method further comprises: generating a barcode of the first current device based on the identification code of the first current device.

For example, in at least one example of the health administration method, the health administration method further comprises: using the object service module to acquire the identification code of the first current device obtained by a barcode scanner scanning the barcode of the first current device.

For example, in at least one example of the health administration method, the health administration method further comprises: making the first current device allow device-related data generated by the first current device to be transferred to the memory via a third-party platform.

For example, in at least one example of the health administration method, the generating the device usage record of the at least one object based at least on the identity information of the at least one object among the plurality of objects and the data generated by the device used by the at least one object, comprises: acquiring a first identification code of a current object among the plurality of objects and an identification code of a second current device, the second current device being a device to be used by the current object; using the first identification code of the current object to query the memory associated with the health administration apparatus, to acquire identity information of the current object and to create a correspondence relationship between the identity information of the current object and the second current device; and in a case where a data receiver associated with the health administration apparatus receives device-related data originating from the second current device, associating the identity information of the current object with the device-related data to generate a device usage record of the current object.

For example, in at least one example of the health administration method, the acquiring the first identification code of the current object among the plurality of objects and the identification code of the second current device, comprises: acquiring the first identification code of the current object and the identification code of the second current device from an object service module of a terminal for the current object.

For example, in at least one example of the health administration method, the health administration method further comprises: generating a barcode of the second current device based on the identification code of the second current device.

For example, in at least one example of the health administration method, the health administration method further comprises: using the object service module to acquire the identification code of the second current device obtained by a barcode scanner scanning the barcode of the second current device; and making the second current device allow the device-related data generated by the second current device to be transferred to the data receiver associated with the health administration apparatus via a Bluetooth gateway.

For example, in at least one example of the health administration method, the generating the device usage record of the at least one object based at least on the identity information of the at least one object among the plurality of objects and the data generated by the device used by the at least one object, comprises: providing unassociated data of at least one device of the plurality of devices, the unassociated data being configured to be displayed in a terminal, where a first individual service module is located, for an individual; receiving, from the first individual service module, a second identification code of an object corresponding to the unassociated data; and associating the object corresponding to the unassociated data with the unassociated data, to generate a device usage record of the object corresponding to the unassociated data.

For example, in at least one example of the health administration method, the associating the object corresponding to the unassociated data with the unassociated data comprises: using the second identification code of the object corresponding to the unassociated data to query the memory associated with the health administration apparatus, to acquire identity information of the object corresponding to the unassociated data; and associating the identity information of the object corresponding to the unassociated data with the unassociated data.

For example, in at least one example of the health administration method, the generating the device usage record of the at least one object based at least on the identity information of the at least one object among the plurality of objects and the data generated by the device used by the at least one object, comprises: receiving identity information of a current object among the plurality of objects and device-related data generated by a third current device and associated with the identity information of the current object, the third current device being a device that has been used by the current object; and generating the device usage record of the current object based at least on the identity information of the current object and the device-related data generated by the third current device and associated with the identity information of the current object.

For example, in at least one example of the health administration method, the receiving the identity information of the current object among the plurality of objects and the device-related data generated by the third current device and associated with the identity information of the current object comprises: acquiring, from a second individual service module, the identity information of the current object among the plurality of objects and the device-related data associated with the identity information of the current object and generated by the third current device, which are associated with each other.

For example, in at least one example of the health administration method, the health administration method further comprises: making the third current device be configured to be associated with an object identity information data acquisition terminal, the object identity information data acquisition terminal having the second individual service module built in; using the object identity information data acquisition terminal to acquire the identity information of the current object among the plurality of objects and to provide the identity information of the current object to the second individual service module; and using the second individual service module to acquire, based on an identification code of the third current device, the device-related data generated by the third current device and corresponding to the identity information of the current object, and associating the device-related data with the identity information of the current object.

For example, in at least one example of the health administration method, the health administration method further comprises: using the second individual service module to acquire basic information of the current object.

For example, in at least one example of the health administration method, the basic information of the current object is selected from height, weight, and age of the current object.

For example, in at least one example of the health administration method, the health administration method further comprises: using the second individual service module to acquire, based on the identity information of the current object, a query result provided by the health administration apparatus as to whether the current object exists in the memory; if the query result is that the current object exists in the memory, acquiring the basic information of the current object from the memory; if the query result is that the current object does not exist in the memory, acquiring the basic information of the current object, and providing the basic information and the identity information of the current object to the memory, to complete registration of the current object.

For example, in at least one example of the health administration method, the health administration method further comprises: using the second individual service module to provide at least a portion of the basic information of the current object to the third-party platform, and to acquire a predicted value of physical sign information of the current object from the third-party platform.

For example, in at least one example of the health administration method, the health administration method further comprises: using the second individual service module to acquire information of an individual and the identification code of the third current device, and to bind the individual to the third current device.

For example, in at least one example of the health administration method, the health administration method further comprises: using the second individual service module to associate, at least based on the identity information of the current object, the current object with the individual bound to the third current device, and using the second individual service module to provide an association relationship between the current object and the individual bound to the third current device to the memory associated with the health administration apparatus.

For example, in at least one example of the health administration method, the health administration method further comprises: using the second individual service module to generate, at least based on the device-related data generated by the third current device and associated with the identity information of the current object, a report of the current object.

For example, in at least one example of the health administration method, the object identity information data acquisition terminal comprises a monitor and a printer; the monitor is configured to display the report of the current object that is generated at least based on the device-related data; and the printer is configured to print the report of the current object that is generated at least based on the device-related data.

For example, in at least one example of the health administration method, the generating the device usage record of the at least one object based at least on the identity information of the at least one object among the plurality of objects and the data generated by the device used by the at least one object, comprises: acquiring a second identification code of a current object among the plurality of objects and an identification code of a fourth current device, the fourth current device being a device to be used by the current object; using the second identification code of the current object to query the memory associated with the health administration apparatus, to acquire identity information of the current object and to create a correspondence relationship between the identity information of the current object and the fourth current device; and in a case where a data receiver associated with the health administration apparatus receives device-related data originating from the fourth current device, associating the identity information of the current object with the device-related data to generate a device usage record of the current object.

For example, in at least one example of the health administration method, the acquiring the second identification code of the current object among the plurality of objects and the identification code of the fourth current device comprises: acquiring, from a first individual service module of a terminal for an individual, the second identification code of the current object among the plurality of objects and the identification code of the fourth current device.

For example, in at least one example of the health administration method, the health administration method further comprises: allowing a monitor of the terminal where the first individual service module is located to display a list of currently unused devices; using the first individual service module to select at least one device among the currently unused devices as the fourth current device, acquire the second identification code of the current object, and associate the second identification code of the current object with the identification code of the fourth current device.

For example, in at least one example of the health administration method, the health administration method further comprises: using an object service module to acquire, from the memory, a device usage record of an object associated with the object service module, and to provide the device usage record of the object associated with the object service module to a monitor of a terminal where the object service module is located.

For example, in at least one example of the health administration method, the health administration method further comprises: receiving, from an object service module, object medication record data generated according to a medication record filling operation, and providing the object medication record data to the memory associated with the health administration apparatus.

For example, in at least one example of the health administration method, the health administration method further comprises: acquiring, from an object service module, atmospheric condition data, which is acquired via the object service module, of a geographic location where an object using the object service module is located, and providing the atmospheric condition data to the memory associated with the health administration apparatus.

For example, in at least one example of the health administration method, the health administration method further comprises: acquiring, from a first individual service module, object visit situation data generated according to an object visit situation filling operation, and providing the object visit situation to the memory associated with the health administration apparatus.

For example, in at least one example of the health administration method, the health administration method further comprises: generating a barcode of an individual based on an identification code of the individual.

For example, in at least one example of the health administration method, the health administration method further comprises: using a first individual service module for the individual to acquire identity information and a device usage record of the object associated with the individual and to provide the identity information and the device usage record of the object associated with the individual to a monitor of a terminal where the first individual service module is located; using the object service module to acquire the identification code of the individual by scanning the barcode of the individual through a barcode scanner, and to provide a first identification code of an object associated with the object service module and the identification code of the individual to the memory, for establishing an association relationship between the individual and the object associated with the object service module.

For example, in at least one example of the health administration method, the health administration method further comprises: grading a plurality of members belonging to an organization, and enabling a member of an $N^{th}$-level in the organization to have an authority to acquire data of a member of an $M^{th}$-level in the organization, N being a positive integer greater than 1, and M being a positive integer greater than or equal to 1 and less than N.

For example, in at least one example of the health administration method, the health administration method further comprises: receiving a statistical data viewing request sent by the member of the $N^{th}$-level; acquiring data of at least some members among members from a first-level to the $N^{th}$-level based on the statistical data viewing request; analyzing the data of the at least some members to acquire a statistical result, and outputting the statistical result.

For example, in at least one example of the health administration method, the statistical result comprises at least one selected from a group consisting of: a total number of objects associated with the at least some members, a number of newly added objects associated with the at least some members, gender distribution of the objects associated with the at least some members, regional distribution of the objects associated with the at least some members, and level distribution of the objects associated with the at least some members.

At least one embodiment of the present disclosure also provides a non-transitory storage medium, the non-transitory storage medium stores computer program instructions, when executed by a processor, the computer program instructions cause a computer to execute a following method, comprising: generating a device usage record of at least one object based at least on identity information of the at least one object among the plurality of objects and data generated by a device used by the at least one object, and providing the device usage record of the at least one object to a memory associated with a health administration apparatus.

At least one embodiment of the present disclosure also provides a health administration apparatus, comprising: a processor and a memory. The memory stores computer program instructions suitable for being executed by the processor; and when executed by the processor, the computer program instructions cause the processor to execute a following method, comprising: generating a device usage record of at least one object based at least on identity information of the at least one object among the plurality of objects and data generated by a device used by the at least one object, and providing the device usage record of the at least one object to a memory associated with the health administration apparatus.

At least one embodiment of the present disclosure also provides a health administration system, which comprises any health administration apparatus provided by at least one embodiment of the present disclosure and a plurality of devices.

For example, in at least one example of the health administration system, the plurality of devices are selected from a group consisting of: ventilators, oxygen generators, non-invasive multi-parameter detectors, pulse oximeters, and pulmonary function instruments.

For example, in at least one example of the health administration system, the plurality of devices comprises a third current device; the generating the device usage record of the at least one object based at least on the identity information of the at least one object among the plurality of objects and the data generated by the device used by the at least one object, comprises: receiving identity information of a current object among the plurality of objects and device-related data generated by a third current device and associated with the identity information of the current object, the third current device being a device that has been used by the current object; and generating the device usage record of the current object based at least on the identity information of the current object and the device-related data generated by the third current device and associated with the identity information of the current object.

For example, in at least one example of the health administration system, the health administration system further comprises an object identity information data acquisition terminal and a second individual service module. The third current device is configured to be associated with the object identity information data acquisition terminal, the object identity information data acquisition terminal has the second individual service module built in; the object identity information data acquisition terminal is configured to acquire the identity information of the current object among the plurality of objects, and to provide the identity information of the current object to the second individual service module; and the second individual service module is configured to acquire, based on an identification code of the third current device, the device-related data generated by the third current device and corresponding to the identity information of the current object, associate the device-related data and the identity information of the current object with each other, and provide the device-related data and the identity information of the current object associated with each other to the health administration apparatus.

For example, in at least one example of the health administration system, the second individual service module is further configured to: acquire, based on the identity information of the current object, a query result provided by the health administration apparatus as to whether the current object exists in the memory; if the query result is that the current object exists in the memory, acquire basic information of the current object from the memory; if the query result is that the current object does not exist in the memory, acquire the basic information of the current object, and provide the basic information and the identity information of the current object to the memory, to complete registration of the current object.

For example, in at least one example of the health administration system, the second individual service module is further configured to acquire information of an individual and the identification code of the third current device, and bind the individual to the third current device.

For example, in at least one example of the health administration system, the second individual service module is further configured to: associate, at least based on the identity information of the current object, the current object with the individual bound to the third current device, and provide an association relationship between the current object and the individual bound to the third current device to the memory associated with the health administration apparatus.

For example, in at least one example of the health administration system, the second individual service module is further configured to generate a report of the current object at least based on the device-related data generated by the third current device and associated with the identity information of the current object.

For example, in at least one example of the health administration system, the object identity information data acquisition terminal comprises a monitor and a printer; the monitor is configured to display the report of the current object that is generated at least based on the device-related data; and the printer is configured to print the report of the current object that is generated at least based on the device-related data.

For example, in at least one example of the health administration system, the third current device is a respiratory screening instrument.

At least one embodiment of the present disclosure also provides a data collection apparatus, which comprises: an object identity information data acquisition terminal, a second individual service module, and a third current device. The second individual service module is used in the object identity information data acquisition terminal; the third current device is configured to be associated with the object identity information data acquisition terminal; the object identity information data acquisition terminal is configured to acquire identity information of a current object and provide the identity information of the current object to the second individual service module; and the second individual service module is configured to acquire, based on an identification code of the third current device, device-related data generated by the third current device and corresponding to the identity information of the current object, and associate the device-related data and the identity information of the current object with each other.

At least one embodiment of the present disclosure also provides another health administration apparatus, which involves a plurality of objects and a plurality of devices and includes a record creation module and a memory. The record creation module is configured to generate a device usage record of at least one object based at least on identity information of the at least one object among the plurality of objects and data generated by a device used by the at least one object, and provide the device usage record of the at least one object to the memory associated with a health administration apparatus.

For example, in at least one example of the health administration apparatus, the record creation module comprises a first record creation sub-module. The first record creation sub-module is configured to: acquire a first identification code of a current object among the plurality of objects and an identification code of a first current device, the first current device being a device that has been used by the current object; use the identification code of the first current device to query the memory associated with the health administration apparatus, to acquire latest device-related data originating from the first current device and transferred to the memory; use the first identification code of the current object to query the memory, to acquire identity information of the current object; associate the identity information of the current object with the latest device-related data to generate the device usage record of the current object; and provide the device usage record of the current object to the memory associated with the health administration apparatus.

For example, in at least one example of the health administration apparatus, the first record creation sub-module is configured to communicate with the object service module of a terminal for the current object, to acquire the first identification code of the current object and the identification code of the first current device from the object service module.

For example, in at least one example of the health administration apparatus, the health administration apparatus also comprises a device administration module. The device administration module is configured to generate a barcode of the first current device based on the identification code of the first current device; and the object service module is configured to scan the barcode of the first current device through a barcode scanner to acquire the identification code of the first current device.

For example, in at least one example of the health administration apparatus, the first current device is configured to allow the device-related data generated by the first current device to be transferred to the memory via a third-party platform.

For example, in at least one example of the health administration apparatus, the first current device is selected from a group consisting of: ventilators, oxygen generators, non-invasive multi-parameter detectors, and pulmonary function instruments.

For example, in at least one example of the health administration apparatus, the record creation module comprises a second record creation sub-module. The second record creation sub-module is configured to: acquire a first identification code of a current object among the plurality of objects and an identification code of a second current device, the second current device being a device to be used by the current object; use the first identification code of the current object to query the memory associated with the health administration apparatus, to acquire identity information of the current object, and create a correspondence relationship between the identity information of the current object and the second current device; in a case where a data receiver associated with the health administration apparatus receives device-related data originating from the second current device, associate the identity information of the current object with the device-related data to generate a device usage record of the current object; and provide the device usage record of the current object to the memory associated with the health administration apparatus.

For example, in at least one example of the health administration apparatus, the second record creation sub-module is configured to communicate with the object service module of a terminal for the current object, to acquire the first identification code of the current object and the identification code of the second current device from the object service module.

For example, in at least one example of the health administration apparatus, the health administration apparatus also comprises a device administration module. The device administration module is configured to generate a barcode of the second current device based on the identification code of the second current device; and the object service module is configured to scan the barcode of the first current device through a barcode scanner to acquire the identification code of the second current device.

For example, in at least one example of the health administration apparatus, the second current device is configured to allow the device-related data generated by the second current device to be transferred to the data receiver associated with the health administration apparatus via a Bluetooth gateway; the second current device comprises a pulse oximeter.

For example, in at least one example of the health administration apparatus, the record creation module comprises a third record creation sub-module. The third record creation sub-module is configured to: provide unassociated data of at least one device of the plurality of devices, the unassociated data being configured to be displayed in a terminal, where a first individual service module is located, for an individual; communicate with the first individual service module to receive, from the first individual service module, a second identification code of an object corresponding to the unassociated data; associate the object corresponding to the unassociated data with the unassociated data, to generate a device usage record of the object corresponding to the unassociated data; and provide the device usage record of the object corresponding to the unassociated data to the memory associated with the health administration apparatus.

For example, in at least one example of the health administration apparatus, the associating the object corresponding to the unassociated data with the unassociated data comprises: using the second identification code of the object corresponding to the unassociated data to query the memory associated with the health administration apparatus, to acquire identity information of the object corresponding to the unassociated data; and associating the identity information of the object corresponding to the unassociated data with the unassociated data.

For example, in at least one example of the health administration apparatus, the record creation module comprises a fourth record creation sub-module. The fourth record creation sub-module is configured to: receive identity information of a current object among the plurality of objects and device-related data generated by a third current device and associated with the identity information of the current object, the third current device being a device that has been used by the current object; generate the device usage record of the current object based at least on the identity information of the current object and the device-related data generated by the third current device and associated with the identity information of the current object; and provide the device usage record of the current object to the memory associated with the health administration apparatus.

For example, in at least one example of the health administration apparatus, the third current device is configured to be associated with an object identity information data acquisition terminal, and the object identity information data acquisition terminal has a second individual service module built in; the object identity information data acquisition terminal is configured to obtain the identity information of the current object among the plurality of objects, and provide the identity information of the current object to the second individual service module; and the second individual service module is configured to acquire, based on an identification code of the third current device, the device-related data generated by the third current device and corresponding to the identity information of the current object, associate the device-related data with the identity information of the current object, and provide the device-related data and the identity information of the current object that are associated with each other to the fourth record creation sub-module.

For example, in at least one example of the health administration apparatus, the third current device is a respiratory screening instrument, and the respiratory screening instrument is configured to collect respiratory-related physical sign information data of the current subject.

For example, in at least one example of the health administration apparatus, the second individual service module is also configured to obtain basic information of the current object.

For example, in at least one example of the health administration apparatus, the basic information of the current object is selected from a group consisting of height, weight, and age of the current object.

For example, in at least one example of the health administration apparatus, the second individual service module is also configured to acquire, based on the identity information of the current object, a query result provided by the health administration apparatus as to whether the current object exists in the memory; if the query result is that the current object exists in the memory, acquire the basic information of the current object from the memory; if the query result is that the current object does not exist in the memory, acquire the basic information of the current object, and provide the basic information and the identity information of the current object to the memory, to complete registration of the current object.

For example, in at least one example of the health administration apparatus, the second individual service module is also configured to provide at least a portion of the basic information of the current object to the third-party platform, and to acquire a predicted value of physical sign information of the current object from the third-party platform.

For example, in at least one example of the health administration apparatus, the second individual service module is also configured to acquire information of an individual and the identification code of the third current device, and to bind the individual to the third current device.

For example, in at least one example of the health administration apparatus, the second individual service module is also configured to associate, at least based on the identity information of the current object, the current object with the individual bound to the third current device, and to provide an association relationship between the current object and the individual bound to the third current device to the memory associated with the health administration apparatus.

For example, in at least one example of the health administration apparatus, the second individual service module is also configured to generate, at least based on the device-related data generated by the third current device and associated with the identity information of the current object, a report of the current object.

For example, in at least one example of the health administration apparatus, the object identity information data acquisition terminal comprises a monitor and a printer; the monitor is configured to display the report of the current object that is generated at least based on the device-related data; and the printer is configured to print the report of the current object that is generated at least based on the device-related data.

For example, in at least one example of the health administration apparatus, the record creation module comprises a fifth record creation sub-module. The fifth record creation sub-module is configured to: receive and acquire a second identification code of a current object among the plurality of objects and an identification code of a fourth current device, the fourth current device being a device to be used by the current object; use the second identification code of the current object to query the memory associated with the health administration apparatus, to acquire identity information of the current object and to create a correspondence relationship between the identity information of the current object and the fourth current device; and in a case where a data receiver associated with the health administration apparatus receives device-related data originating from the fourth current device, associate the identity information of the current object with the device-related data to generate a device usage record of the current object; and provide the device usage record of the current object to the memory associated with the health administration apparatus.

For example, in at least one example of the health administration apparatus, the health administration apparatus also comprises a first individual service module of a terminal for an individual. A monitor of the terminal where the first individual service module is located is configured to display a list of currently unused devices; the first individual service module is configured to select at least one device among the currently unused devices as the fourth current device, acquire the second identification code of the current object, associate the second identification code of the current object with the identification code of the fourth current device, and provide the second identification code of the current object and the identification code of the fourth current device to the fifth record creation sub-module.

For example, in at least one example of the health administration apparatus, the health administration apparatus further comprises an object service module. The object service module is configured to communicate with the memory associated with the health administration apparatus, to acquire, from the memory, a device usage record of an object associated with the object service module and to provide the device usage record of the object associated with the object service module to a monitor of a terminal where the object service module is located.

For example, in at least one example of the health administration apparatus, the object service module is also configured to: obtain the first identification code of the object associated with the object service module and the identification code of the device used by the object associated with the object service module, and output the first identification code of the object associated with the object service module and the identification code of the device used by the object associated with the object service module.

For example, in at least one example of the health administration apparatus, the health administration apparatus further comprises a first individual service module. The first individual service module is configured to communicate with the memory to acquire the identity information and the device usage record of the object associated with the individual, and to provide the identity information and the device usage record of the object associated with the individual to the display of the terminal where the first individual service module is located.

For example, in at least one example of the health administration apparatus, the first individual service module is further configured to generate a barcode of an individual based on an identification code of the individual; and the object service module is further configured to acquire the identification code of the individual by scanning the barcode of the individual through a barcode scanner, and to provide a first identification code of an object associated with the object service module and the identification code of the individual to the memory, for establishing an association relationship between the individual and the object associated with the object service module.

For example, in at least one example of the health administration apparatus, the health administration apparatus also comprises an organization administration module. The organization administration module is configured to: grade a plurality of members belonging to an organization, and enable a member of an $N^{th}$-level in the organization to have an authority to acquire data of a member of an $M^{th}$-level in the organization, N being a positive integer greater than 1, and M being a positive integer greater than or equal to 1 and less than N For example, in at least one example of the health administration apparatus, the organization administration module comprises a data statistics module, and the data statistics module is configured to: receive a statistical data viewing request sent by the member of the $N^{th}$-level; acquire data of at least some members among members from a first-level to the $N^{th}$-level based on the statistical data viewing request; analyze the data of the at least some members to acquire a statistical result; and output the statistical result.

For example, in at least one example of the health administration apparatus, the statistical result comprises at least one selected from a group consisting of: a total number of objects associated with the at least some members, a number of newly added objects associated with the at least some members, gender distribution of the objects associated with the at least some members, regional distribution of the objects associated with the at least some members, and level distribution of the objects associated with the at least some members.

At least one embodiment of the present disclosure also provides a data collection apparatus, which includes: an object identity information data acquisition terminal, a second individual service module, and a third current device. The second individual service module is used in the object identity information data acquisition terminal; the third current device is configured to be associated with the object identity information data acquisition terminal; the object identity information data acquisition terminal is configured to acquire identity information of a current object and provide the identity information of the current object to the second individual service module; and the second individual service module is configured to acquire, based on an identification code of the third current device, device-related data generated by the third current device and corresponding to the identity information of the current object, and associate the device-related data and the identity information of the current object with each other.

For example, in at least one example of the data collection apparatus, the data collection apparatus communicates with the health administration apparatus to provide the device-related data and the identity information of the current object that are associated with each other to the health administration apparatus.

For example, in at least one example of the data collection apparatus, the third current device is a respiratory screening instrument, and the respiratory screening instrument is configured to collect respiratory-related physical sign information data of the current subject.

For example, in at least one example of the data collection apparatus, the second individual service module is also configured to obtain basic information of the current object.

For example, in at least one example of the data collection apparatus, the basic information of the current object is selected from a group consisting of height, weight, and age of the current object.

For example, in at least one example of the data collection apparatus, the second individual service module is also configured to acquire, based on the identity information of the current object, a query result provided by the health administration apparatus as to whether the current object exists in the memory; if the query result is that the current object exists in the memory, acquire the basic information of the current object from the memory; if the query result is that the current object does not exist in the memory, acquire the basic information of the current object, and provide the basic information and the identity information of the current object to the memory, to complete registration of the current object.

For example, in at least one example of the data collection apparatus, the second individual service module is also configured to provide at least a portion of the basic information of the current object to the third-party platform, and to acquire a predicted value of physical sign information of the current object from the third-party platform.

For example, in at least one example of the data collection apparatus, the second individual service module is also configured to acquire information of an individual and the identification code of the third current device, and to bind the individual to the third current device.

For example, in at least one example of the data collection apparatus, the second individual service module is also configured to associate, at least based on the identity information of the current object, the current object with the individual bound to the third current device, and to provide an association relationship between the current object and the individual bound to the third current device to the memory associated with the health administration apparatus.

For example, in at least one example of the data collection apparatus, the second individual service module is also configured to generate, at least based on the device-related data generated by the third current device and associated with the identity information of the current object, a report of the current object.

For example, in at least one example of the data collection apparatus, the object identity information data acquisition terminal comprises a monitor and a printer; the monitor is configured to display the report of the current object that is generated at least based on the device-related data; and the printer is configured to print the report of the current object that is generated at least based on the device-related data.

At least one embodiment of the present disclosure also provides a rehabilitation module, which involves a plurality of objects and comprises: a rehabilitation data acquisition sub-module and a rehabilitation report generation sub-module. The rehabilitation data acquisition sub-module is configured to acquire data generated by a device used by at least one object among the plurality of objects, and provide the data generated by the device used by the at least one object among the plurality of objects to the rehabilitation report generation sub-module; and the rehabilitation report generation sub-module is configured to generate a rehabilitation report at least based on the data generated by the device used by the at least one object, and output the rehabilitation report.

For example, in at least one example of the rehabilitation module, the rehabilitation data acquisition sub-module is configured to communicate with a rehabilitation data analyzing sub-module, to acquire analysis data generated by the rehabilitation data analyzing sub-module and provide the analysis data to the rehabilitation report generation sub-module; and the rehabilitation report generation sub-module is configured to generate the rehabilitation report at least based on the data generated by the device used by the at least one object among the plurality of objects and the analysis data.

For example, in at least one example of the rehabilitation module, the rehabilitation data analyzing sub-module is configured to generate the analysis data based on the data generated by the device used by the at least one object and template data.

For example, in at least one example of the rehabilitation module, the rehabilitation data analyzing sub-module is configured to perform logistic regression analysis, based on the data generated by the device used by the at least one object and the template data, to generate the analysis data.

For example, in at least one example of the rehabilitation module, the rehabilitation data analyzing sub-module is integrated in a gateway that communicates with the device used by the at least one object; and the rehabilitation data analyzing sub-module receives the data generated by the device used by the at least one object among the plurality of objects from the gateway.

For example, in at least one example of the rehabilitation module, the device used by the at least one object comprises at least one type of devices arranged in a nursing home, a rehabilitation center, and a hospital.

For example, in at least one example of the rehabilitation module, the device used by the at least one object comprises a personal device of the at least one object.

For example, in at least one example of the rehabilitation module, the rehabilitation module further includes a remote management module, the remote management module is configured to communicate with the rehabilitation report generation sub-module, to acquire the rehabilitation report.

For example, in at least one example of the rehabilitation module, the rehabilitation module further comprises an individual service module for the terminal of the individual. The remote management module is configured to provide the rehabilitation report to the individual service module; and the terminal where the individual service module is located is configured to display the rehabilitation report to allow the individual to provide advice to the at least one object.

For example, in at least one example of the rehabilitation module, the rehabilitation module further comprises an object service module for at least one object. The remote management module is configured to provide the rehabilitation report to the object service module; and the terminal where the object service module is located is configured to display the rehabilitation report to allow the at least one object to view.

For example, in at least one example of the rehabilitation module, the remote management module allows the object service module to communicate with the individual service module, to allow the individual to communicate with the at least one object.

For example, in at least one example of the rehabilitation module, the rehabilitation module further comprises a relative-and-friend service module for relatives and friends of the at least one object; the remote management module is configured to provide the rehabilitation report to the relative-and-friend service module; and the terminal where the relative-and-friend service module is located is configured to display the rehabilitation report, to allow the relatives and the friends of the at least one object to view.

For example, in at least one example of the rehabilitation module, the remote management module allows the relative-and-friend service module to communicate with at least one selected form a group consisting of the object service module and the individual service module, so as to allow the relatives and the friends of the at least one object to communicate with the individual and the at least one object.

For example, in at least one example of the rehabilitation module, the device used by the at least one object among the plurality of objects comprises at least one category selected form a group consisting of a hospital device, a rehabilitation center device, a nursing home device, and a personal device.

BRIEF DESCRIPTION OF THE DRAWINGS

In order to clearly illustrate the technical solutions of the embodiments of the present disclosure, the drawings of the embodiments will be briefly described in the following; it is obvious that the described drawings are only related to some embodiments of the present disclosure and thus are not limitative to the present disclosure.

FIG. 2B is a schematic diagram of a report query interface of an object service module provided by at least one embodiment of the present disclosure;

FIG. 3A is a patient list display page of a first individual service module provided by at least one embodiment of the present disclosure;

FIG. 3B is a schematic diagram of an object detail page of the first individual service module shown in FIG. 3A;

FIG. 3C shows a schematic diagram of a device usage record page of the object of the first individual service module shown in FIG. 3A;

FIG. 3D shows a schematic diagram of a "personal center" page of a first individual service module provided by at least one embodiment of the present disclosure;

FIG. 3E is a schematic diagram of a barcode of an individual provided by at least one embodiment of the present disclosure;

FIG. 3H shows a schematic diagram of a registration page of an object service module provided by at least one embodiment of the present disclosure;

FIG. 7 shows a schematic diagram of an "in-hospital data" page of a first individual service module provided by at least one embodiment of the present disclosure;

FIG. 8 is an exemplary block diagram of a fourth example of a record creation module provided by at least one embodiment of the present disclosure;

FIG. 9A is a schematic diagram of a graphical user interface of a second individual service module provided by at least one embodiment of the present disclosure;

FIG. 12B shows a schematic diagram of an object information confirmation interface of the second individual service module shown in FIG. 9A;

FIG. 12C shows a schematic diagram of a third current device usage page of the second individual service module shown in FIG. 9A;

FIG. 12F is a report of an object associated with an individual displayed on a monitor of a terminal where the object associated with the individual is located provided by at least one embodiment of the present disclosure;

FIG. 13 is a schematic block diagram of a fifth example of a record creation module provided by at least one embodiment of the present disclosure;

FIG. 14 is a schematic block diagram of a sixth example of a record creation module provided by at least one embodiment of the present disclosure;

FIG. 15 is a schematic block diagram of a seventh example of a record creation module provided by at least one embodiment of the present disclosure;

FIG. 16 is an exemplary block diagram of another health administration apparatus provided by at least one embodiment of the present disclosure;

FIG. 17 is a schematic diagram of a front-end page associated with an organization administration module provided by at least one embodiment of the present disclosure;

FIG. 59 is a schematic diagram of atmospheric condition data in the object detail page of the first individual service module provided by at least one embodiment of the present disclosure;

FIG. 60 is a schematic diagram of an atmospheric condition data display page provided by at least one embodiment of the present disclosure;

FIG. 61 is a schematic diagram of a follow-up record page in the object detail page of the first individual service module provided by at least one embodiment of the present disclosure;

FIG. 62 is a schematic diagram of a new follow-up content page of the first individual service module provided by at least one embodiment of the present disclosure;

FIG. 63 is a schematic diagram of a portion of a chronic obstructive pulmonary disease screening questionnaire fill-in page provided by at least one embodiment of the present disclosure;

FIG. 64 is a schematic diagram of a follow-up content view page of the first individual service module provided by at least one embodiment of the present disclosure;

FIG. 65 is a schematic diagram of the object detail page of the first individual service module provided by at least one embodiment of the present disclosure; and FIG. 66 is a schematic diagram of a patient grouping page of the first individual service module provided by at least one embodiment of the present disclosure.

DETAILED DESCRIPTION

Figure 1:
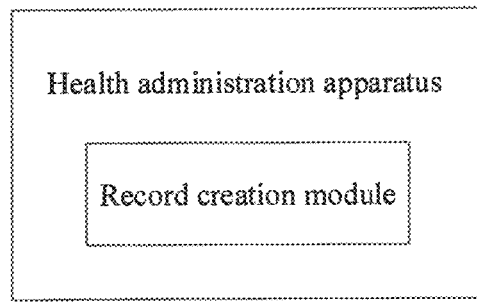
FIG. 1 is an exemplary block diagram of a health administration apparatus provided by at least one embodiment of the present disclosure.

In order to make objects, technical solutions, and advantages of the embodiments of the present disclosure apparent, the technical solutions of the embodiments of the present disclosure will be described in a clearly and fully understandable way in connection with the drawings related to the embodiments of the present disclosure. Apparently, the described embodiments are just a part but not all of the embodiments of the present disclosure. Based on the described embodiments of the present disclosure, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. Similarly, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

An inventor of the present disclosure notices in research that a patient with chronic disease needs to use a relative device for a long time; and the relative device will generate data during or after the patient with chronic disease uses the relative device. However, the inventor of the present disclosure notices in research that, use information that the patient with chronic disease uses the relative device has to be manually recorded; in a case of more patients with chronic disease and more relative devices, it takes more time and manpower to record the use information that the patients with chronic disease use the relative devices, thereby reducing the work efficiency of medical workers. For example, manually recording the use information that patients with chronic disease use the relative devices also lowers an update speed of data of the patients with chronic disease.

The inventor of the present disclosure also notices in research that, if patients with chronic disease undergo appropriate (or targeted) rehabilitation training, time required for healing can be shortened. However, currently, rehabilitation training adopted by the patients with chronic disease has relatively poor applicability, and it is difficult for the patients with chronic disease to adhere to long-term rehabilitation training, especially for patients with chronic disease who live alone.

The inventor of the present disclosure also notices in research that, different hospitals have different resource constraints, which results in poor effect and experience for patients seeking medical consultation.

In a process of implementing a two-way referral system, the inventor of the present disclosure finds in research that there are at least problems below in a related art: due to the large number of patient users and complexity of patient information, problems such as confused patient information administration and information docking, poor real-time performance of patient information transfer, or the need to manually transmit patient information, etc. commonly exist in a referral process, resulting in low referral efficiency.

The inventor of the present disclosure notices in research that, when a patient user is referred by a current administration system for administrating two-way referral, it is always the case that a referral request is sent by an administration system of one hospital to an administration system of another hospital, or a referral request is sent by an administration system of one medical system to an administration system of another medical system; however, in an actual situation, due to the large number of patient users and complexity of patient information in an administration system of a hospital or an administration system of a medical system, a degree of refinement of the patient information administration in the referral process is low, so that there may be many problems in the referral process, such as confused administration and docking of patient information, and poor real-time performance of patient information transfer, etc., resulting in low referral efficiency.

The inventor of the present disclosure notices in research that, because the data of the patients cannot be updated in time, the patient's illness condition cannot be estimated in real time based on personalized data of the patient, so that the patients have the illness conditions delayed during waiting for referral. In turn, patients are more inclined to directly go to superior hospitals for treatment, so it difficult for basic-level hospitals to effectively play an administration role, which wastes high-quality medical resources of the superior hospitals, and brings inconvenience to the lives of the people.

At least one embodiment of the present disclosure provides a health administration method, a health administration apparatus, a health administration system, and a data collection apparatus; the health administration apparatus involves a plurality of objects and a plurality of devices, and includes a record creation module and a memory. The record creation module is configured to generate a device usage record of at least one object at least based on identity information of the at least one object among the plurality of objects and data generated by the device used by the at least one object, and provide the device usage record of the at least one object to the memory associated with the health administration apparatus; and the health administration method, the health administration apparatus, the health administration system, and the data collection apparatus can improve work efficiency of medical workers.

In some examples, by speeding up association between identity information of an object and device-related data generated by a device used by the object, information of the object can be updated more quickly, which is favorable for speeding up an early warning. For example, when the object's illness condition is getting worse or has a tendency to worsen, the object may be reminded of development of his/her illness condition more quickly.

In some examples, an association relationship between two pieces of data refers to that one of the two pieces of data may be used to retrieve the other of the two pieces of data; an association relationship between two modules refers to that the two modules are bound to each other in one-to-one correspondence; an association relationship between a module and a page refers to that data interaction may be performed between the module and the page.

In some examples, modules and sub-modules involved in at least one embodiment of the present disclosure may be implemented by software, firmware, hardware, and any combination thereof; for example, the hardware includes a server and a Field Programmable Gate Array (FPGA), etc.

Hereinafter, non-restrictive description is given for the health administration apparatus provided by the embodiments of the present disclosure through several examples and embodiments; and as described below, different features in the specific examples and embodiments may be combined with each other without conflicts, so as to acquire new examples and embodiments, and all of the new examples and embodiments also belong to the protection scope of the present disclosure.

FIG. 1 is an exemplary block diagram of a health administration apparatus provided by at least one embodiment of the present disclosure. As shown in FIG. 1, the health administration apparatus includes a record creation module, and involves a plurality of objects and a plurality of devices (i.e., the health administration apparatus is associated with a plurality of objects and a plurality of devices). For example, the health administration apparatus is configured to administrate the plurality of objects and the plurality of devices.

For example, the health administration apparatus may be a health administration apparatus. For example, the health administration apparatus may be a health administration apparatus for chronic disease, for example, the health administration apparatus for chronic disease may be a health administration apparatus for respiratory disease. For example, the health administration apparatus includes information on the plurality of objects and information on the plurality of devices.

It should be noted that, at least one embodiment of the present disclosure is exemplarily described by implementing a health administration apparatus as a health administration system for chronic disease, but the embodiments of the present disclosure are not limited thereto.

For example, the plurality of objects are associated with the health administration apparatus. For example, the plurality of objects are a plurality of patients (e.g., patients with chronic disease).

For example, the plurality of devices are associated with the health administration apparatus. For example, the plurality of devices are devices for use of the plurality of objects (e.g., patients). For example, the plurality of devices may include at least one category of an in-hospital device and a personal device. For example, the in-hospital device refers to devices arranged in at least one category of a hospital, a nursing home, and a rehabilitation center. For example, the personal device refers to a device belonging to an object (e.g., a patient with chronic disease) himself/herself. For example, the plurality of devices may include at least one category of a detection device (e.g., a non-invasive multi-parameter detector) and a treating device (e.g., an oxygen generator). For example, the plurality of devices are selected from a group consisting of pulse oximeters, ventilators, oxygen generators, non-invasive multi-parameter detectors, and pulmonary function instruments (or respiratory screening instruments).

For example, the record creation module is configured to generate a device usage record of at least one object, at least based on identity information of at least one object among the plurality of objects and data generated by a device used by the at least one object, and provide the device usage record of the at least one object to a memory associated with the health administration apparatus.

For example, by making the health administration apparatus include the record creation module, work efficiency of a medical worker using the health administration apparatus can be improved.

For example, the identity information of the at least one object includes at least one selected from a group consisting of an identity card number and a passport number of the at least one object. For example, the identity information of the at least one object also includes name of the at least one object.

For example, the memory associated with the health administration apparatus may include at least one selected from a group consisting of a volatile memory and a non-volatile memory. For example, the memory may include a Read-Only Memory (ROM), a hard disk, a flash memory, and the like. It should be noted that, querying the memory refers to querying a database associated with memory.

For example, the record creation module may include at least one selected from a group consisting of a first record creation sub-module, a second record creation sub-module, a third record creation sub-module, a fourth record creation sub-module, and a fifth record creation sub-module. For example, the first record creation sub-module, the second record creation sub-module, the third record creation sub-module, the fourth record creation sub-module, and the fifth record creation sub-module may be implemented by a server (e.g., a back end). In some examples, at least part of functions of at least one selected from a group consisting of the first record creation sub-module, the second record creation sub-module, the third record creation sub-module, the fourth record creation sub-module, and the fifth record creation sub-module may also be implemented by a local end. For example, specific implementation modes of the first record creation sub-module, the second record creation sub-module, the third record creation sub-module, the fourth record creation sub-module, and the fifth record creation sub-module will be exemplarily described in conjunction with relevant examples, and no details will be repeated here.

For example, the health administration apparatus may further include at least one selected from a group consisting of a first individual service module, a device administration module, a two-way referral module, and a patient administration module. For example, the first individual service module is implemented by a front end (e.g., a front-end page); and the record creation module (e.g., the third record creation sub-module), the device administration module, the two-way referral module, and the patient administration module are implemented by a server; in this case, the first individual service module includes a device administration page, a two-way referral administration page, a patient administration page, and an in-hospital data page; the device administration page communicates with the device administration module described later in detail, to transfer related data; the two-way referral administration page communicates with the two-way referral module described later in detail, to transfer related data; the patient administration page communicates with the patient administration module described later in detail, to transfer related data; and the in-hospital data page communicates with the third record creation sub-module described later in detail, to transfer related data.

For example, the health administration apparatus may further include at least one selected from a group consisting of an organization administration module, a user administration module, a device input module, and a device binding module; correspondingly, the health administration apparatus may further include at least one selected from a group consisting of an organization administration page, a user administration page, a device input page, and a device binding page; the organization administration module, the user administration module, the device input module, and the device binding module communicate with the organization administration page, the user administration page, the device input page, and the device binding page, respectively, to transfer related data.

For example, the health administration apparatus may further include a rehabilitation module and a rehabilitation page; and the rehabilitation module communicates with the rehabilitation page, to transfer related data.

For example, at least one selected from a group consisting of the organization administration module, the user administration module, the device input module, the device binding module, and the rehabilitation module is implemented by a server. For example, the organization administration page, the user administration page, the device input page, the device binding page, and the rehabilitation page are implemented by at least one of front ends.

For example, the health administration apparatus may further include at least one selected from a group consisting of an object service module, a second individual service module, and a memory. For example, the object service module may be implemented by a front end; for example, the second individual service module may be implemented by an APP, and the above-described APP involves a front end and a back end (e.g., a server). For another example, the health administration apparatus may not include the object service module and the second individual service module, but communicate with the object service module and the second individual service module, respectively.

For example, at least part of (e.g., all of) the first record creation sub-module, the second record creation sub-module, the third record creation sub-module, the fourth record creation sub-module, the fifth record creation sub-module, the device administration module, the two-way referral module, the patient administration module, the organization administration module, the user administration module, the device input module, the device binding module, and the rehabilitation module may be implemented by the same server. For example, the first record creation sub-module, the second record creation sub-module, the third record creation sub-module, the fourth record creation sub-module, the fifth record creation sub-module, the two-way referral module, and the patient administration module may be implemented by the same server.

For example, a front-end page involved in the first individual service module, a front-end page involved in the object service module, and a front-end page involved in the second individual service module are located in different terminals.

For example, a doctor who logs into the health administration apparatus can see relevant pages included in the first individual service module and perform relative operations; however, the doctor cannot see the organization administration page, the user administration page, the device input page, and the device binding page. For example, a super administrator of the health administration apparatus can see the organization administration page, the user administration page, the device input page, and the device binding page after logging into the health administration apparatus. For example, a hospital administrator can see the user administration page, the device administration page, and the organization administration page, but cannot see the device input page.

For example, specific implementation modes of the first individual service module, the device administration module, the two-way referral module, the patient administration module, the organization administration module, the user administration module, the device input module, the device binding module, the organization administration page, the user administration page, the device input page, the device binding page, the object service module, and the second individual service module will be exemplarily described in subsequent corresponding examples, and no details will be repeated here.

For example, the object service module is used in a terminal of a current object. For example, the current object is a patient currently seeking medical consultation. For example, the object service module is configured to communicate with the memory associated with the health administration apparatus, to acquire, from the memory, a device usage record of the object associated with the object service module, and provide the device usage record of the object associated with the object service module to a monitor of the terminal where the object service module is located, so as to display the device usage record on the terminal where the object service module is located. For example, the object service module may organize the above-described device-related data into a report form and display the report form on the monitor of the terminal where the object service module is located, or the health administration apparatus may also organize the above-described device-related data into a report form and then sends the report form to the terminal where the object service module is located for display, so as to facilitate the query and review by the patient with chronic disease who is currently seeking medical consultation.

Figure 2A:
FIG. 2A is a schematic diagram of an object service module provided by at least one embodiment of the present disclosure.
Figure 2A:
Figure 2A:
Figure 2A:
Figures 2B, 3A, 3B:
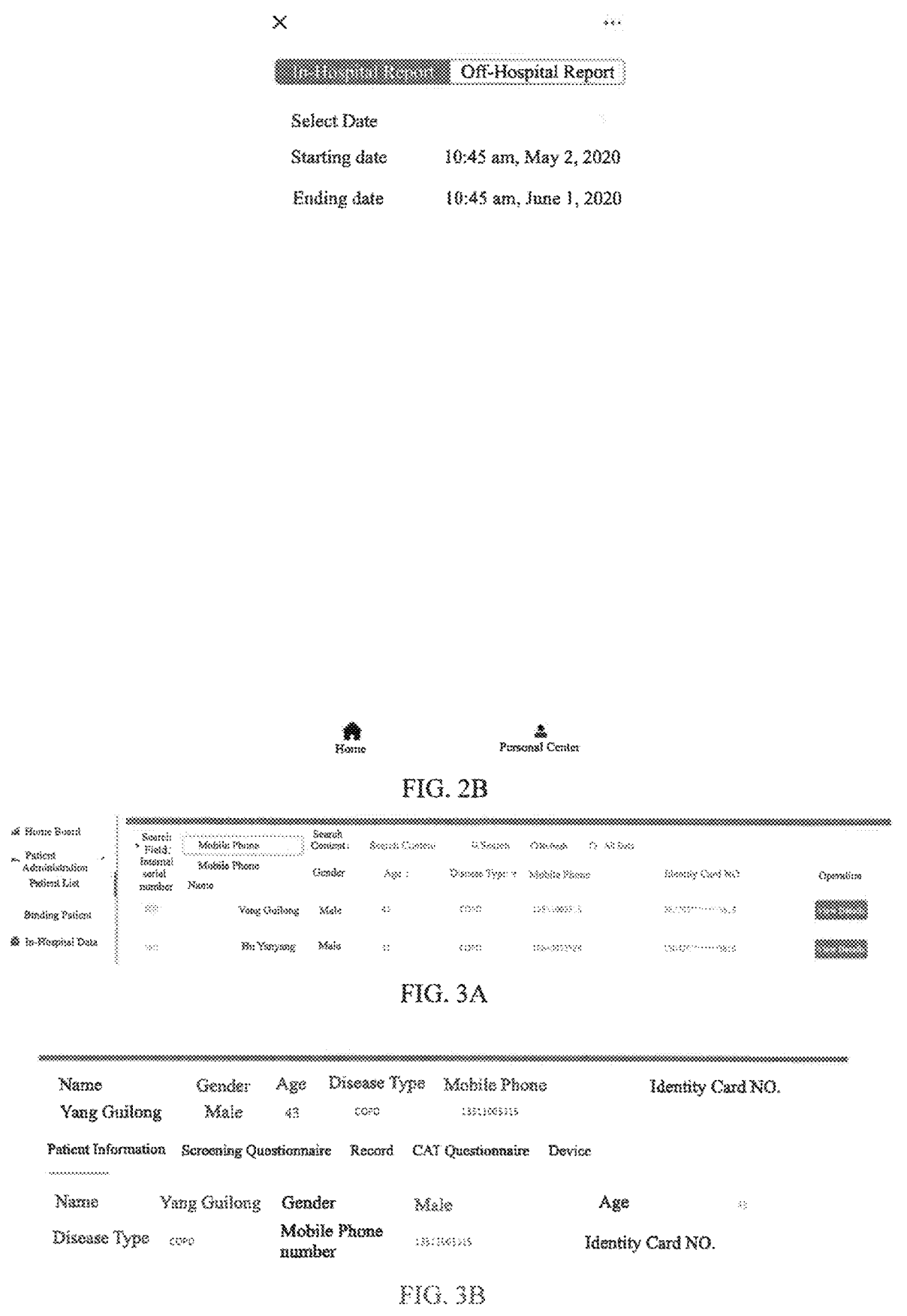

FIG. 2A is a schematic diagram of a main interface (home) of a front-end page of an object service module provided by at least one embodiment of the present disclosure. FIG. 2B is a schematic diagram of a report query (view report) interface of an object service module provided by at least one embodiment of the present disclosure. For example, as shown in FIG. 2A, the patient with chronic disease who is currently seeking medical consultation may click on a "View Report" option of the object service module shown in FIG. 2A to enter a query interface shown in FIG. 2B; the patient with chronic disease who is currently seeking medical consultation may input, in the query interface, an upload date of the device-related data related to the report he/she wants to view; and the object service module communicates with the memory associated with the health administration apparatus, to acquire the device-related data uploaded on the specified date from the memory, and organizes the above-described device-related data into a report form for display.

As shown in FIG. 2A, in some examples, the object service module is further configured to acquire a result of a questionnaire (e.g., at least one selected from a group consisting of an in-hospital questionnaire and an at-home questionnaire), and provide the result of the questionnaire to the health administration apparatus. For example, the patient currently seeking medical consultation may click on "In-Hospital Questionnaire" and "At-Home Questionnaire" files shown in FIG. 2A to fill in relative questionnaires.

As shown in FIG. 2A, in some examples, the object service module is further configured to acquire a referral notice from the health administration apparatus. For example, the patient currently seeking medical consultation may click on a "Referral Notice" button shown in FIG. 2A to acquire a referral notice.

As shown in FIG. 2A, in some examples, the object service module is further configured to acquire the device associated with the object logging in the object service module from the health administration apparatus for display on the terminal where the object service module is located.

As shown in FIG. 2A, in some examples, the object service module is further configured to extract information in a paper report, and provide the information extracted from the paper report to the health administration apparatus.

For example, the first individual service module is used in a terminal of an individual. For example, the individual is a medical worker. For example, the individual may be selected from a group consisting of a doctor, a nurse associated with the doctor, and a device administrator associated with the doctor. It should be noted that, in some examples, for convenience of description, medical workers are directly described as doctors, but those skilled in the art can understand that, in addition to doctors, nurses associated with doctors or device administrators associated with doctors may also perform related operations.

For example, the first individual service module is configured to communicate with the memory associated with the health administration apparatus, to acquire the identity information and the device usage record of the object associated with the individual, and provide the identity information and the device usage record of the object (a plurality of objects) associated with the individual to a monitor of the terminal where the first individual service module is located.

For example, the object (e.g., the plurality of objects) associated with the individual may be a patient (e.g., a plurality of patients) receiving medical service from a doctor. For example, the identity information of the object (the plurality of objects) associated with the individual may be organized into a list and displayed on the monitor of the terminal where the first individual service module is located. For example, the list may also display basic information of the object associated with the individual; for example, the basic information of the object includes at least one selected from a group consisting of gender, age, disease type, mobile phone number, height, and weight of the object. For example, one may view the device usage record of the specified object after entering a detail page associated with the identity information of the specified object.

Figure 3F:
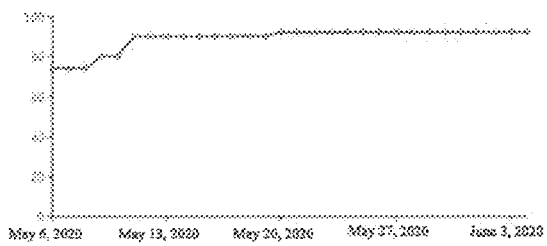
FIG. 3F shows a schematic diagram of a sub-page of binding patients in a patient administration page of a first individual service module provided by at least one embodiment of the present disclosure.

FIG. 3A is an object list display page (e.g., a patient list display page) of the first individual service module provided by at least one embodiment of the present disclosure. For example, as shown in FIG. 3A, the first individual service module may receive a search field selected by the individual (the doctor or the nurse associated with the doctor) and search content input by the individual, to search for information of the object that the individual wants to view. In one example, as shown in FIG. 3A, the search field includes "mobile phone" (i.e., the object's mobile phone number) and "name" (i.e., the object's name). In another example, the search field includes "mobile phone", "name", "device name" (i.e., a name of the device used by the object), and "device serial number" (i.e., a serial number of the device used by the object). For example, the search field includes a plurality of fields such as "mobile phone", "name", "device name" (i.e., the name of the device used by the object), and "device serial number" (i.e., the serial number of the device used by the object), which can allow the doctor to screen out the specified patient or specified data more quickly.

For example, after the individual finds the specified object by searching, the individual may click on "View Details" to view information of the specified object (e.g., the identity information and the basic information of the patient) and the device usage record of the object; for example, click on "View Details" to view the device rented from hospital and taken home for use by the specified object and the questionnaire filled out. For example, in a case where the object is a patient with Chronic Obstructive Pulmonary Disease (COPD), the questionnaire filled out by the object includes a screening questionnaire (i.e., a questionnaire for screening patients with COPD) and a questionnaire for assessing quality of life of the patients with COPD (i.e., CAT questionnaire). For example, the object may fill in a questionnaire through the foregoing object service module.

FIG. 3B is a schematic diagram of the object detail page of the first individual service module shown in FIG. 3A. For example, as shown in FIG. 3B, the device usage record of the object may be viewed by clicking on "Record", and FIG. 3C shows a schematic diagram of a device usage record page of the object of the first individual service module shown in FIG. 3A; and the identity information and the basic information of the object may be viewed by clicking on "Patient Information". For example, as shown in FIG. 3B, by clicking on "Device", the device rented from hospital and taken home for use by the object may be viewed; by clicking on "Screening Questionnaire", the questionnaire filled out may be viewed; and by clicking on "CAT Questionnaire", the filled-out questionnaire for assessing quality of life of the patients with COPD may be viewed.

For example, the first individual service module is further configured to generate a barcode of the individual based on an identification code of the individual; and the object service module is further configured to acquire the identification code of the individual by scanning the barcode of the individual via a barcode scanner, and to provide a first identification code of the object associated with the object service module and the identification code of the individual to the health administration apparatus, for establishing an association relationship between the individual and the object associated with the object service module. For example, the identification code of the individual may be selected from a mobile phone number, a work number, and an identity card number of the individual.

Exemplary description will be given below in conjunction with FIG. 3D and FIG. 3E. FIG. 3D shows a schematic diagram of a "personal center" page of the first individual service module provided by at least one embodiment of the present disclosure. As shown in FIG. 3D, the "personal center" page of the first individual service module displays information of an individual (e.g., a doctor). For example, as shown in FIG. 3D, the information of the individual includes at least one of name, address, profile, and mailbox of the individual. For example, by clicking on "View Personal Two-Dimensional Code" as shown in FIG. 3D, the first individual service module acquires the barcode of the individual generated based on the identification code of the individual; FIG. 3E is a schematic diagram of a barcode of an individual provided by at least one embodiment of the present disclosure. For example, the object may use the terminal to scan the barcode of the individual, the barcode scanner of the terminal acquires the identification code of the individual, and provides the above-described identification code of the individual to the object service module in the terminal, and the object service module provides the first identification code (e.g., a WeChat number) of the object associated with the object service module and the identification code of the individual to the memory, so that an association relationship between the individual and the object associated with the object service module may be established. For example, the association relationship between the individual and the object associated with the object service module (the object who uses the terminal to scan the barcode of the individual) may be established by the object service module and transferred to the health administration apparatus, or may be established by the health administration apparatus.

For example, the object service module provides the identity information and the basic information (e.g., the first identification code) of the object associated with the object service module to the memory. For example, the identity information and the basic information of the object associated with the object service module may be provided by the object in a registration link before the object associated with the object service module uses the object service module for the first time. FIG. 3H shows a schematic diagram of a registration page of the object service module provided by at least one embodiment of the present disclosure. As shown in FIG. 3H, in the registration link before using the object service module for the first time, the object may input the identity information and the basic information of the object on the registration page shown in FIG. 3H, and the above-described information of the object will be acquired by the object service module and provided to the health administration apparatus.

In another example, the first individual service module is configured to receive the mobile phone number of the object to be associated (e.g., receive the mobile phone number input by the individual into a graphical user interface of the first individual service module), query the memory to determine whether the object to be associated exists in the health administration apparatus; if the object to be associated exists in the health administration apparatus, acquire the identity information of the object to be associated from the memory associated with the health administration apparatus, so as to (allow, for example, a patient binding sub-module of the patient administration module to) establish an association relationship between the identity information of the object to be associated and the identification code of the individual; if the object to be associated does not exist in the health administration apparatus, acquire the identity information of the object to be associated that is input by the individual to (allow, for example, the patient binding sub-module of the patient administration module to) establish an association relationship between the identity information of the object to be associated and the identification code of the individual. For example, the mobile phone number of the object to be associated input by the individual may be received through the patient binding sub-page (referring to FIG. 3F) in the patient administration page shown in FIG. 3A.

For example, as shown in FIG. 3D, the first individual service module further includes at least one selected from a group consisting of a device administration page, a referral administration page, and an in-hospital data page. For example, the device administration page, the referral administration page, and the in-hospital data page respectively communicate with the device administration module, the two-way referral module, and the third record creation sub-module, which are described later in detail, to transfer related data. For example, specific implementation modes of the device administration page, the referral administration page, and the in-hospital data page will be exemplarily described in subsequent corresponding examples, and no details will be repeated here.

Figure 3G:
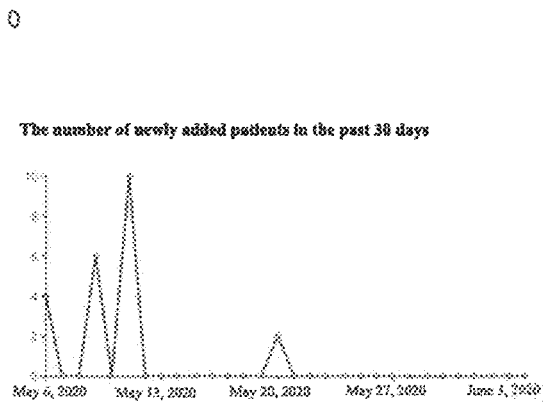
FIG. 3G shows a schematic diagram of a home board page of a first individual service module provided by at least one embodiment of the present disclosure.

For example, the first individual service module further includes a home board page. FIG. 3G shows a schematic diagram of the home board page of the first individual service module provided by at least one embodiment of the present disclosure. For example, the home board page may display the total number of objects (patients) and the number of newly added objects (patients) bound to the individual (the doctor) in a form of numbers and curves.

For example, the object service module and the first individual service module may be implemented as a local end (or a front end). For example, the above-described local end or front end may be implemented by at least one selected from a group consisting of a network end, a mobile end, and a desktop end. For example, the mobile end may be implemented by an APP and an applet. For example, the applet may be a WeChat applet, an Alipay applet, or other applicable applets. For example, the object service module may be implemented by a WeChat applet. For example, the first individual service module may be implemented by a network end.

For example, the terminal may be at least one selected from a group consisting of a computer and a portable terminal. It can be understood that, the user terminal may also be any other type of electronic devices that can receive, process, and display data, the electronic devices may include, but is not limited to, a desktop computer, a laptop, a tablet computer, a smart home appliance, a wearable device, a vehicle-mounted electronic device, a medical electronic device, etc. For example, a terminal used for the current object may be a portable terminal (e.g., a mobile phone). For example, the terminal for the individual may be a computer.

For example, specific implementation modes of the object service module, the first individual service module, the second individual service module, the organization administration module, the two-way referral module, the device administration module, the patient administration module, and the memory will be exemplarily described in conjunction with relevant examples, and no details will be repeated here.

Figure 3I:
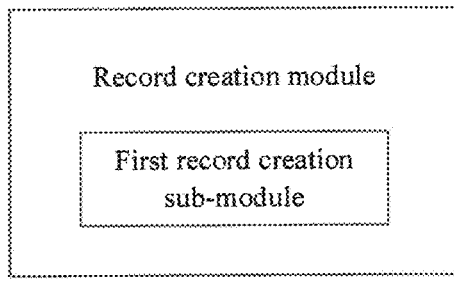
FIG. 3I shows a schematic diagram of a user administration page provided by at least one embodiment of the present disclosure.

FIG. 3I shows a schematic diagram of the user administration page provided by at least one embodiment of the present disclosure. For example, an administrator (e.g., a hospital administrator) of the health administration apparatus can see the user administration page after logging in. For example, on the user administration page, the administrator may add a newly added doctor user, modify information of a current doctor user, and delete an existing doctor user. For example, in a case where the administrator clicks on "New Doctor" on the user administration page and fills in information of the newly added doctor on a subsequent page, the user administration page provides the received information of the newly added doctor to the user administration module; and the user administration module adds a new user to the health administration system based on the received information.

For example, the health administration apparatus provided by at least one embodiment of the present disclosure may further include a device input module and a device input page. For example, the super administrator of the health administration apparatus can see the device input page after logging in. For example, the device input page and the device input module allow the super administrator to input a new device into the health administration system.

For example, the health administration apparatus provided by at least one embodiment of the present disclosure may further include a device binding module and a device binding page. For example, the hospital administrator can see the device binding page after logging in. For example, the device binding page and the device binding module allow the hospital administrator to bind a device newly allocated by the health administration system with the hospital where the hospital administrator is located.

For example, specific implementation modes of the first individual service module, the device administration module, the two-way referral module, the patient administration module, the organization administration module, the user administration module, the device input module, the device binding module, the organization administration page, the user administration page, the device input page, the device binding page, the object service module, and the second individual service module will be exemplarily described in subsequent corresponding examples, and no details will be repeated here.

Figure 4:
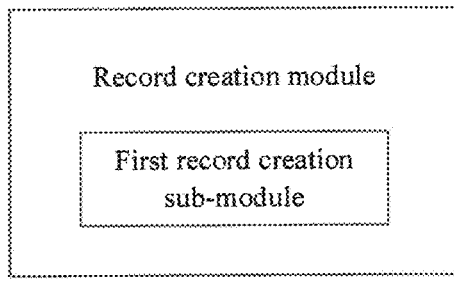
FIG. 4 is a schematic block diagram of a first example of a record creation module provided by at least one embodiment of the present disclosure.

FIG. 4 is a schematic block diagram of a first example of a record creation module provided by at least one embodiment of the present disclosure. As shown in FIG. 4, the record creation module includes a first record creation sub-module. For example, the first record creation sub-module is configured to: acquire a first identification code of a current object among a plurality of objects and an identification code of a first current device; associate identity information of the current object with latest device-related data, to generate a device usage record of the current object, and provide the device usage record of the current object to the memory associated with the health administration apparatus. For example, the first record creation sub-module is further configured to: use the identification code of the first current device to query the memory associated with the health administration apparatus, to acquire the latest device-related data originating from the first current device and transferred to the memory; and use the first identification code of the current object to query the memory, to acquire the identity information of the current object.

For example, the first identification code of the current object refers to a serial number of the current object in the object service module. For example, in a case where the object service module is implemented as a WeChat applet, the first identification code of the current object may be a serial number of the current object in the WeChat applet. For example, a label number of the current object in the WeChat applet may be a WeChat number of the current object.

For example, the first current device is a device that has been used by the current object. For example, the first current device is selected from a group consisting of a ventilator, an oxygen generator, a non-invasive multi-parameter detector, and a pulmonary function instrument.

For example, the identification code of the first current device is selected from a group consisting of a device serial number of the first current device, a platform serial number of the first current device (e.g., a serial number of the first current device in a health administration platform), and an internal number of the first current device (e.g., a serial number of the first current device in a database associated with the memory).

It should be noted that, among the plurality of devices involved in the health administration apparatus provided by at least one embodiment of the present disclosure, an identification code of a device (e.g., a second current device and a third current device described later in detail) other than the first current device may also be selected from at least one of the device serial number of the first current device, the platform serial number of the first current device, and the internal number of the first current device, and no details will be repeated here.

For example, the first record creation sub-module is configured to communicate with the object service module of the terminal for the current object, to acquire the first identification code of the current object and the identification code of the first current device from the object service module.

For example, the object service module is configured to: acquire the first identification code of the object (e.g., the object logging in the object service module, the current object) associated with the object service module and the identification code of the device used by the object associated with the object service module, and output the first identification code of the object associated with the object service module and the identification code of the device used by the object associated with the object service module.

For example, in a case where the object associated with the object service module is the current object, the object service module is configured to acquire the first identification code of the current object and the identification code of the first current device.

For example, the object service module is configured to acquire the identification code of the first current device obtained by a barcode scanner scanning a barcode of the first current device. For example, the barcode of the first current device is a two-dimensional code of the first current device. For example, the health administration apparatus further includes a device administration module; the device administration module is configured to generate the barcode of the first current device based on the identification code of the first current device. For example, the barcode of the first current device is printed and posted on the first current device for being scanned by the terminal of the object using the first current device. For example, the first identification code of the object associated with the object service module and the identification code of the device used by the object associated with the object service module output by the object service module are provided to the record creation module (e.g., the first record creation sub-module).

For example, before using the identification code of the first current device to query the memory associated with the health administration apparatus, the device-related data generated by the first current device and related to the current object has been transferred to the memory associated with the health administration apparatus; in this case, the device-related data stored in the memory is not associated with the information of the object, that is, the device-related data stored in the memory is unclaimed data or data with empty identity information.

For example, the first current device generates the device-related data, which is transferred to (e.g., directly or indirectly transferred to) the memory associated with the health administration apparatus via wired or wireless communication. For example, wired communication may be implemented by means of twisted pair, coaxial cable or optical fiber transmission, etc., for communication; and wireless communication may be implemented by means of mobile communication network (e.g., 3G/4G/5G communication network card), Bluetooth, infrared communication, General Packet Radio Service (GPRS), Zigbee or WiFi, etc. It should be noted that, among the plurality of devices involved in the health administration apparatus provided by at least one embodiment of the present disclosure, a device (e.g., the second current device and the third current device described later in detail) other than the first current device generates device-related data, which may also be transferred to (e.g., directly or indirectly transferred to) the memory associated with the health administration apparatus via wired or wireless communication.

For example, the first current device is configured to allow the device-related data generated by the first current device to be directly or indirectly transferred to the memory associated with the health administration apparatus. For example, being indirectly transferred to the memory refers to that the device-related data is transferred to other memory before being transferred to the memory associated with the health administration apparatus; and being directly transferred to the memory refers to that the device-related data is not transferred to any other memory before being transferred to the memory associated with the health administration apparatus. For example, the first current device is configured to allow the device-related data generated by the first current device to be transferred to the memory via a third-party platform. For example, the third-party platform may be the back end of a manufacturer of the device (e.g., the first current device).

It should be noted that, although the examples here and subsequent related examples are described by taking a case that the device-related data generated by the device is transferred to the memory via the third-party platform, at least one embodiment of the present disclosure is not limited thereto. For example, according to actual application needs, the device-related data generated by the device involved in the examples here and subsequent related examples may also be directly transferred to the memory without a third-party platform.

For example, the device-related data (e.g., raw data) generated by the first current device may be at least one category of detection data and usage data. For example, in a case where the first current device is a detection device, the device-related data may be physical sign data, which that is by the detection device, of an object using the detection device. For example, in a case where the first current device is a pulmonary function instrument, the device-related data may include vital capacity. For example, in a case where the first current device is a treatment device or a rehabilitation device, the device-related data may be at least one category selected from a group consisting of setting parameter data of the treatment device or the rehabilitation device and time data that the object uses the treatment device or the rehabilitation device. For example, in a case where the first current device is a ventilator, the device-related data may include at least one selected from a group consisting of ventilation frequency of the ventilator and time the object uses the ventilator. For example, the latest device-related data refers to device-related data generated by the first current device after the current object uses the first current device.

It should be noted that, among the plurality of devices involved in the health administration apparatus provided by at least one embodiment of the present disclosure, a device (e.g., the second current device and the third current device described later in detail) other than the first current device generates device-related data, which may also be at least one category of detection data and usage data, and no details will be repeated here.

For example, before the first identification code of the current object is used to query the memory, the identity information of the current object is already stored in the memory. For example, the current object may input the identity information of the current object into the object service module in the registration link before using the object service module for the first time; and the object service module supplies the acquired identity information of the current object and the first identification code of the current object to the memory, to complete registration of the current object, that is, to register the current object in the health administration apparatus.

For example, the associating the identity information of the current object with the latest device-related data includes writing the identity information of the current object into the latest device-related data with empty identity information that is generated by the first current device.

For example, the memory associated with the health administration apparatus is also configured to receive and store processed data acquired based on the latest device-related data; in this case, the object service module is further configured to acquire, from the memory, the processed data acquired based on the latest device-related data, and provide the above-described processed data to the monitor of the terminal where the object service module is located for display; correspondingly, the first individual service module is further configured to acquire, from the memory, the processed data acquired based on the latest device-related data, and supply the above-described processed data to the monitor of the terminal where the first individual service module is located for display. For example, that processed data acquired based on the latest device-related data may be generated by a data processing module of the health administration apparatus and supplied to the memory. For example, in a case where the first current device is a pulmonary function instrument, the latest device-related data includes an actual detection value of vital capacity; and the data processing module of the health administration apparatus may acquire a ratio of an actual value to a predicted value based on the predicted value of vital capacity and the actual detection value of vital capacity. For example, the above-described ratio of the actual value to the predicted value is supplied to the memory, and may be acquired by the object service module and the first individual service module. For example, by acquiring the processed data based on the latest device-related data, and supplying the processed data to the object service module and the first individual service module, the amount of information of the report displayed in the terminal where the object service module and the first individual service module are located can be increased.

It should be noted that, in other examples of the health administration apparatus provided by at least one embodiment of the present disclosure, the memory associated with the health administration apparatus is further configured to receive and store the processed data acquired based on the latest device-related data, and supply the above-described processed data to the object service module and the first individual service module, etc., and no details will be repeated here.

An application scenario of the health administration apparatus including the record creation module shown in FIG. 4 will be exemplarily described below in conjunction with a specific example.

First of all, the device administrator may print the barcode (e.g., the two-dimensional code) of the first current device generated by the device administration module and post the barcode of the first current device on the first current device. For example, after the barcode of the first current device has been posted to the first current device, there is no need to execute this operation. Secondly, a medical worker (e.g., a doctor or a nurse associated with the doctor) allocates a device to a patient with chronic disease who is currently seeking medical consultation for use. Thirdly, the patient with chronic disease who is currently seeking medical consultation uses the device, the device generates the device-related data, and the device-related data is transferred to the memory associated with the health administration apparatus; here, the device-related data stored in the memory is not associated with the patient information, that is, the device-related data stored in the memory is unclaimed data or data with empty identity information. Fourthly, having used the first current device, the patient with chronic disease may use the WeChat applet to scan the barcode; in this case, the WeChat applet may acquire the WeChat number of the patient with chronic disease and the identification code of the first current device, and output the WeChat number of the patient with chronic disease and the identification code of the first current device (e.g., the WeChat number of the patient with chronic disease and the identification code of the first current device output are associated to each other). For example, the WeChat applet may directly supply the WeChat number of the patient with chronic disease and the identification code of the first current device to the record creation module or to the first record creation sub-module via the memory. Fifthly, the first record creation sub-module uses the identification code of the first current device to query the memory associated with the health administration apparatus, to acquire the latest device-related data originating from the first current device and transferred to the memory, and uses the first identification code of the current object to query the memory, so as to acquire the identity information of the current object. Sixthly, the first record creation sub-module writes the identity information of the current object into an identity information part of the object in the latest device-related data generated by the first current device and transferred to the memory, so as to generate the device usage record of the current object, and supplies the device usage record of the current object to the memory associated with the health administration apparatus. Seventhly, the patient with chronic disease who is currently seeking medical consultation may view the device-related data (e.g., at least one selected from a group consisting of the latest device-related data and historical device-related data) through the WeChat applet; and the doctor who diagnoses and treats the patient with chronic disease who is currently seeking medical consultation may view, through the first individual service module, the device-related data of the patient with chronic disease who is currently seeking medical consultation.

Figure 5:
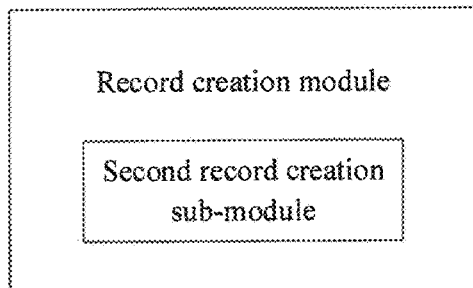
FIG. 5 is a schematic block diagram of a second example of a record creation module provided by at least one embodiment of the present disclosure.

FIG. 5 is a schematic block diagram of a second example of the record creation module provided by at least one embodiment of the present disclosure. As shown in FIG. 5, the record creation module includes a second record creation sub-module. The second record creation sub-module is configured to: acquire the first identification code of the current object among the plurality of objects and an identification code of the second current device, here the second current device being a device to be used by the current object; use the first identification code of the current object to query the memory associated with the health administration apparatus, so as to acquire the identity information of the current object, and create a correspondence relationship between the identity information of the current object and the second current device; associate the identity information of the current object with the device-related data, when a data receiver associated with the health administration apparatus receives the device-related data originating from the second current device, so as to generate the device usage record of the current object, and provides the device usage record of the current object to the memory associated with the health administration apparatus.

For example, the identification code of the second current device is selected from a group consisting of a device serial number of the second current device, a platform serial number of the second current device, and an internal number of the second current device. For example, the second current device includes a pulse oximeter or other applicable devices.

For example, the second record creation sub-module is configured to communicate with the object service module of the terminal used for the current object, so as to acquire the first identification code of the current object and the identification code of the second current device from the object service module.

For example, when the object associated with the object service module is the current object, the object service module is configured to acquire the first identification code of the current object and the identification code of the second current device.

For example, the object service module is configured to acquire the identification code of the second current device obtained by scanning a barcode of the second current device via a barcode scanner. For example, the barcode of the second current device is a two-dimensional code of the second current device. For example, the health administration apparatus further includes a device administration module; the device administration module is configured to generate the barcode of the second current device based on the identification code of the second current device. For example, the barcode of the second current device is printed and posted on the second current device, for being scanned by the terminal of the object using the second current device.

For example, the creating a correspondence relationship between the identity information of the current object and the second current device includes creating data that has the identity information of the current object and the identification code of the second current device but leaves the device-related data of the second current device empty.

For example, the second current device generates the device-related data, which is transferred to the health administration apparatus via wired or wireless communication, and is received by the data receiver associated with the health administration apparatus.

For example, the second current device is configured to allow the device-related data generated by the second current device to be directly or indirectly transferred to the data receiver associated with the health administration apparatus. For example, being indirectly transferred to the data receiver associated with the health administration apparatus refers to that the device-related data is transferred to other memory before being transferred to the data receiver associated with the health administration apparatus; and being directly transferred to the data receiver associated with the health administration apparatus refers to that the device-related data is not transferred to any other memory before being transferred to the data receiver associated with the health administration apparatus.

For example, the second current device is configured to allow the device-related data generated by the second current device to be directly transferred to the data receiver associated with the health administration apparatus via a communication module (e.g., a Bluetooth gateway).

For example, the device-related data (e.g., raw data) generated by the second current device may be at least one category of detection data and usage data. For example, in a case where the second current device is a pulse oximeter, the device-related data may include blood oxygen saturation detected by the pulse oximeter.

For example, the associating the identity information of the current object with the device-related data when the data receiver associated with the health administration apparatus receives the device-related data originating from the second current device includes: writing the device-related data originating from the second current device and received by the data receiver into the above-described data in which the device-related data is empty. For example, after the second current device is associated with the current object, and before the second current device is associated with other object other than the current object, the device-related data generated by the second current device is associated with the identity information of the current object.

An application scenario of the health administration apparatus including the record creation module shown in FIG. 5 will be exemplarily described below in conjunction with a specific example.

First of all, the device administrator may print the barcode (e.g., the two-dimensional code) of the second current device generated by the device administration module and post the barcode of the second current device to the second current device. For example, after the barcode of the second current device has been posted to the second current device, there is no need to execute this operation. Secondly, a medical worker (e.g., a doctor or a nurse associated with the doctor) rents a device to a patient with chronic disease who is currently seeking medical consultation for use. Thirdly, the patient with chronic disease who is currently seeking medical consultation uses the WeChat applet to scan the barcode of the second current device; the WeChat applet used by the patient with chronic disease who is currently seeking medical consultation may acquire the WeChat number of the patient with chronic disease who is currently seeking medical consultation and the identification code of the second current device, and provides the WeChat number of the patient with chronic disease who is currently seeking medical consultation and the identification code of the second current device to the second record creation sub-module; correspondingly, the second record creation sub-module creates data that has the WeChat number of the patient with chronic disease who is currently seeking medical consultation and the identification code of the second current device but leaves the device-related data of the second current device empty. Fourthly, the patient with chronic disease who is currently seeking medical consultation uses the rented device (e.g., uses in the home of the patient with chronic disease who is currently seeking medical consultation), and the rented device generates the device-related data and stores the device-related data in the memory of the rented device. Fifthly, the patient with chronic disease returns the rented device to the medical worker (e.g., the doctor, or the nurse or the device administrator associated with the doctor), the medical worker opens the device rented and returned by the patient with chronic disease who is currently seeking medical consultation, and the device-related data stored in the device rented and returned by the patient with chronic disease who is currently seeking medical consultation is transferred to the data receiver associated with the health administration apparatus via the Bluetooth gateway (i.e., a device that integrates two wireless communication modes of Bluetooth and WIFI). Sixthly, when the data receiver associated with the health administration apparatus receives the device-related data originating from the device rented and returned by the patient with chronic disease who is currently seeking medical consultation, the second record creation sub-module associates the identity information of the patient with chronic disease who is currently seeking medical consultation with the device-related data, so as to generate the device usage record of the patient with chronic disease who is currently seeking medical consultation, and supplies the device usage record of the patient with chronic disease who is currently seeking medical consultation to the memory associated with the health administration apparatus. Seventhly, the patient with chronic disease who is currently seeking medical consultation may view the device-related data (e.g., at least one category of the device-related data uploaded this time and historical device-related data) through the WeChat applet; and the doctor who diagnoses and treats the patient with chronic disease who is currently seeking medical consultation may view, through the first individual service module, the device-related data of the patient with chronic disease who is currently seeking medical consultation.

Figure 6:
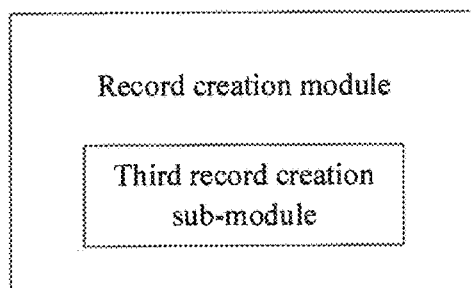
FIG. 6 is a schematic block diagram of a third example of a record creation module provided by at least one embodiment of the present disclosure.

FIG. 6 is a schematic block diagram of a third example of the record creation module provided by at least one embodiment of the present disclosure. As shown in FIG. 6, the record creation module includes a third record creation sub-module. The third record creation sub-module is configured to: provides unassociated data of at least one device of the plurality of devices, here summary information of the unassociated data (e.g., at least one selected from a group consisting of record generation time, device name, and device serial number) being configured to be displayed in a terminal for an individual where the first individual service module is located; communicate with the first individual service module to receive, from the first individual service module (e.g., the in-hospital data page of the first individual service module), the second identification code of the object corresponding to the unassociated data; associate the object corresponding to the unassociated data with the unassociated data, so as to generate a device usage record of the object corresponding to the unassociated data; and provide the device usage record of the object corresponding to the unassociated data to the memory associated with the health administration apparatus.

For example, in a case where an association relationship between the object and the device used by the object is not established before the object uses the device, the device-related data transferred to the health administration apparatus is data with empty identity information; in this case, if the object does not claim (e.g., by scanning the two-dimensional code of the device) the above-described data with empty identity information after using the device, the above-described data with empty identity information will be marked as the unassociated data of the device and stored in the memory. For example, the third record creation sub-module may acquire the unassociated data of at least one device among the plurality of devices from the memory, and supply the above-described unassociated data to the first individual service module (e.g., the in-hospital data page of the first individual service module); and the unassociated data is configured to be displayed in the terminal for the individual where the first individual service module is located.

For example, the first individual service module may receive the second identification code of the object corresponding to the unassociated data (e.g., the object's mobile phone number), and supply the second identification code of the object corresponding to the above-described unassociated data to the third record creation sub-module.

For example, the associating the object corresponding to the unassociated data with the unassociated data includes: using the second identification code of the object corresponding to the unassociated data to query the memory associated with the health administration apparatus, so as to acquire the identity information of the object corresponding to the unassociated data; and associating the identity information of the object corresponding to the unassociated data with the unassociated data.

For example, the first individual service module is further configured to create a correspondence relationship between the second identification code of the object corresponding to the unassociated data and the identification code of the unassociated data, and supply the above-described correspondence to the third record creation sub-module; correspondingly, the associating, by the third record creation sub-module, the object corresponding to the unassociated data with the unassociated data, includes: using, by the third record creation sub-module, the identification code of the unassociated data to query the memory associated with the health administration apparatus to acquire the unassociated data; and filling the identity information of the object corresponding to the unassociated data into an identity information part of the unassociated data (i.e., the data with empty identity information).

For example, the identity information and the basic information (e.g., mobile phone number) of the object may be supplied by the object in the registration link before using the object service module for the first time.

An application scenario of the health administration apparatus including the record creation module shown in FIG. 6 will be exemplarily described below in conjunction with FIG. 7 and a specific example. FIG. 7 shows a schematic diagram of an "in-hospital data" page of the first individual service module provided by at least one embodiment of the present disclosure. For example, the third record creation sub-module may acquire unassociated data of at least one device among the plurality of devices from the memory, and supply the above-described unassociated data to the "in-hospital data" page of the first individual service module. For example, a medical worker (e.g., a doctor, or a nurse or a device administrator associated with the doctor) may search to find the unassociated data that meets a specified search condition, and click on "Assign Patient" on the "in-hospital data" page to enter a "Assign Patient" page, and input the mobile phone number of the patient corresponding to the unassociated data on the "Assign Patient" page; the first individual service module may supply the identification code of the acquired unassociated data and the mobile phone number of the patient corresponding to the unassociated data to the third record creation sub-module (e.g., the identification code of the unassociated data and the mobile phone number of the patient corresponding to the unassociated data received by the third record creation sub-module are associated with each other); the third record creation sub-module is configured to use the second identification code of the object corresponding to the unassociated data to query the memory associated with the health administration apparatus, so as to acquire the identity information of the object corresponding to the unassociated data; use the identification code of the unassociated data to query the memory, so as to acquire the unassociated data; and fill the identity information of the object corresponding to the unassociated data into the identity information part of the unassociated data (i.e., the data with empty identity information).

FIG. 8 is an exemplary block diagram of a fourth example of the record creation module provided by at least one embodiment of the present disclosure. As shown in FIG. 8, the record creation module includes a fourth record creation sub-module. The fourth record creation sub-module is configured to: receive the identity information of the current object among the plurality of objects and device-related data generated by the third current device and associated with the identity information of the current object, here the third current device being a device that has been used by the current object; generate a device usage record of the current object at least based on the identity information of the current object and the device-related data associated with the identity information of the current object and generated by the third current device; and provide the device usage record of the current object to the memory associated with the health administration apparatus.

For example, the third current device may include at least one category selected from a group consisting of a detection device (e.g., respiratory screening instruments or pulmonary function instruments) and a treatment device (e.g., oxygen generators). For example, the third current device may be a respiratory screening instrument; and the respiratory screening instrument is configured to collect respiratory-related physical sign information data of the current object. For example, the respiratory screening instrument monitors breathing data of deep inhalation and forced exhalation of the patient currently seeking medical consultation, to determine whether the patient currently seeking medical consultation has symptoms such as Obstructive Sleep Apnea Syndrome (OSAS) in a sleep process, and to further determine whether the patient currently seeking medical consultation has respiratory disease of lungs. For example, a fourth example shown in FIG. 8 will be exemplarily described below by taking a case of implementing the third current device as a respiratory screening instrument as an example, but the embodiments of the present disclosure are not limited thereto. It should be noted that, for convenience of description, in the fourth example and related examples, the respiratory screening instrument is also described as a pulmonary function instrument; those skilled in the art can understand that, both the respiratory screening instrument and the pulmonary function instrument are instruments used to detect whether the patient currently seeking medical consultation suffers from respiratory disease of the lungs.

For example, by enabling the fourth record creation sub-module to receive (e.g., acquire from the second individual service module described later in detail) the identity information of the current object among the plurality of objects and the device-related data generated by the third current device and associated with the identity information of the current object, the fourth record creation sub-module may be allowed to generate the device usage record of the current object based on the identity information of the current object and the device-related data that are related to each other, which, thus, can improve work efficiency of medical workers and reduce the amount of data processed by the record creation module.

For example, the fourth record creation sub-module is configured to communicate with the second individual service module, to acquire, from the second individual service module, the identity information of the current object among the plurality of objects and the device-related data generated by the third current device and associated with the identity information of the current object.

For example, the second individual service module is used in an object identity information data acquisition terminal. For example, the object identity information data acquisition terminal is configured to acquire the identity information of the current object among the plurality of objects, and supply the identity information of the current object to the second individual service module.

For example, the object identity information data acquisition terminal is configured to read identity information (e.g., identity card number and name) contained in an identity document (e.g., an identity card or a passport) of the current object. For example, the object identity information data acquisition terminal may be implemented as a Point Of Sales (POS) machine. For example, the above-described POS machine may read the identity information contained in the identity card of the current object.

For example, the second individual service module may be an APP and an applet. For example, in a case where the second individual service module is implemented as an APP, the object identity information data acquisition terminal may download the above-described APP from the application market and install the above-described APP.

FIG. 9A is a schematic diagram of a graphical user interface of the second individual service module provided by at least one embodiment of the present disclosure. For example, as shown in FIG. 9A, the second individual service module may be a pulmonary function screening module of a respiratory rehabilitation service APP (i.e., respiratory rehabilitation service application software). For example, in a case where the third current device is a respiratory screening instrument, one may click on "Pulmonary Function Screening" of the respiratory rehabilitation service APP shown in FIG. 9A, and enter the pulmonary function screening module.

For example, the third current device is configured to be associated (e.g., bound) with the object identity information data acquisition terminal; in this case, by using the object identity information data acquisition terminal to acquire the identity information of the current object, the identity information of the current object and the identification code of the third current device may be associated with each other; and therefore, when the current object uses the third current device, the device-related data generated by the third current device may be automatically associated with the identity information of the current object, thereby reducing workload of the medical workers.

For example, the second individual service module is further configured to acquire (e.g., acquire from the graphical user interface of the second individual service module) the identification code (e.g., the serial number) of the third current device, so as to bind the object identity information data acquisition terminal (e.g., the identification code of the object identity information data acquisition terminal) to the third current device. For example, the identification code of the object identity information data acquisition terminal may be a serial number of the object identity information data acquisition terminal.

For example, a medical worker may input the identification code of the third current device on the graphical user interface of the second individual service module; and the second individual service module may acquire the identification code of the third current device from the graphical user interface of the second individual service module, and associate the object identity information data acquisition terminal with the third current device.

For example, the second individual service module is further configured to acquire information (e.g., an identification code of an individual) of an individual (e.g., a medical worker), so as to bind the individual with the object identity information data acquisition terminal (e.g., the identification code of the object identity information data acquisition terminal). For example, the identification code of the individual may be selected from a mobile phone number, a work number, and an identity card number of the individual.

For example, after the individual is bound to the object identity information data acquisition terminal, the second individual service module may establish an association (e.g., binding) relationship between the individual and the object (e.g., the current object) associated with the identity information collected by the object identity information data acquisition terminal), and supply the above-described binding relationship between the individual and the object to the health administration apparatus, whereby, the individual may view related information of the object associated with the identity information collected by the object identity information data acquisition terminal used by the individual, and provide diagnosis-and-treatment service for the above-described object.

For example, the individual may input the information of the individual (e.g., the mobile phone number of the individual) on the graphical user interface of the second individual service module; and the second individual service module may allow a mobile phone verification code generation module to send a mobile phone verification code to the mobile phone of the individual; after the individual inputs the mobile phone verification code received by the mobile phone of the individual on the graphical user interface of the second individual service module, the second individual service module associates the individual (e.g., the mobile phone number of the individual) with the object identity information data acquisition terminal.

For example, the second individual service module is further configured to acquire the basic information of the individual from the memory associated with the health administration apparatus based on the identification code of the individual, and display the basic information on an individual information display interface of the second individual service module. For example, the basic information of the individual includes name, gender, and email address of the individual, and a hospital to which the individual belongs.

For example, at any time, each object identity information data acquisition terminal is only bound to one corresponding third current device, and each object identity information data acquisition terminal is only bound to one corresponding individual; in this case, each third current device is only bound to one corresponding individual, and device-related data generated by each third current device may only be viewed by the individual bound to the above-described third current device and a superior administrator of the individual, so that information security of the object using the third current device can be improved.

How to establish the association relationship between the individual and the object identity information data acquisition terminal, how to establish the association relationship between the third current device and the object identity information data acquisition terminal, and how to acquire the identity information and the basic information of the current object will be exemplarily described below in conjunction with FIG. 9B, FIG. 10A, FIG. 10B, FIG. 11A, and FIG. 11B. Hereinafter, exemplary description will be given by taking a case of respectively implementing the third current device, the second service module, and the object identity information data acquisition terminal as a respiratory screening instrument, a pulmonary function screening module of a respiratory rehabilitation service APP, and a POS machine as an example; however, the embodiments of the present disclosure are not limited thereto.

For example, the medical worker may be associated with the POS machine through a doctor login link; the respiratory screening instrument may be associated with the POS machine and associated with the medical worker through a device binding link; a virtual identification code of the respiratory screening instrument may be created through a data initialization operation; and the virtual identification code of the respiratory screening instrument is bounded with the identification code of the respiratory screening instrument.

Figure 9B:
FIG. 9B is a step guide page of the second individual service module shown in FIG. 9A.
Figure 9B:

FIG. 9B is a step guide page of the second individual service module shown in FIG. 9A. For example, when the POS machine and the respiratory rehabilitation service APP are used for the first time, when clicking on "Pulmonary Function Screening" of the respiratory rehabilitation service APP shown in FIG. 9A, one will enter the step guide page shown in FIG. 9B. For example, as shown in FIG. 9B, a doctor login operation, a device binding operation, and a data initialization operation will be performed in sequence.

For example, the medical worker may be associated with the POS machine through the doctor login link; the respiratory screening instrument may be associated with the POS machine and associated with the medical worker through the device binding link; the virtual identification code of the respiratory screening instrument may be created through the data initialization operation; and the virtual identification code of the respiratory screening instrument is bounded with the identification code of the respiratory screening instrument.

Figure 10A:
FIG. 10A shows an individual information input interface of the second individual service module shown in FIG. 9A.
Figure 10A:
Figure 10B:
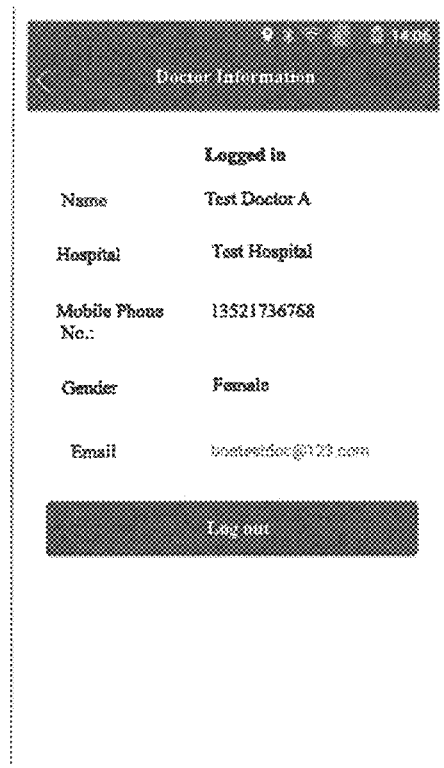
FIG. 10B shows an individual information display interface of the second individual service module shown in FIG. 9A.

FIG. 10A shows an individual information input interface of the second individual service module shown in FIG. 9A (e.g., a login interface of the pulmonary function screening module of the respiratory rehabilitation service APP); and FIG. 10B shows an individual information display interface of the second individual service module shown in FIG. 9A.

For example, as shown in FIG. 10A, the medical worker may input the mobile phone number of the medical worker on the graphical user interface of the pulmonary function screening module of the respiratory rehabilitation service APP; and the pulmonary function screening module of the respiratory rehabilitation service APP may allow the mobile phone verification code generation module to send a mobile phone verification code to the mobile phone of the medical worker; after the medical worker inputs the mobile phone verification code received by the mobile phone of the medical worker on the graphical user interface of the pulmonary function screening module of the respiratory rehabilitation service APP, the pulmonary function screening module of the respiratory rehabilitation service APP associates the medical worker (e.g., the mobile phone number of the medical worker) with the POS machine (e.g., the serial number of the POS machine); at this time, the medical worker successfully logs in to the pulmonary function screening module of the respiratory rehabilitation service APP.

For example, after the mobile phone verification code received by the mobile phone of the medical worker is input on the graphical user interface of the pulmonary function screening module of the respiratory rehabilitation service APP, the pulmonary function screening module of the respiratory rehabilitation service APP will provide the mobile phone number of the medical worker to the health administration apparatus, so as to acquire the basic information of the medical worker from the health administration apparatus, and the basic information of the medical worker is displayed on the graphical user interface shown in FIG. 10B.

For example, at any time, the pulmonary function screening module of the respiratory rehabilitation service APP allows only one medical worker to log in; if other medical worker wants to log in to the pulmonary function screening module located in the specified POS machine, he/she can log in only after the medical worker who currently logs in logs out. For example, the medical worker may click on "Logout" on the graphical user interface shown in FIG. 10B to release the binding relationship with the POS machine.

For example, after a medical worker successfully logs in to the pulmonary function screening module of the respiratory rehabilitation service APP, the medical worker may perform at least one of operations such as respiratory screening instrument binding, patient binding, and using the respiratory screening instrument to detect the patient. It should be noted that, in a case where the POS machine is bound to the respiratory screening instrument, after the medical worker successfully logs in to the pulmonary function screening module of the respiratory rehabilitation service APP, the medical worker may directly perform operations such as patient binding (e.g., patient information entry) and using the respiratory screening instrument to detect the patient, without performing operations of respiratory screening instrument binding and doctor login.

Figure 11A:
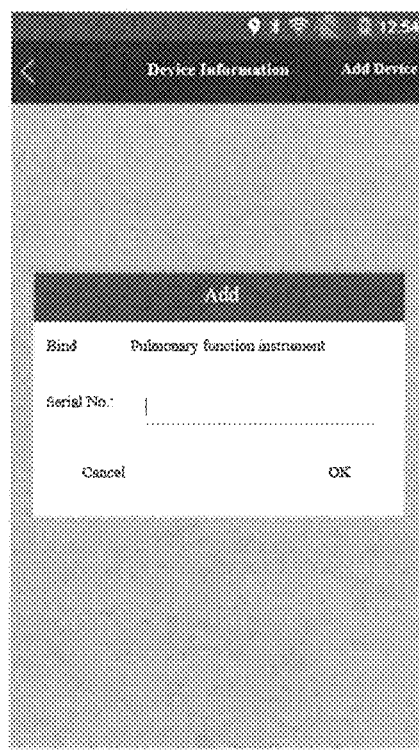
FIG. 11A shows an identification code input interface of a third current device of the second individual service module shown in FIG. 9A.
Figure 11B:
FIG. 11B shows an identification code display and edit page of the third current device of the second individual service module.

FIG. 11A shows an identification code input interface of the third current device of the second individual service module shown in FIG. 9A; and FIG. 11B shows an identification code display and edit page of the third current device of the second individual service module. For example, as shown in FIG. 11A, the medical worker may input a serial number of the respiratory screening instrument on the graphical user interface of the pulmonary function screening module of the respiratory rehabilitation service APP (e.g., an input interface for inputting the serial number of the respiratory screening instrument); the pulmonary function screening module of the respiratory rehabilitation service APP may acquire the serial number of the respiratory screening instrument from the graphical user interface of the pulmonary function screening module of the respiratory rehabilitation service APP, and associate the POS machine (e.g., the serial number of the POS machine) with the respiratory screening instrument (e.g., the serial number of the respiratory screening instrument).

For example, as shown in FIG. 11B, the pulmonary function screening module of the respiratory rehabilitation service APP may also display the serial number of the respiratory screening instrument on a serial number display and edit page of the respiratory screening instrument. For example, the serial number display and edit page of the respiratory screening instrument also allows the medical worker to modify the serial number of the respiratory screening instrument bound to the POS machine and perform an unbinding operation (remove the binding relationship with the POS machine).

For example, after the serial number of the respiratory screening instrument is entered successfully, the respiratory rehabilitation service APP will perform data initialization. For example, the respiratory rehabilitation service APP calls a virtual user registration interface of a back-end system of a manufacturer of the respiratory screening instrument, acquires an identification code (ID) of a virtual user, and uses a device binding interface of the back-end system of the manufacturer of the respiratory screening instrument to bind the above-described ID of the virtual user with the serial number of the respiratory screening instrument, so that a binding relationship between the ID of the virtual user and the respiratory screening instrument may be established. For example, after the binding relationship between the ID of the virtual user and the respiratory screening instrument is established, if it is necessary to acquire data generated by the respiratory screening instrument from the back-end system of the manufacturer of the respiratory screening instrument, the above-described ID of the virtual user bound with the serial number of the respiratory screening instrument may be used as a query condition. For example, after the binding relationship between the ID of the virtual user and the respiratory screening instrument is established, the respiratory rehabilitation service APP may call a device binding interface (a device binding module) of the health administration apparatus to bind the ID of the virtual user with the serial number of the respiratory screening instrument and the serial number of the POS machine; in this case, the POS machines are in one-to-one correspondence with the respiratory screening instruments, and the POS machines are in one-to-one correspondence with the IDs of the virtual user corresponding to the respiratory screening instruments; so far, the initialization is completed. It should be noted that, when the device-related data generated by the third current device is transferred to the health administration apparatus not via the third-party platform, the data initialization operation may not be included.

For example, the second individual service module is configured to acquire the identity information and the basic information of the current object. For example, the method for acquiring the identity information and the basic information of the current object by the second individual service module will be exemplarily described below in conjunction with FIG. 12A and FIG. 12B.

Figure 12A:
FIG. 12A shows a schematic diagram of an object information input interface of the second individual service module shown in FIG. 9A.

FIG. 12A shows a schematic diagram of an object information input interface (e.g., a patient personal information input interface) of the second individual service module shown in FIG. 9A.

In one example, the second individual service module may acquire the identity information of the current object from the object identity information data acquisition terminal. For example, the identity document of the current object may be placed on an information reading module of the object identity information data acquisition terminal, to allow the object identity information data acquisition terminal to read the identity information of the current object contained in the identity document of the current object. For example, the identity information of the current object includes name and the identity card number of the current object. For example, the identity information of the current object read by the object identity information data acquisition terminal is supplied to the second individual service module and automatically filled in the object information input interface of the second individual service module shown in FIG. 12A. In another example, the individual may manually input the identity information of the current object into the object information input interface of the second individual service module.

For example, the second individual service module is further configured to: acquire, based on the identity information of the current object, a query result supplied by the health administration apparatus as to whether the current object exists in the memory; if the query result is that the current object exists in the memory, acquire the basic information of the current object from the memory; if the query result is that the current object does not exist in the memory, acquire (e.g., acquire the information input by the individual from the object information input interface of the second individual service module) the basic information of the current object, and supply the basic information and the identity information of the current object to the memory, to complete registration of the current object. For example, the basic information of the current object is selected from a mobile phone number, gender, height, weight, and age of the current object.

For example, after the second individual service module acquires the identity information of the current object, "Query" (e.g., "Query" on a right side of identity card number or name) in the object information input interface shown in FIG. 12A may be clicked to cause the second individual service module to send a query request to the health administration apparatus, and to acquire the query result as to whether the current object exists in the memory. For example, if the query result is that the current object exists in the memory, the second individual service module sends a basic information acquisition request to the health administration apparatus, so as to acquire the basic information of the current object from the memory, and automatically fill the basic information of the current object into the object information input interface of the second individual service module shown FIG. 12A; and if the query result is that the current object does not exist in the memory, the second individual service module receives the basic information of the current object input by the individual on the object information input interface of the second individual service module, and supplies the basic information and the identity information of the current object to the health administration apparatus, so as to complete registration of the current object.

Figures 12B, 12C:
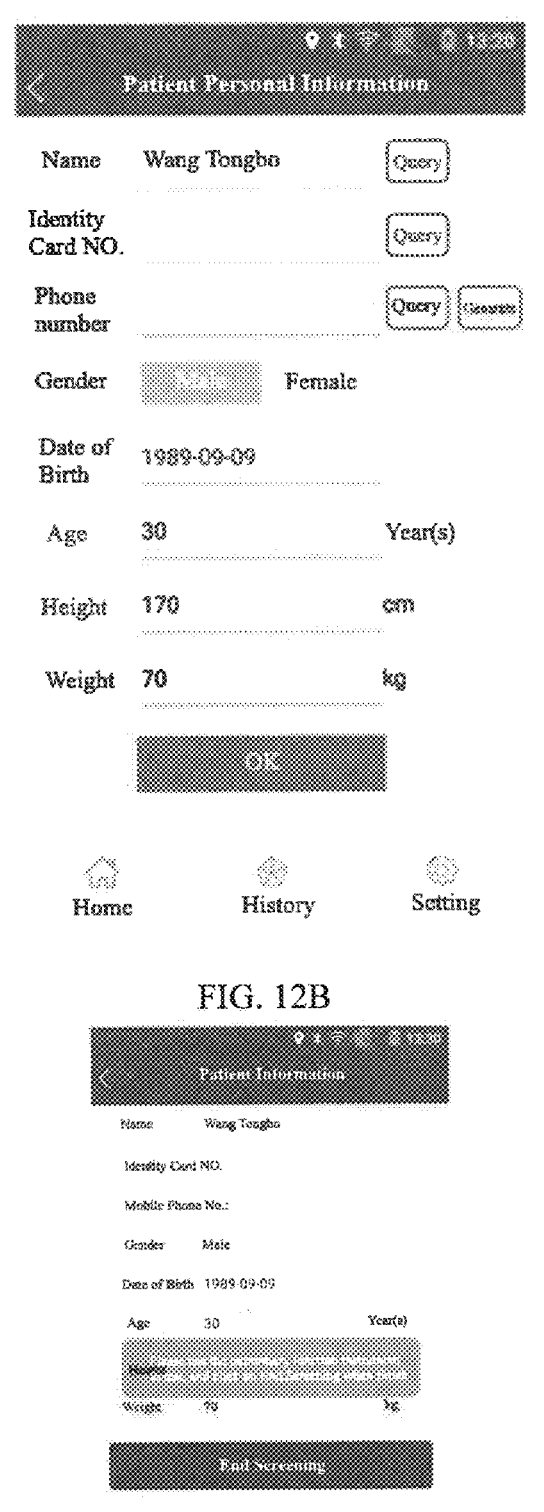

FIG. 12B shows a schematic diagram of an object information confirmation interface (e.g., patient personal information confirmation interface) of the second individual service module shown in FIG. 9A. For example, in a case where the basic information and the identity information of the current object in the object information confirmation interface of the second individual service module shown in FIG. 12B are both confirmed to be correct, "OK" may be clicked, and the second individual service module will enter a third current device usage page (a respiratory screening page). For example, after "OK" is clicked, in the case where the above-described query result is that the current object does not exist in the memory, the second individual service module supplies the basic information and the identity information of the current object to the health administration apparatus, so as to complete registration of the current object.

FIG. 12C shows a schematic diagram of a third current device usage page (a respiration screening page) of the second individual service module shown in FIG. 9A. For example, after entering the third current device usage page (the respiratory screening page), a module of a terminal where the second individual service module is located displays a prompt sentence "Please use the pulmonary function instrument to test, and click on End Screening when finish." For example, after entering the third current device usage page (the respiratory screening page), a sound playing module (e.g., a speaker) of the terminal where the second individual service module is located may inform the current object about a use method of the third current device by voice.

For example, the second individual service module is configured to acquire, based on the identification code of the third current device, the device-related data generated by the third current device and corresponding to the identity information of the current object, associate the device-related data and the identity information of the current object with each other, and provide the device-related data and the identity information of the current object associated with each other to the fourth record creation sub-module.

In one example, the device-related data generated by the third current device is transferred to the third-party platform (e.g., the back end of the manufacturer of the third current device); and in this case, the second individual service module acquires and device-related data corresponding to the identity information of the current object from the third-party platform.

In another example, the device-related data generated by the third current device is transferred to the memory associated with the health administration platform; and in this case, the second individual service module acquires the device-related data corresponding to the identity information of the current object from the memory associated with the health administration platform.

For example, the second individual service module is further configured to provide at least a portion of the basic information of the current object to the third-party platform, and acquire a predicted value of physical sign information of the current object from the third-party platform. For another example, the second individual service module is further configured to provide at least a portion of the basic information of the current object to the health administration apparatus, and acquire the predicted value of the physical sign information of the current object from the health administration apparatus. For example, gender, height, weight, and age of the current object may be provided to the third-party platform or the health administration apparatus.

For example, the second individual service module is further configured to generate a report of the current object, at least based on the device-related data generated by the third current device and corresponding to the identity information of the current object, and provide the report of the current object to the object identity information data acquisition terminal.

For example, the object identity information data acquisition terminal includes a monitor and a printer; the monitor is configured to display a report of the current object generated at least based on the device-related data; and the printer is configured to print the report of the current object generated at least based on the device-related data.

Figures 12D, 12E:
FIG. 12D shows a schematic diagram of a report display and print page of the second individual service module shown in FIG. 9A.
FIG. 12E is a schematic diagram of a report of a current object displayed on a monitor of a terminal where the object service module is located provided by at least one embodiment of the present disclosure.

FIG. 12D shows a schematic diagram of a report display and print page of the second individual service module shown in FIG. 9A; the second individual service module may fill the device-related data generated by the third current device and corresponding to the identity information of the current object into the report display and print page of the second individual service module, so as to generate the report of the current object; the report of the current object is supplied to the object identity information data acquisition terminal and displayed on the monitor of the object identity information data acquisition terminal. For example, the individual may click on "Print" on the report display and print page shown in FIG. 12D to send a print request; and the second individual service module supplies the above-described print request to the printer of the object identity information data acquisition terminal, so that the printer of the object identity information data acquisition terminal prints the report displayed on the report display and print page as shown in FIG. 12D onto a paper.

For example, the object service module (e.g., the WeChat applet) is configured to communicate with the memory associated with the health administration apparatus, to acquire the device usage record of the current object from the memory, and provide the device usage record of the current object to the monitor of the terminal where the object service module is located, so as to display the device usage record on the terminal where the object service module is located. For example, the object service module may organize the above-described device-related data into a report form and then display, to facilitate the current object to view. FIG. 12E is a schematic diagram of the report of the current object displayed on the monitor of the terminal where the object service module is located provided by at least one embodiment of the present disclosure.

For example, the first individual service module is configured to communicate with the memory associated with the health administration apparatus, so as to acquire, from the memory, the device usage record of the object associated with the individual, and provide the device usage record of the object associated with the individual to the monitor of the terminal where the first individual service module is located, so as to display the device usage record on the terminal where the first individual service module is located. For example, the first individual service module may organize the above-described device-related data into a report form and then display, so as to facilitate the first individual service module to view. FIG. 12F is the report of the object associated with the individual and displayed on the monitor of the terminal where the object associated with the individual is located provided by at least one embodiment of the present disclosure.

FIG. 13 is a schematic block diagram of a fifth example of the record creation module provided by at least one embodiment of the present disclosure. As shown in FIG. 13, the record creation module includes a fifth record creation sub-module; the fifth record creation sub-module is configured to acquire the second identification code of the current object among the plurality of objects and the identification code of the fourth current device (e.g., the second identification code of the current object and the identification code of the fourth current device received by the fifth record creation sub-module are associated with each other), here the fourth current device being a device to be used by the current object; use the second identification code of the current object to query the memory associated with the health administration apparatus, so as to acquire the identity information of the current object, and create a correspondence relationship between the identity information of the current object and the fourth current device; associate the identity information of the current object with the device-related data, when the data receiver associated with the health administration apparatus receives the device-related data originating from the fourth current device, so as to generate a device usage record of the current object; and provide the device usage record of the current object to the memory associated with the health administration apparatus.

For example, the health administration apparatus further includes a first individual service module used in the terminal of the individual. The monitor of the terminal where the first individual service module is located is configured to display a list of currently unused devices; the first individual service module is configured to select at least one device among the currently unused devices as the fourth current device, acquire the second identification code of the current object, associate the second identification code of the current object with the identification code of the fourth current device, and provide the second identification code of the current object and the identification code of the fourth current device to the fifth record creation sub-module.

An application scenario of the health administration apparatus including the record creation module shown in FIG. 13 will be exemplarily described below in conjunction with a specific example.

First, when the patient currently seeking medical consultation seeks medical consultation, the medical worker uses the first individual service module to view the list of currently unused devices. For example, the first individual service module queries the memory, to acquire the list of currently unused devices from the memory; and the monitor of the terminal where the first individual service module is located is configured to display the list of the currently unused devices.

Secondly, the medical worker allocates an unused device to the patient currently seeking medical consultation for use. For example, the medical worker inputs the mobile phone number of the patient currently seeking medical consultation in a patient information input box corresponding to the selected device. Correspondingly, the first individual service module takes the above-described selected unused device as the fourth current device, acquires the mobile phone number of the patient currently seeking medical consultation, and associates (e.g., binds) the mobile phone number of the patient currently seeking medical consultation with the identification code of the fourth current device.

Thirdly, the first individual service module supplies the mobile phone number of the patient currently seeking medical consultation and the identification code of the fourth current device that are associated with each other to the fifth record creation sub-module.

Fourthly, the fifth record creation sub-module uses the mobile phone number of the patient with chronic disease who is currently seeking medical consultation to query the memory associated with the health administration apparatus, so as to acquire the identity information of the current object, and creates data that has the identity information of the patient with chronic disease who is currently seeking medical consultation and the identification code of the fourth current device but leaves the device-related data of the fourth current device empty.

Sixthly, the patient with chronic disease who is currently seeking medical consultation uses the device allocated to the patient with chronic disease who is currently seeking medical consultation; the device allocated to the patient with chronic disease who is currently seeking medical consultation generates the device-related data; and the above-described device-related data is transferred (e.g., directly or indirectly transferred) to the data receiver associated with the health administration apparatus.

Seventhly, when the data receiver associated with the health administration apparatus receives the device-related data generated by the device allocated to the patient with chronic disease who is currently seeking medical consultation, the identity information of the patient with chronic disease who is currently seeking medical consultation is associated with the device-related data, so as to generate the device usage record of the patient with chronic disease who is currently seeking medical consultation, and supply the device usage record of the patient with chronic disease who is currently seeking medical consultation to the memory associated with the health administration apparatus.

Eighthly, the patient with chronic disease who is currently seeking medical consultation may view the device-related data (e.g., at least one category of the device-related data uploaded this time and historical device-related data) through the WeChat applet; and the doctor who diagnoses and treats the patient with chronic disease who is currently seeking medical consultation may view, through the first individual service module, the device-related data of the patient with chronic disease who is currently seeking medical consultation.

It should be noted that, the health administration apparatus provided by at least one embodiment of the present disclosure is not limited to only include one selected from a group consisting of the first record creation sub-module, the second record creation sub-module, the third record creation sub-module, the fourth record creation sub-module, and the fifth record creation sub-module; according to actual needs, the health administration apparatus provided by at least one embodiment of the present disclosure may further include any combination of the first record creation sub-module, the second record creation sub-module, the third record creation sub-module, the fourth record creation sub-module, and the fifth record creation sub-module. An exemplary description will be given below in conjunction with FIG. 14 and FIG. 15.

FIG. 14 is a schematic block diagram of a sixth example of the record creation module provided by at least one embodiment of the present disclosure. As shown in FIG. 14, the record creation module includes a first record creation sub-module, a second record creation sub-module, a third record creation sub-module, and a fourth record creation sub-module. For example, by making the record creation module include the first record creation sub-module, the second record creation sub-module, the third record creation sub-module, and the fourth record creation sub-module, the health administration apparatus shown in FIG. 1 may be allowed to administrate more types of devices.

FIG. 15 is a schematic block diagram of a seventh example of the record creation module provided by at least one embodiment of the present disclosure. As shown in FIG. 15, the record creation module includes a first record creation sub-module, a second record creation sub-module, a third record creation sub-module, a fourth record creation sub-module, and a fifth record creation sub-module. For example, by making the record creation module include the first record creation sub-module, the second record creation sub-module, the third record creation sub-module, the fourth record creation sub-module, and the fifth record creation sub-module, the health administration apparatus shown in FIG. 1 may be allowed to administrate more types of devices.

FIG. 16 is an exemplary block diagram of another health administration apparatus provided by at least one embodiment of the present disclosure.

For example, as shown in FIG. 16, the health administration apparatus further includes an organization administration module. The organization administration module is configured to grade a plurality of members belonging to the organization, and enable a member of an $N^{th}$-level in the organization to have an authority to acquire data of a member of an $M^{th}$ level in the organization, N being a positive integer greater than 1, and M being a positive integer greater than or equal to 1 and less than N.

FIG. 17 is a schematic diagram of a front-end page associated with the organization administration module provided by at least one embodiment of the present disclosure. For example, as shown in FIG. 17, the above-described organization may be a medical consortium; and the above-described plurality of members may be a plurality of members (e.g., hospitals) that are subordinate to the medical consortium. For example, when a member is newly added into the medical consortium, a level of the newly added member and a relationship between the newly added member and an original member may be entered, in this case, the organization administration module may acquire levels and affiliation of the plurality of members belonging to the medical consortium, whereby the organization administration module may group the plurality of members belonging to the medical consortium.

For example, the organization administration module is configured to enable the member of the $N^{th}$-level in the organization to have an authority to acquire data of the member of the $M^{th}$-level in the organization. For example, by enabling the member of the $N^{th}$-level in the organization to have the authority to acquire the data of the member of the $M^{th}$-level in the organization, a higher-level member in the organization may administrate a lower-level member. For example, if a superior hospital notices that, between two subordinate hospitals, a first subordinate hospital has more actual patients and a second subordinate hospital has fewer actual patients; when transferring patients to be referred to a subordinate hospital, the superior hospital may assign more patients to be referred to the second subordinate hospital, thereby allowing the patients to have better medical experience.

For example, the organization administration module includes a data statistics module; and the data statistics module is configured to: receive a statistical data viewing request sent by the member of the $N^{th}$-level; acquire data of at least some members among members from a first-level to the $N^{th}$-level based on the statistical data viewing request; analyze the data of the at least some members to acquire a statistical result; and output the statistical result.

For example, the statistical result includes at least one selected from a group consisting of the total number of objects associated with the at least some members, the number of newly added objects associated with the at least some members, gender distribution of the objects associated with the at least some members, regional distribution of the objects associated with the at least some members, and level distribution of the objects associated with the at least some members.

Figure 18:
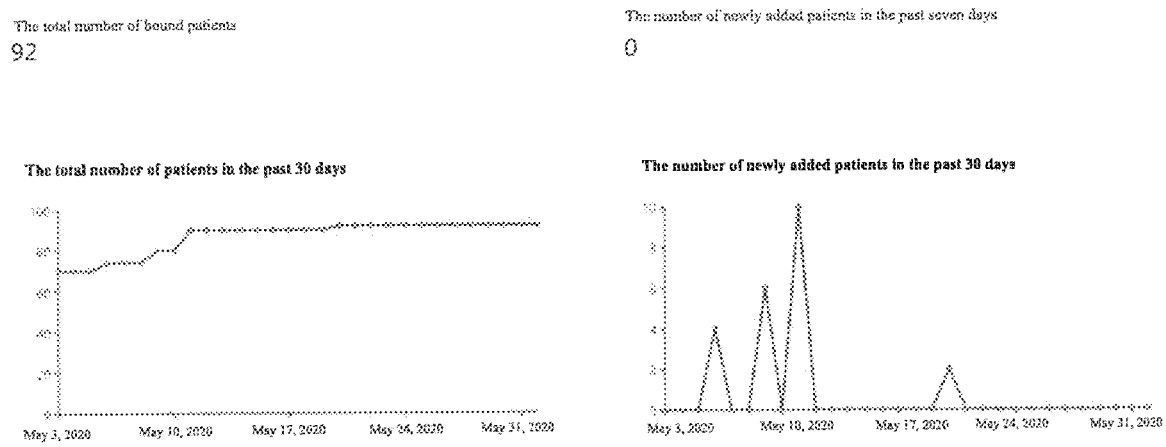
FIG. 18 is a schematic diagram of two curves acquired based on a data statistics module provided by at least one embodiment of the present disclosure.

For example, the member of the $N^{th}$-level may send a request of "acquiring a statistical result of the total number of objects associated with a specified member of the members of the $M^{th}$-level and a statistical result of the number of newly added objects associated with a specified member of the members of the $M^{th}$-level"; the data statistics module is configured to acquire, based on the above-described request, the total number of objects that are associated with the specified member of the members of the $M^{th}$-level and the number of newly added objects that are associated with the specified member of the members of the $M^{th}$ level; acquire, based on the above-described total number of objects that are associated with the specified member of the members of the $M^{th}$-level and the number of newly added objects that are associated with the specified member of the members of the $M^{th}$-level, "a curve of the total number of objects associated with the specified member of the members of the $M^{th}$-level changing with time" and "a curve of the number of newly added objects associated with the specified member of the members of the $M^{th}$-level changing with time"; and output the above-described two curves (e.g., provide the above-described two curves to the front-end page associated with the organization administration module). For example, exemplary graphs of the above-described two curves are shown in FIG. 18. For example, the home board page of the first individual service module may also display curves similar to the above-described two curves.

For example, by making the organization administration module include the data statistics module, the higher-level members may know better a situation of the lower-level members.

For example, the organization administration module includes a device allocation sub-module; the organization administration page further includes a device allocation page; and the device allocation sub-module is configured to allocate at least one of a plurality of devices to be allocated that are associated with the health administration apparatus to at least one of the plurality of members belonging to the organization. For example, the device allocation page may display a device to be allocated; an administrator of the medical consortium may click on an "Allocate" button associated with the device to be allocated on the device allocation page, and select a member to receive the device to be allocated, so that the at least one of the plurality of devices to be allocated that are associated with the health administration apparatus is allocated to at least one of the plurality of members belonging to the organization.

Figure 19:
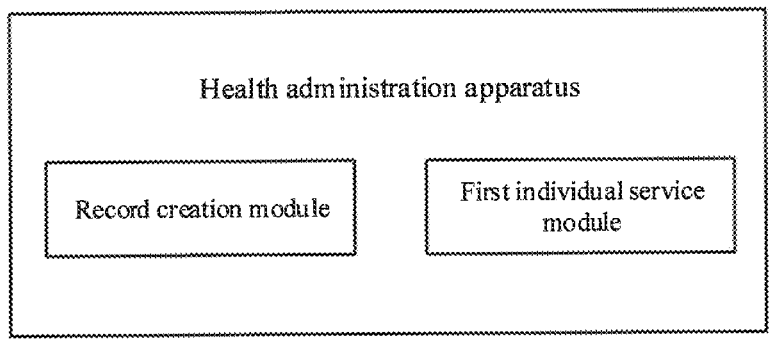
FIG. 19 is an exemplary block diagram of still another health administration apparatus provided by at least one embodiment of the present disclosure.

FIG. 19 is an exemplary block diagram of still another health administration apparatus provided by at least one embodiment of the present disclosure. For example, as shown in FIG. 19, in addition to the record creation module, the health administration apparatus further includes a first individual service module.

For example, when the first individual service module is implemented as a front-end page, the first individual service module may include at least one selected from a group consisting of a page associated with the device administration module, a page associated with an object administration module, a page associated with a two-way administration module, a page associated with the rehabilitation module, and a page associated with the third record creation sub-module, so as to allow the first individual service module to perform data interaction with a corresponding module.

In some examples, the health administration apparatus may further include an object service module. For example, for specific implementation modes of the first individual service module and the object service module, the foregoing examples may be referred to, and no details will be repeated here.

Figure 20:
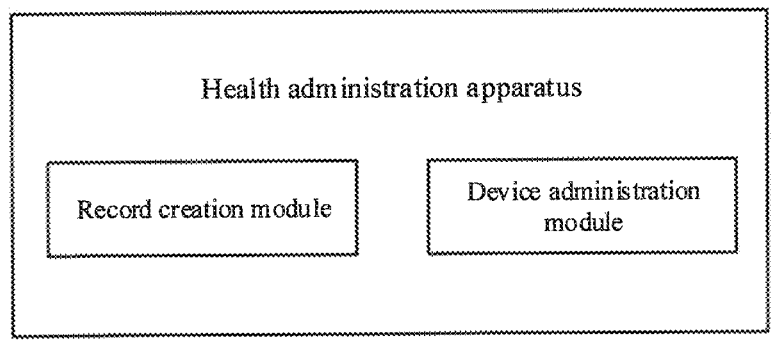
FIG. 20 is an exemplary block diagram of still another health administration apparatus provided by at least one embodiment of the present disclosure.

FIG. 20 is an exemplary block diagram of still another health administration apparatus provided by at least one embodiment of the present disclosure. For example, as shown in FIG. 20, in addition to the record creation module, the health administration apparatus further includes a device administration module. Correspondingly, the first individual service module may include a page associated with the device administration module, to allow the first individual service module to perform data interaction with the device administration module.

For example, the device administration module is configured to implement a function of searching a specified device from devices associated with the health administration apparatus.

Figures 21, 22, 23:
FIG. 21 shows a schematic diagram of a front-end page matching a hospital device sub-module of a device administration module provided by at least one embodiment of the present disclosure.
FIG. 22 shows a two-dimensional code generated by the device administration module provided by at least one embodiment of the present disclosure.
FIG. 23 shows a schematic diagram of a front-end page matching a personal device sub-module of the device administration module provided by at least one embodiment of the present disclosure.

FIG. 21 shows a schematic diagram of a front-end page matching a hospital device sub-module of a device administration module provided by at least one embodiment of the present disclosure. FIG. 23 shows a schematic diagram of a front-end page matching a personal device sub-module of the device administration module provided by at least one embodiment of the present disclosure.

For example, a hospital device is a device belonging to a hospital; and a patient device is a device belonging to a patient. For example, a hospital device may be associated with a plurality of patients in a time-sharing manner; and a patient device may only be associated with a patient who owns the patient device. For example, a hospital device may include any one or any combination of the first current device, the second current device, the third current device, and the fourth current device as described above.

For example, as shown in FIG. 21, the front-end page matching the hospital device sub-module of the device administration module is configured to display a list of hospital devices associated with the health administration apparatus, and allows a medical worker to search a specified hospital device by selecting a search field and inputting search content.

For example, as shown in FIG. 23, the front-end page matching the personal device sub-module of the device administration module is configured to display a list of personal devices associated with the health administration apparatus, and allows a medical worker to search a specified personal device by selecting a search field and inputting search content.

For example, the hospital device sub-module of the device administration module is configured to generate, based on an identification code of the hospital device associated with the health administration apparatus, a barcode (e.g., a two-dimensional code) of the hospital device associated with the health administration apparatus. For example, one may click on "View QR Code" on the page shown in FIG. 21 to view the two-dimensional code of the device associated with the health administration apparatus. FIG. 22 shows a two-dimensional code generated by the device administration module provided by at least one embodiment of the present disclosure.

For example, the hospital device sub-module of the device administration module is configured to dissolve an association relationship between a device and the health administration apparatus. For example, a doctor may click on "Unbind" on the page shown in FIG. 21, so that the front-end page matching the hospital device sub-module of the device administration module sends a request of unbinding a specified device, and the hospital device sub-module of the device administration module receives the request of unbinding the specified device sent by the front-end page, and then, the association relationship between the specified device and the health administration apparatus is dissolved based on the above-described request.

Figure 24:
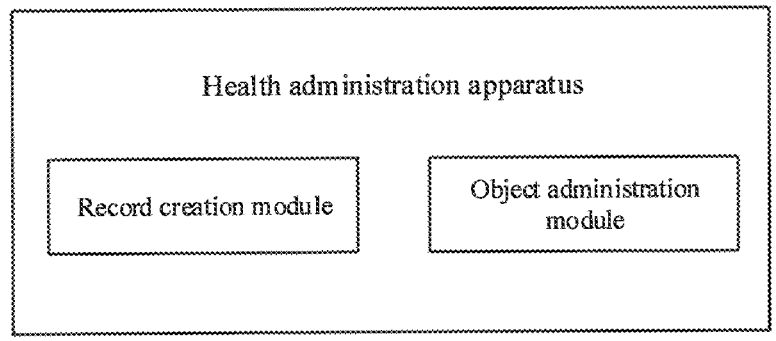
FIG. 24 is an exemplary block diagram of still another health administration apparatus provided by at least one embodiment of the present disclosure.

FIG. 24 is an exemplary block diagram of still another health administration apparatus provided by at least one embodiment of the present disclosure. For example, as shown in FIG. 24, in addition to the record creation module, the health administration apparatus further includes an object administration module. Correspondingly, the first individual service module may include a page associated with the object administration module, to allow the first individual service module to perform data interaction with the object administration module.

For example, as shown in FIG. 3A, the front-end page (e.g., the patient list page) matching the object administration module is configured to display a list of objects (e.g., patients) associated with a user (e.g., a medical worker) of the health administration apparatus, and allow the medical worker to search a specified object (e.g., a patient) by selecting a search field and inputting search content.

For example, the object administration module is further configured to receive a mobile phone number of an object (e.g., a patient) to be associated that is inputted by an individual (e.g., inputted into a patient binding page matching the object administration module), to achieve to bind the object (e.g., the patient) with the individual.

Figure 25:
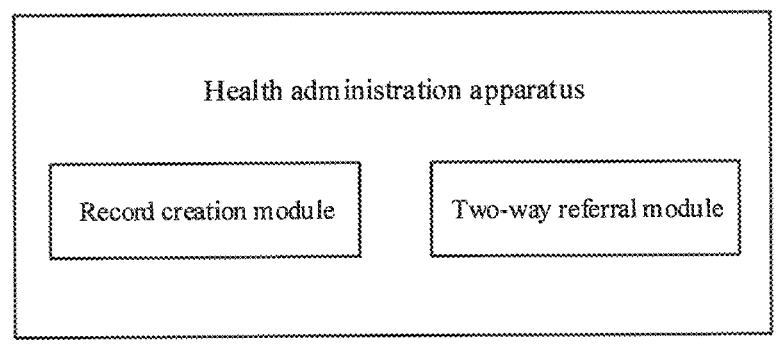
FIG. 25 is an exemplary block diagram of still another health administration apparatus provided by at least one embodiment of the present disclosure.

FIG. 25 is an exemplary block diagram of still another health administration apparatus provided by at least one embodiment of the present disclosure. For example, as shown in FIG. 25, in addition to the record creation module, the health administration apparatus further includes a two-way referral module. Correspondingly, the first individual service module may include a page associated with the two-way referral module, to allow the first individual service module to perform data interaction with the two-way referral module.

Figure 26:
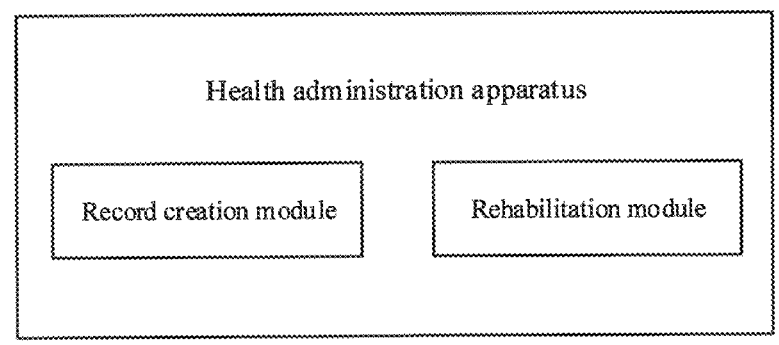
FIG. 26 is an exemplary block diagram of still another health administration apparatus provided by at least one embodiment of the present disclosure.

FIG. 26 is an exemplary block diagram of still another health administration apparatus provided by at least one embodiment of the present disclosure. For example, as shown in FIG. 26, in addition to the record creation module, the health administration apparatus further includes a rehabilitation module. Correspondingly, the first individual service module may include a page associated with the rehabilitation module, to allow the first individual service module to perform data interaction with the rehabilitation module.

For sake of clarity, specific contents of the two-way referral module and the rehabilitation module will be explained at the end of the specification, and no details will be repeated here.

It should be noted that, in addition to including the record creation module, the health administration apparatus provided by at least one embodiment of the present disclosure may include any combination of the organization administration module, the object service module, the first individual service module, the second individual service module, the device administration module, the two-way referral module, the object administration module, and the rehabilitation module.

Figure 27:
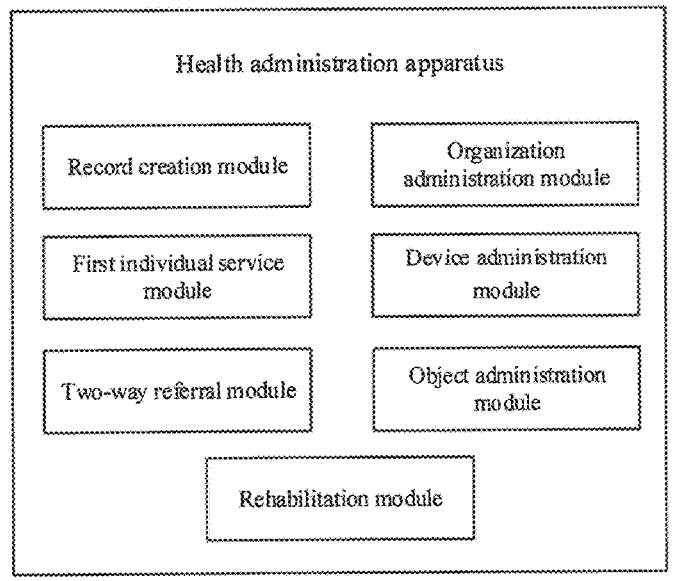
FIG. 27 is an exemplary block diagram of still another health administration apparatus provided by at least one embodiment of the present disclosure.

FIG. 27 is an exemplary block diagram of still another health administration apparatus provided by at least one embodiment of the present disclosure. For example, as shown in FIG. 27, in addition to the record creation module, the health administration apparatus further includes an organization administration module, a first individual service module, a device administration module, a two-way referral module, an object administration module, and a rehabilitation module.

At least one embodiment of the present disclosure further provides a data collection apparatus, which includes: an object identity information data acquisition terminal, a second individual service module, and a third current device. The second individual service module is used in the object identity information data acquisition terminal; the third current device is configured to be associated with the object identity information data acquisition terminal; the object identity information data acquisition terminal is configured to acquire identity information of the current object and provide the identity information of the current object to the second individual service module; and the second individual service module is configured to acquire, based on an identification code of the third current device, device-related data generated by the third current device and corresponding to the identity information of the current object, and associate the device-related data and the identity information of the current object with each other.

For example, the above-described device-related data and the identity information of the current object associated with each other are provided to the health administration apparatus.

Figure 28:
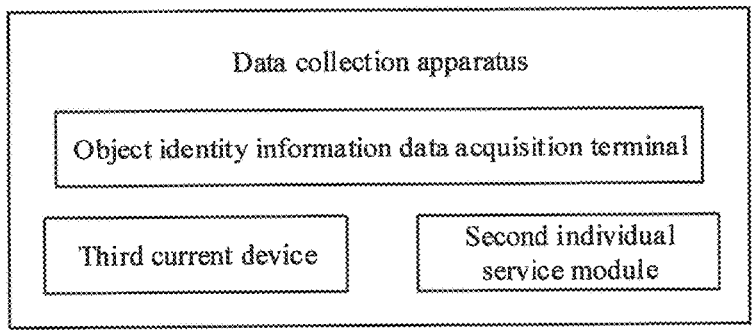
FIG. 28 is an exemplary block diagram of a data collection apparatus provided by at least one embodiment of the present disclosure.

FIG. 28 is an exemplary block diagram of a data collection apparatus provided by at least one embodiment of the present disclosure. For example, as shown in FIG. 28, the data collection apparatus includes an object identity information data acquisition terminal, a second individual service module, and a third current device. For example, for specific implementation modes of the object identity information data acquisition terminal, the second individual service module, and the third current device, the example shown in FIG. 8 may be referred to, and no details will be repeated here.

For example, by applying the function of the object identity information data acquisition terminal (e.g., the POS machine) of reading information contained in the identity document, and integrating the object identity information data acquisition terminal (e.g., the POS machine), the third current device (e.g., the respiratory screening instrument), and the second individual service module (e.g., the respiratory rehabilitation service APP) into one data collection apparatus, portable administration and use of the third current device (e.g., the respiratory screening instrument) may be implemented. For example, it is convenient for a doctor and a nurse to use the third current device (e.g., the respiratory screening instrument) and acquire a patient's test report in time during diagnosis and treatment for the patient either in the hospital or out of the office, and provide the medical advice to the patient in time, which, thus, can improve portability of instruments and work efficiency of medical workers. For example, the object identity information data acquisition terminal further has a function of printing the report of the object.

Figure 29:
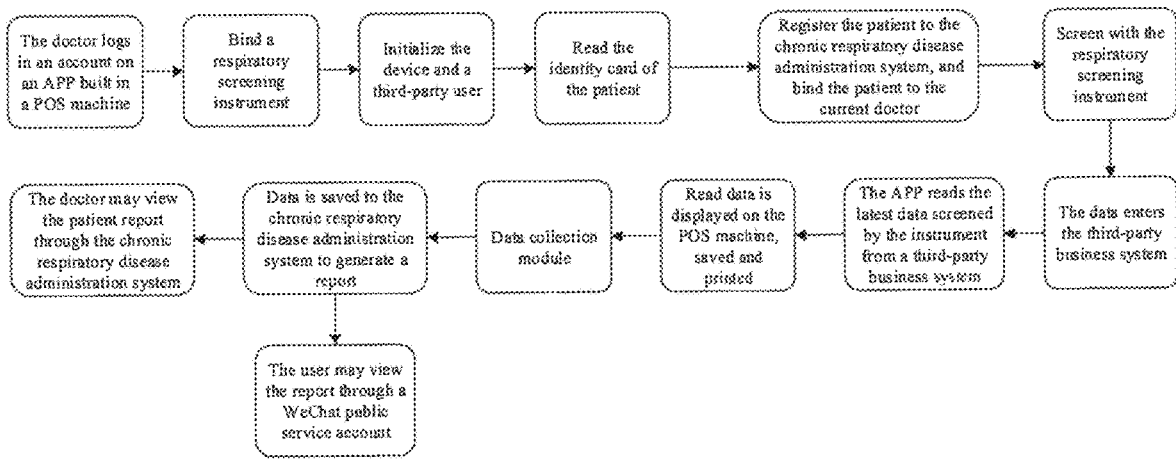
FIG. 29 is a work flow chart of the data collection apparatus shown in FIG. 28.

FIG. 29 is a work flow chart of the data collection apparatus shown in FIG. 28. The working flow of the data collection apparatus shown in FIG. 28 will be exemplarily described below in conjunction with the example shown in FIG. 29 as well as FIG. 9A, FIG. 9B, FIG. 10A, FIG. 10B, FIG. 11A, and FIG. 11B.

First, the doctor (or the nurse) turns on the POS machine and connects the POS machine to the Internet, then opens the respiratory rehabilitation service APP on the POS machine, and enters the page shown in FIG. 9A.

Second, click on "Pulmonary Function Screening" on the page shown in FIG. 9A, and enter the pulmonary function screening module. For example, when using the POS machine for the first time, perform related operations according to the operation guide shown on the page shown in FIG. 9B.

Third, as shown in FIG. 29, FIG. 10A, and FIG. 10B, the doctor (or the nurse) logs in a doctor (or nurse) account on the respiratory rehabilitation service APP built in the POS machine; after login is successful, the doctor (or the nurse) establishes a binding relationship with the POS machine. As shown in FIG. 10A, login may be performed through a mobile phone number and a verification code, and the page after successful login is shown in FIG. 10B.

For example, after the doctor has successfully logged in, a registered patient (i.e., a patient whose identity document information is read by the POS machine bound to the doctor) will have a binding relationship with the doctor who logs in on the current respiratory rehabilitation service APP. For example, the same doctor may log in on respiratory rehabilitation service APPs of a plurality of POS machines; and in this case, registered patients involved in the respiratory rehabilitation service APP of each POS machine are all bound to the above-described same doctor. For example, the respiratory rehabilitation service APP of each POS machine may allow only one doctor to log in; and if the doctor logging in the respiratory rehabilitation service APP of the POS machine needs to be changed, it is necessary to log out the original doctor account, and then log in a new doctor account.

Fourth, after the doctor (or the nurse) logs in successfully, it automatically jumps to the step guide page; the doctor (or the nurse) clicks on the bound device, and then enters a device serial number input interface shown in FIG. 11A; after entering the device serial number, click on "OK" on the device serial number input interface shown in FIG. 11A to enter the device serial number display and edit page shown in FIG. 11B.

Fifth, as shown in FIG. 29, FIG. 11A, and FIG. 11B, the doctor (or the nurse) inputs the serial number of the pulmonary function instrument (i.e., the respiratory screening instrument) on the graphical user interface shown in FIG. 11A, to bind the pulmonary function instrument (i.e., the respiratory screening instrument), that is, to bind the pulmonary function instrument (i.e., the respiratory screening instrument) with the POS machine. For example, because a binding relationship between the doctor (or the nurse) and the POS machine has been established at this time, after the respiratory screening instrument is bound to the POS machine, a binding relationship between the doctor (or the nurse) and the respiratory screening instrument is also established.

Sixth, as shown in FIG. 29, after the doctor (or the nurse) successfully types in the device to be bound, it automatically enters the step guide page to start data initialization, that is, the initialization of the device and a third-party user as shown in FIG. 29. Through the data initialization, an ID of a virtual user having a binding relationship with the respiratory screening instrument may be acquired; if the data generated by the respiratory screening instrument needs to be acquired from the back-end system of the manufacturer of the respiratory screening instrument, the above-described ID of the virtual user bound to the serial number of the respiratory screening instrument may be used as a query condition.

Seventh, after the data initialization is completed, it enters the patient information input interface shown in FIG. 12A, to complete an operation of reading the identity card of the patient as shown in FIG. 29. The doctor (or the nurse) presses the identity card of the patient against an identity card placement region (e.g., a top portion) of the POS machine, and the POS machine may read the identity information of the patient.

Eighth, after reading the identity information of the patient, the respiratory rehabilitation service APP will automatically query whether the patient exists in the health administration apparatus according to the identity card number of the patient. If the patient does not exist in the health administration apparatus, the doctor (or the nurse) inputs basic information such as height and weight and clicks on "OK"; the respiratory rehabilitation service APP will provide the identity information and the basic information of the patient to the health administration apparatus, so as to complete registration of the patient in the health administration apparatus, that is, implement registering the patient to the chronic respiratory disease administration system (the health administration apparatus) as shown in FIG. 29; besides, the respiratory rehabilitation service APP will also provide the binding relationship between the patient and the doctor logging in the POS machine to the health administration apparatus, that is, implement the operation of binding the current doctor as shown in FIG. 29. If the patient exists in the health administration apparatus, the respiratory rehabilitation service APP will acquire the basic information of the patient from the health administration apparatus and fill the basic information of the patient into the patient information input interface shown in FIG. 12A, and the interface after the patient information is input is as shown in FIG. 12B. It should be noted that, in order to protect personal information, the identity card number and the mobile phone number are removed from FIG. 12B and other related drawings.

Eighth, after clicking on "OK" in the interface of FIG. 12B, it enters the screening page. Click on "Start Screening" on the screening page, and the respiratory screening instrument will perform screening on the patients. For example, in the screening process, the patient holds the respiratory screening instrument in hand under the guidance of the doctor, and detects his/her own breath by first inhaling and then exhaling forcefully; and during the process, the respiratory screening instrument acquires breath data of the patient through detection. It should be noted that, in some examples, the POS machine may also provide the operation instructions for the respiratory screening instrument in voice or/and text, so as to reduce workload of the doctor.

Ninth, after the respiratory screening instrument completes detection, the data acquired by the respiratory screening instrument through detection is transferred to a third-party business system (e.g., the back-end system of the manufacturer of the respiratory screening instrument).

Tenth, the doctor (or the nurse) clicks on the end screening; and the respiratory rehabilitation service APP will automatically acquire (acquire from the third-party business system) data generated through latest measurement by the above-described respiratory screening instrument, according to the ID of the virtual user corresponding to the respiratory screening instrument having a binding relationship with the currently used POS machine.

Eleventh, the data generated through latest measurement by the respiratory screening instrument and acquired by the respiratory rehabilitation service APP is organized into a report and supplied to the currently used POS machine for display, storage, and printing. FIG. 12D is a report display and print page. For example, after the data generated through latest measurement by the respiratory screening instrument is organized into a report, it automatically enters the report display and print page shown in FIG. 12D.

Twelfth, if the doctor believes that the report displayed on the POS machine has an error, he/she may click on "Rescreen" to perform screening again; if the doctor believes that the report displayed on the POS machine has no error, he/she clicks on "Save"; the data generated through latest measurement by the respiratory screening instrument will be supplied to the data collection module (e.g., the data preprocessing module); and the data collection module distributes the data to the health administration apparatus. For example, one may click on "Print" in an upper right corner of the print page shown in FIG. 12D to print the report on paper. For example, the data collection module may perform data preprocessing on the collected data to improve efficiency of storing the collected data in the health administration apparatus. For example, the above-described data preprocessing includes compensation for a data missing problem caused by frequencies of transmission and data collection.

Thirteenth, the data supplied to the health administration apparatus will be stored in the health administration apparatus, and the above-described data supplied to the health administration apparatus is used to generate a report of the patient.

Fourteenth, the patient may view his/her own respiratory screening report through a WeChat public service account; the doctor may view the respiratory screening report of the patient bound the doctor on the health administration apparatus. For example, the respiratory screening report seen by the patient may be the report shown in FIG. 12E. For example, the respiratory screening report seen by the doctor may be the report shown in FIG. 12F.

It should be noted that, in a case where the POS machine has been bound to the respiratory screening instrument, the fourth step to the sixth step may not be performed; in a case where the doctor has logged in to the APP built in the POS machine, the third step may not be performed; in a case where the doctor has logged in to the APP built into the POS machine, and the POS machine has been bound to the respiratory screening instrument, after clicking on "Pulmonary Function Screening" on the page shown in FIG. 9A, it will directly enter the patient information input interface shown in FIG. 12A.

Figure 30:
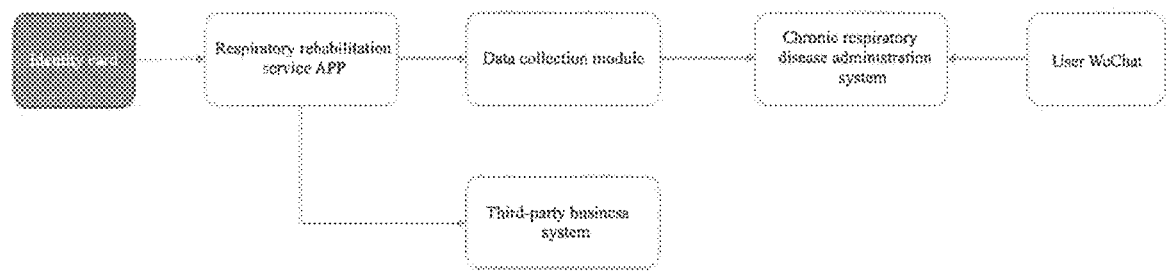
FIG. 30 is a schematic diagram of a software system related to the data collection apparatus shown in FIG. 28.

FIG. 30 is a schematic diagram of a software system related to the data collection apparatus shown in FIG. 28. For example, as shown in FIG. 30, the software system involved in the data collection apparatus shown in FIG. 28 includes a chronic respiratory disease administration system (e.g., the health administration apparatus), a data collection module, a respiratory rehabilitation service APP, a third-party business system, and an applet in the WeChat of the user.

Figure 31:
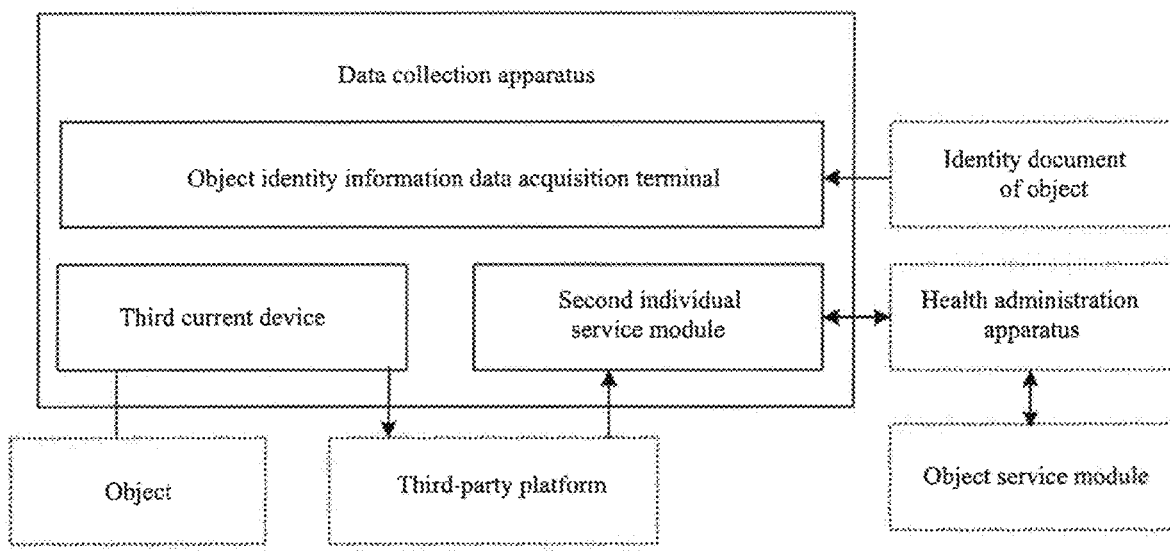
FIG. 31 is an exemplary block diagram of a first example of the data collection apparatus provided by at least one embodiment of the present disclosure.

FIG. 31 is an exemplary block diagram of a first example of the data collection apparatus provided by at least one embodiment of the present disclosure. It should be noted that, for convenience of description, FIG. 31 also shows the object, the third-party platform, the object service module, the health administration apparatus, and the object's identity document. For example, for specific description of the third-party platform, the object service module, the health administration apparatus, and the object's identity document, reference may be made to the example shown in FIG. 8, and no details will be repeated here.

For example, as shown in FIG. 31, the device-related data generated by the third current device is supplied to the third-party platform.

In one example, the second individual service module acquires the device-related data of the current object from the third-party platform, establishes an association relationship between the device-related data of the current object and the identity information of the current object, and supplies the device-related data of the current object and the identity information of the current object that are associated with each other to the health administration apparatus; and the health administration apparatus creates the device usage record based on the device-related data of the current object and the identity information of the current object that are associated with each other as described above and stores the device usage record. The object service module and the first individual service module of the health administration apparatus may query a storage apparatus of the health administration apparatus, to acquire the device usage record of the object for display.

In another example, the second individual service module acquires the device-related data of the current object from the third-party platform, and supplies the device-related data of the current object to the health administration apparatus; the health administration apparatus establishes an association relationship between the device-related data of the current object and the identity information of the current object, and supplies the device-related data of the current object and the identity information of the current object that are associated with each other to the memory and the second individual service module; and in this case, the amount of data processed at the terminal where the second individual service module is located can be reduced.

It should be noted that, the device-related data generated by the third current device included in the data collection apparatus provided by at least one embodiment of the present disclosure is not limited to being provided to the health administration apparatus via the third-party platform and the second individual service module. Description will be given below in conjunction with FIG. 32.

Figure 32:
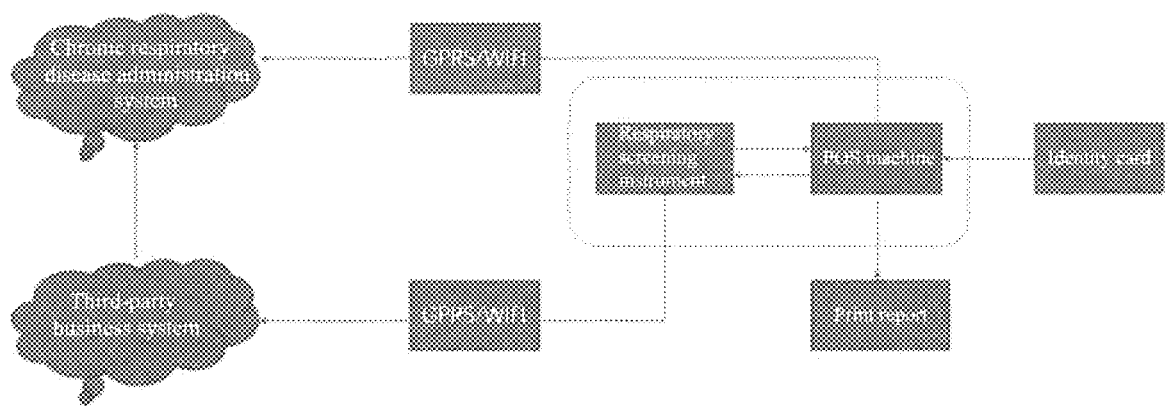
FIG. 32 shows a schematic diagram of an application example of the data collection apparatus provided by at least one embodiment of the present disclosure.

FIG. 32 shows a schematic diagram of an application example of the data collection apparatus provided by at least one embodiment of the present disclosure. For example, as shown in FIG. 32, the device-related data generated by the third current device included in the data collection apparatus is provided to the health administration apparatus via the third-party platform but not via the second individual service module, that is, the health administration apparatus directly acquires the device-related data generated by the third current device and related to the current object; and then, the second individual service module acquires the device-related data related to the current object and generated by the third current device from the health administration apparatus.

In one example, the health administration apparatus associates the device-related data generated by the third current device and the identity information of the object using the third current device with each other, and provides the device-related data generated by the third current device and the identity information of the object using the third current device that are associated with each other to the second individual service module. In another example, the second individual service module only acquires the device-related data generated by the third current device and related to the current object from the health administration apparatus, and establishes an association relationship between the device-related data related to the current object and generated by the third current device and the identity information of the current object; and correspondingly, the second individual service module provides the above-described association relationship to the health administration apparatus.

Figure 33:
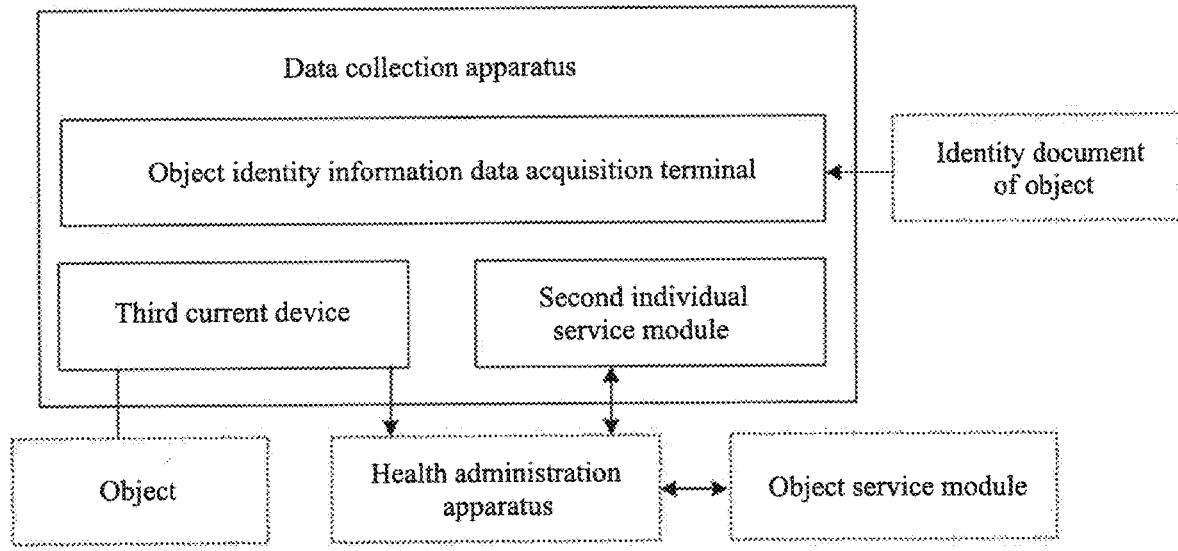
FIG. 33 is an exemplary block diagram of a second example of the data collection apparatus provided by at least one embodiment of the present disclosure.

FIG. 33 is an exemplary block diagram of a second example of the data collection apparatus provided by at least one embodiment of the present disclosure. The second example shown in FIG. 33 is similar to the first example shown in FIG. 31, only differences between the two will be explained here, and similarities will not be repeated.

For example, as shown in FIG. 33, the device-related data generated by the third current device included in the data collection apparatus is directly transferred to the health administration apparatus, that is, the health administration apparatus directly acquires the device-related data generated by the third current device from the third current device. For example, the health administration apparatus associates the device-related data generated by the third current device and the identity information of the object using the third current device with each other; and correspondingly, the second individual service module acquires, from the health administration apparatus, the device-related data and the identity information associated with each other for display. For another example, the second individual service module only acquires, from the health administration apparatus, the device-related data generated by the third current device and related to the current object, and establishes an association relationship between the device-related data, which is generated by the third current device and is related to the current object, and the identity information of the current object; and correspondingly, the second individual service module provides the above-described association relationship to the health administration apparatus.

Figure 34:
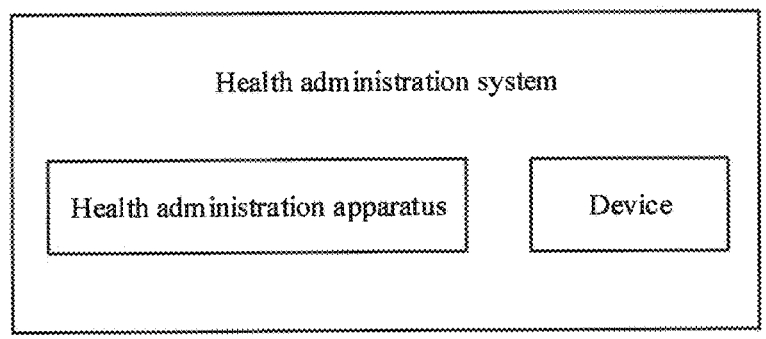
FIG. 34 is an exemplary block diagram of a health administration system provided by at least one embodiment of the present disclosure.

At least one embodiment of the present disclosure provides a health administration system. As shown in FIG. 34, the health administration system includes any health administration apparatus provided by at least one embodiment of the present disclosure and at least one of a plurality of devices related to the health administration apparatus.

For example, the plurality of devices are selected from a ventilator, an oxygen generator, a non-invasive multi-parameter detector, a pulse oximeter, and a pulmonary function instrument. For example, for a specific implementation mode of the health administration apparatus, the foregoing example may be referred to, and no details will be repeated here. For example, the above-described health administration system may further include at least one selected from a group consisting of an object identity information data acquisition terminal, a second individual service module, and an object service module.

For example, the plurality of devices include a third current device; the generating a device usage record of at least one object, at least based on identity information of the at least one object among the plurality of objects and data generated by a device used by the at least one object includes: receiving the identity information of the current object among the plurality of objects and device-related data generated by the third current device and associated with the identity information of the current object, here the third current device being a device that has been used by the current object; and generating the device usage record of the current object at least based on the identity information of the current object and the device-related data generated by the third current device and associated with the identity information of the current object.

For example, the health administration system further includes an object identity information data acquisition terminal and a second individual service module. The third current device is configured to be associated with the object identity information data acquisition terminal, the object identity information data acquisition terminal has the second individual service module built in; the object identity information data acquisition terminal is configured to acquire the identity information of the current object among the plurality of objects, and provide the identity information of the current object to the second individual service module; the second individual service module is configured to acquire, based on an identification code of the third current device, the device-related data generated by the third current device and corresponding to the identity information of the current object, associate the device-related data and the identity information of the current object with each other, and provide the device-related data and the identity information of the current object associated with each other to the health administration apparatus.

For example, the second individual service module is further configured to: acquire, based on the identity information of the current object, a query result provided by the health administration apparatus as to whether the current object exists in the memory; if the query result is that the current object exists in the memory, acquire the basic information of the current object from the memory; if the query result is that the current object does not exist in the memory, acquire the basic information of the current object, and provide the basic information and the identity information of the current object to the memory, to complete registration of the current object.

For example, the second individual service module is further configured to acquire information of an individual and the identification code of the third current device, and bind the individual to the third current device.

For example, the second individual service module is further configured to: associate the current object with the individual bound to the third current device, at least based on the identity information of the current object, and provide the association relationship between the current object and the individual bound to the third current device to the memory associated with the health administration apparatus.

For example, the second individual service module is further configured to generate a report of the current object, at least based on the device-related data generated by the third current device and associated with the identity information of the current object.

For example, the object identity information data acquisition terminal includes a monitor and a printer; the monitor is configured to display the report of the current object that is generated at least based on the device-related data; and the printer is configured to print the report of the current object that is generated at least based on the device-related data. For example, the third current device is a respiratory screening instrument.

For example, for specific implementation modes of the object identity information data acquisition terminal, the second individual service module, and the third current device, reference may made to the data collection apparatus shown in FIG. 28, and no details will be repeated here.

At least one embodiment of the present disclosure further provides a rehabilitation module. For example, the rehabilitation module may be a component of the above-described health administration apparatus.

Figure 35:
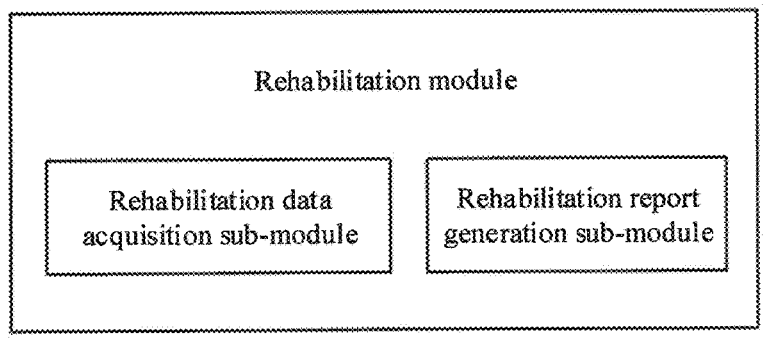
FIG. 35 is an exemplary block diagram of a rehabilitation module provided by at least one embodiment of the present disclosure.

FIG. 35 is an exemplary block diagram of a rehabilitation module provided by at least one embodiment of the present disclosure. As shown in FIG. 35, the rehabilitation module involves a plurality of objects, and includes: a rehabilitation data acquisition sub-module and a rehabilitation report generation sub-module. The rehabilitation data acquisition sub-module is configured to acquire data generated by a device used by at least one object among the plurality of objects, and provide the data generated by the device used by the at least one object among the plurality of objects to the rehabilitation report generation sub-module; and the rehabilitation report generation sub-module is configured to generate a rehabilitation report at least based on the data generated by the device used by the at least one object, and output the rehabilitation report.

For example, the rehabilitation module may update the rehabilitation report of the object in time based on the data generated by the device used by the object, so that the object may perform more targeted rehabilitation training, thereby shortening time required for curing.

For example, the rehabilitation data acquisition sub-module is configured to communicate with the rehabilitation data analyzing sub-module, to acquire analysis data generated by the rehabilitation data analyzing sub-module, and provide the analysis data to the rehabilitation report generation sub-module; and the rehabilitation report generation sub-module is configured to generate the rehabilitation report at least based on the data generated by the device used by the at least one object among the plurality of objects and the analysis data.

For example, the rehabilitation data analyzing sub-module is configured to generate the analysis data based on the data generated by the device used by the at least one object and template data.

For example, the rehabilitation data analyzing sub-module is configured to perform logistic regression analysis to generate the analysis data based on the data generated by the device used by the at least one object and the template data.

For example, the rehabilitation data analyzing sub-module is integrated in a gateway (e.g., a Bluetooth gateway) that communicates with the device used by the at least one object; and the rehabilitation data analyzing sub-module receives the data generated by the device used by the at least one object among the plurality of objects from the gateway. For example, by integrating the rehabilitation data analyzing sub-module into the gateway (e.g., the Bluetooth gateway) that communicates with the device used by the at least one object; the amount of computing in the cloud may be reduced, thereby making it suitable for application scenarios with a large amount of data (e.g., nursing homes, hospitals, rehabilitation centers, etc.).

For example, the device used by the at least one object includes at least one type of devices arranged in a nursing home, a rehabilitation center, and a hospital.

For example, the rehabilitation module further includes a rehabilitation data analyzing sub-module, the rehabilitation data analyzing sub-module is configured to receive the data generated by the device used by the at least one object among the plurality of objects from the rehabilitation data acquisition sub-module.

For example, the device used by the at least one object includes a personal device of the at least one object.

For example, the rehabilitation module further includes a remote management module, the remote management module is configured to communicate with the rehabilitation report generation sub-module, to acquire the rehabilitation report.

For example, the rehabilitation module further includes an individual service module for the terminal of the individual. The remote management module is configured to provide the rehabilitation report to the individual service module; and the terminal where the individual service module is located is configured to display the rehabilitation report to allow the individual to provide advice to the at least one object.

For example, the rehabilitation module further includes an object service module for at least one object. The remote management module is configured to provide the rehabilitation report to the object service module; and the terminal where the object service module is located is configured to display the rehabilitation report to allow the at least one object to view.

For example, the remote management module allows the object service module to communicate with the individual service module, to allow the individual to communicate with the at least one object.

For example, the rehabilitation module further includes a relative-and-friend service module for relatives and friends of the at least one object; the remote management module is configured to provide the rehabilitation report to the relative-and-friend service module; and the terminal where the relative-and-friend service module is located is configured to display the rehabilitation report, to allow the relatives and the friends of the at least one object to view. For example, by making the rehabilitation module further include the relative-and-friend service module, the relatives and the friends of the object may participate in the rehabilitation training of the object more deeply, thereby making the object persist in long-term rehabilitation training.

For example, the remote management module allows the relative-and-friend service module to communicate with at least one selected form a group consisting of the object service module and the individual service module, so as to allow the relatives and the friends of the at least one object to communicate with the individual and the at least one object. For example, by making the remote management module allow the relative-and-friend service module to communicate with at least one selected form a group consisting of the object service module and the individual service module, the relatives and the friends of the at least one object may participate in the rehabilitation training of the object more deeply, thereby making the object persist in long-term rehabilitation training.

For example, the device used by the at least one object among the plurality of objects includes at least one category selected form a group consisting of a hospital device, a rehabilitation center device, a nursing home device, and a personal device.

For example, the rehabilitation data acquisition sub-module, the rehabilitation report generation sub-module, the rehabilitation data analyzing sub-module, and the remote management module are configured to be implemented by the server. For example, at least some of the rehabilitation data acquisition sub-module, the rehabilitation report generation sub-module, the rehabilitation data analyzing sub-module, and the remote management module are implemented by the same server. For example, the rehabilitation data acquisition sub-module, the rehabilitation report generation sub-module, and the remote management module are configured to be implemented by the same server (e.g., a cloud server); and the rehabilitation data analyzing sub-module is implemented by a processor or another server.

For example, the individual service module, the object service module, and the relative-and-friend service module may be implemented as a local end (or a front end). For example, the above-described local end or front end may be implemented by at least one selected from a group consisting of a network end, a mobile end, and a desktop end. For example, the mobile end may be implemented by an APP and an applet. For example, the applet may be a WeChat applet, an Alipay applet, or other applicable applets. For example, the front-end pages involved in the individual service module, the object service module, and the relative-and-friend service module are located in different terminals, respectively.

Figure 36:
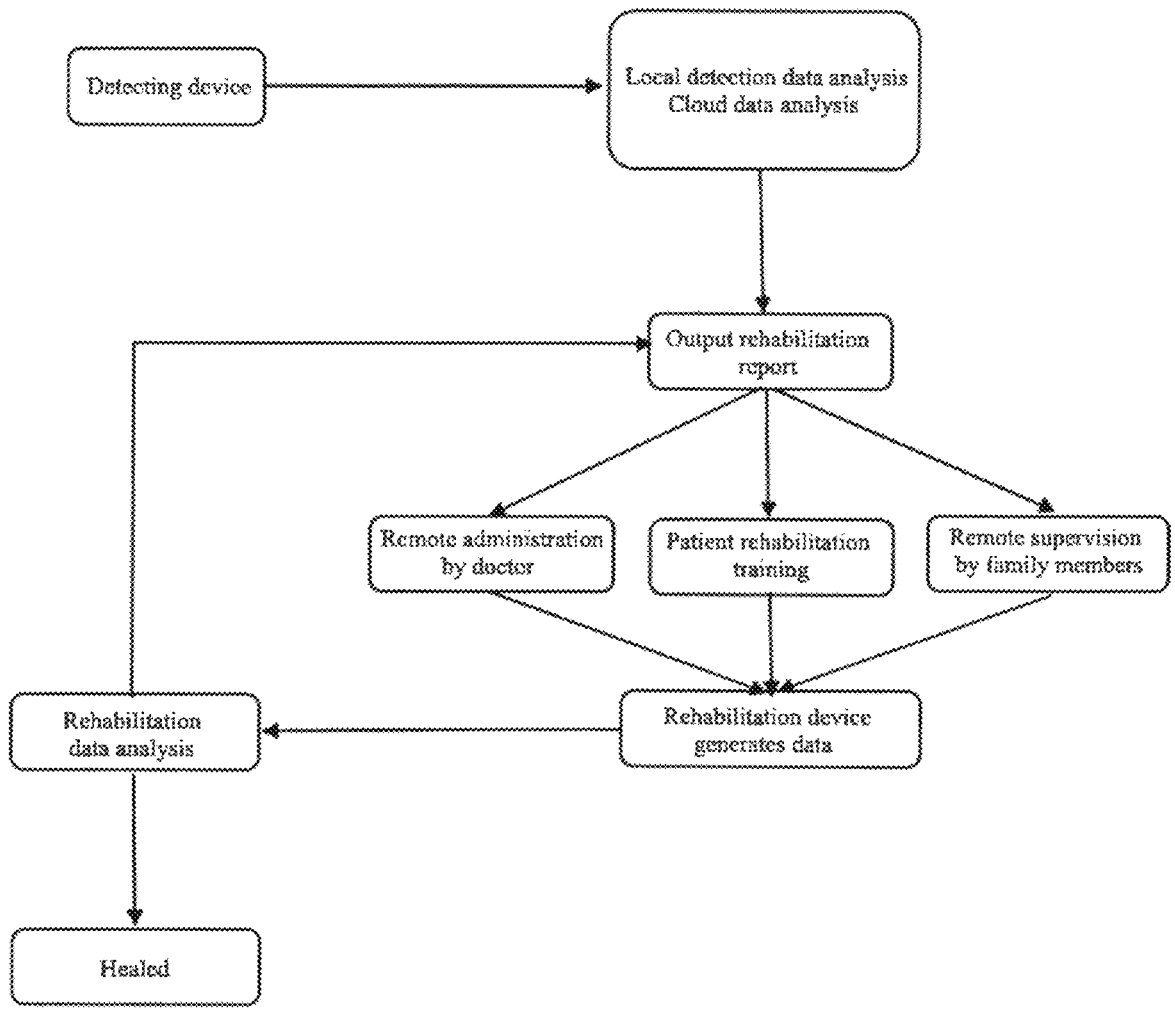
FIG. 36 is an exemplary flow chart of the health administration system shown in FIG. 35.

FIG. 36 is an exemplary flow chart of the health administration system shown in FIG. 35. As shown in FIG. 36, data generated by a detection device (e.g., a detection device of a hospital) is provided (e.g., provided via the rehabilitation data acquisition sub-module) to a data analyzing module (e.g., a local data analyzing module or a cloud data analyzing module); the data analyzing module analyzes the data generated by the detection device, and provides an analysis result to the rehabilitation report generation sub-module of the rehabilitation module. For example, a patient uses the rehabilitation device for rehabilitation training based on the guidelines of the above-described rehabilitation report, at the same time, a rehabilitation training report is sent to terminal devices of a doctor and a family member of the patient for display, to facilitate remote administration by the doctor (e.g., the doctor provides the advice based on the rehabilitation report), and remote supervision by the family member. When the patient uses the rehabilitation device for rehabilitation training, the data generated by the rehabilitation device is provided to the rehabilitation data analyzing sub-module; and the rehabilitation data analyzing sub-module analyzes the data generated by the rehabilitation device; if the patient has not been cured temporarily, the rehabilitation data analyzing sub-module provides an analysis result to the rehabilitation report generation sub-module; and the rehabilitation report generation sub-module generates a rehabilitation report based on the above-described analysis result and the data generated by the rehabilitation device.

For example, the above-described rehabilitation module may collect patient rehabilitation data through the Internet of Things, and perform integrative analysis to help the patient to recover. Technically, data transmission is carried out through Artificial Intelligence Internet of Things (AIOT).

For example, by coupling an AIOT module to a port of the detection device, the data is uploaded to the cloud through a port protocol, and at the same time, quick response may also be performed by edge computing inside the device. Due to the large number of devices connected to the rehabilitation system and a large scale of users, different processing methods are applied to different devices, respectively. For example, with respect to personal devices, data may be uploaded to the cloud for analysis; and with respect to hospital and nursing home devices, the rehabilitation data analyzing sub-module may be integrated in a Bluetooth gateway, to reduce the amount of computing in the background.

For example, the data generated by the detection device and the rehabilitation device of the patient may be compared with the health template data embedded in the device and the cloud, and the logistic regression analysis may be used to give a report on the use of the rehabilitation device by the patient.

For example, the rehabilitation remote administration involves doctors, family members, and patients. Each character has a different account and may perform remote video through the APP for rehabilitation administration, and the rehabilitation device report will also be released through the APP.

For example, the above-described rehabilitation module may be used in rehabilitation training for chronic obstructive pulmonary disease, and good rehabilitation training may speed up a cure cycle.

Figure 37:
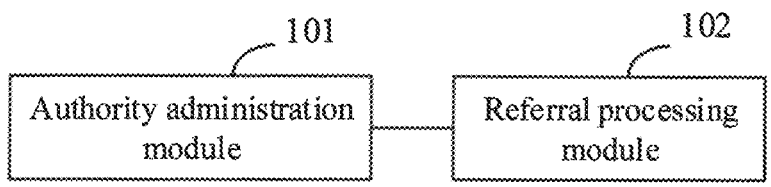
FIG. 37 is a structural block diagram of functions of a two-way referral system provided by an embodiment of the present disclosure.

At least one embodiment of the present disclosure provides a two-way referral system. Referring to FIG. 37, the two-way referral system 100 includes: an authority administration module 101 and a referral processing module 102. It should be noted that, the patient here corresponds to the object in the foregoing examples; and the referral processing module 102 here corresponds to the two-way referral module in the foregoing examples.

For example, the two-way referral system 100 may be used by users of a plurality of levels; the users of the plurality of levels may include patient users and doctor users, a level of a doctor user is higher than a level of a patient user, and the doctor user administrates the patient user belonging to his/her administration authority. In one example, one may be registered as the above-described user (e.g., registered as a doctor user or a patient user) through a corresponding registration port. The above-described registration port may be set by those skilled in the art according to actual situations, which will not be limited in the embodiments of the present disclosure.

In one example, the patient may use a registration page of the object service module shown in FIG. 3H to complete registration, and then is bound to a designated doctor to become a patient user within administration authority of the designated doctor. For example, the patient may use a terminal he/she holds to scan the doctor's two-dimensional code displayed on the "personal center" page of the first individual service module to implement binding with the doctor, so that the doctor may view relevant information of the patient.

In another example, the doctor may use the POS to acquire the information contained in the identity card of the patient, and type in basic information of the patient in the object information input interface of the second individual service module shown in FIG. 12A to implement patient registration and binding of the patient and the doctor, and no details will not be repeated here.

For example, the authority administration module 101 is configured to administrate the above-described users of the plurality of levels, comprises but are not limited to: administrating an administration authority of a doctor user. In one example, when a doctor user creates a patient user, the patient user may be defaulted to be a user who belongs to the administration authority of the doctor user; or the authority administration module 101 may respond to a referral request confirmation message sent by the referral processing module 102, and synchronize administration authority of a patient user to be referred from a first doctor user to a second doctor user, and at this time, the patient user to be referred is not only a patient user who belongs to the administration authority of the first doctor user, but also a patient user who belongs to the administration authority of the second doctor user; and the second doctor user may administrate the patient to be referred who belongs to his/her administration authority. A mode for the doctor user to create the patient user may be set by those skilled in the art according to actual situations, which will not be limited in the embodiments of the present disclosure.

For example, synchronization refers to that both may have authority at the same time, or may also refer to change in authority, that is, the user after change has authority, while the user before change no longer has authority.

When the patient user is a user within the administration authority of the doctor user, the administrating, by the doctor user, the patient user, includes: the doctor user performing administration operations on patient information of the patient user. The above-described administration operations include but are not limited to: creation, deletion, modification, and query. The above-described patient information may include, but is not limited to: name, age, gender, contact information, and the like of the patient user, and other basic information related to the patient user, as well as disease name, disease characteristics, medication information of the patient user, and other disease information related to the patient's disease.

The referral processing module 102 will be introduced below. For example, the referral processing module 102 is configured to receive a referral request carrying a user identification of the first doctor user and receive a query identification of the second doctor user, generate a referral request form visible to the second doctor user; and receive a referral request confirmation message fed back by the second doctor user according to the referral request form. For example, the referral processing module 102 is further configured to send the referral request confirmation message to at least one of the authority administration module 101, the first individual service module, and the object service module.

For example, the above-described referral request confirmation message is a message instructing the second doctor user to confirm acceptance of the patient to be referred. Those skilled in the art may understand that the referral processing module 102 is configured to receive the referral request confirmation message only in a case were the second doctor user confirms to receive the patient to be referred. For example, in a case where the second doctor user confirms refusal of the patient to be referred, the referral processing module 102 is configured to receive a referral request refusal message; and correspondingly, the referral processing module 102 is also configured to send the referral request refusal message to at least one of the authority administration module 101, the first individual service module, and the object service module. For example, the referral request confirmation message and the referral request refusal message as described above are referred to as referral request feedback.

For example, the user identification of the first doctor user is specifically identity information that can uniquely identify the first doctor user, in one example, as long as the first doctor user may be uniquely identified; and a setting form of the user identification of the first doctor user will not be limited in the embodiment of the present disclosure. A query identification of the second doctor user may specifically be identity information used to query the second doctor user, for example, the mobile phone number, name, etc. of the second doctor user may be used to query the information of the second doctor user. The referral request form may include: information of the patient user to be referred administrated by the first doctor user and referral information. The information of the user patient to be referred may include the patient information of the patient user to be referred; and the referral information may include referral reason and other information related to referral. For example, the user identification of the first doctor user is selected from mobile phone number, work number, and identity card number of the doctor. For example, the query identification of the second doctor user is selected from name, mobile phone number, work number, and identity card number of the doctor.

The above-described referral request carrying the user identification of the first doctor user and the query identification of the second doctor user may be provided by the first doctor user and sent to the referral processing module 102 via the above-described two-way referral administration page. After receiving the above-described referral request, the referral processing module 102 may display a corresponding referral request page on a first doctor user side; the referral request page may include an input entry of the query identification; the first doctor user may input the query identification of the second doctor user through the above-described input entry; after receiving the query identification of the second doctor user, the referral processing module 102 generates a referral request form visible to the second doctor user on a second doctor user side; and the second doctor user may know information of the patient user to be referred and referral information by viewing the referral request form. When the second doctor user confirms acceptance of referral of the patient user to be referred, the second doctor user may feedback the referral request confirmation message; for example, a corresponding operation button for confirming the referral is set on a page of the referral request form; the second doctor user clicks on the above-described operation button on the above-described page to feedback the referral request confirmation message; after the referral processing module 102 receives the referral request confirmation message fed back by the second doctor user according to the referral request form, the referral processing module 102 sends the above-described referral request confirmation message to the authority administration module 101, to facilitate the authority administration module 101 to respond to the above-described referral request confirmation message and to perform the operation of synchronizing the administration authority of the patient user to be referred from the first doctor user to the second doctor user, thereby completing the referral process for the patient user to be referred.

The referral processing module 102 (i.e., the two-way referral module) provided by at least one embodiment of the present disclosure will be exemplarily described below in conjunction with FIG. 49 to FIG. 53.

Figures 49, 50, 51:
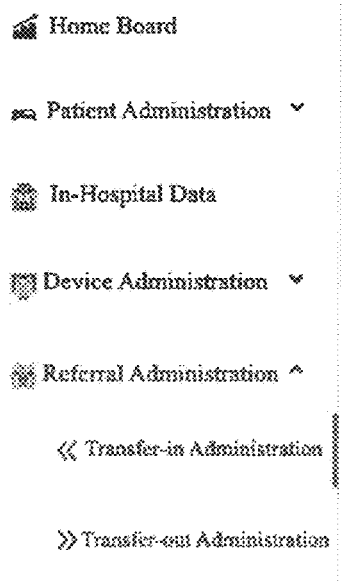
FIG. 49 is a schematic diagram of a guide page of a first individual service module provided by at least one embodiment of the present disclosure.
FIG. 50 is a schematic diagram of a transfer-out administration page of a referral administration page of the first individual service module provided by at least one embodiment of the present disclosure.
FIG. 51 is a schematic diagram of a patient selection sub-page of the transfer-out administration page provided by at least one embodiment of the present disclosure.
Figures 52, 53:
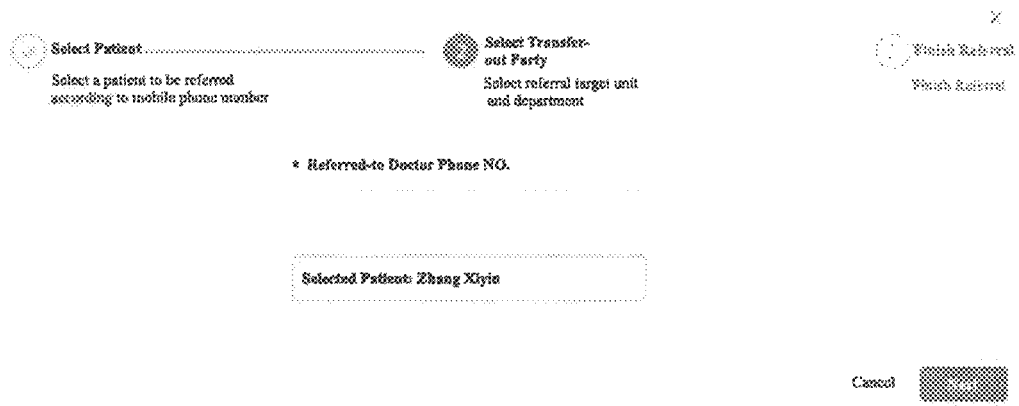
FIG. 52 is a schematic diagram of a transfer-out party selection sub-page of the transfer-out administration page provided by at least one embodiment of the present disclosure.
FIG. 53 is a schematic diagram of a transfer-person administration page of the referral administration page of the first individual service module provided by at least one embodiment of the present disclosure.

FIG. 49 is a schematic diagram of a guide page of the first individual service module provided by at least one embodiment of the present disclosure; FIG. 50 is a schematic diagram of a transfer-out administration page of the referral administration page of the first individual service module provided by at least one embodiment of the present disclosure; FIG. 51 is a schematic diagram of a patient selection sub-page of the transfer-out administration page provided by at least one embodiment of the present disclosure; FIG. 52 is a schematic diagram of a transfer-out party selection sub-page of the transfer-out administration page provided by at least one embodiment of the present disclosure; and FIG. 53 is a schematic diagram of a transfer-person administration page of the referral administration page of the first individual service module provided by at least one embodiment of the present disclosure.

First, the first doctor (i.e., the doctor who wants to transfer the patient to be referred) clicks "Transfer-out Administration" on the guide page of the first individual service module shown in FIG. 49, so as to enter the transfer-out administration page of the referral administration page shown in FIG. 50.

Second, the first doctor clicks "Initiate Referral" on the transfer-out administration page of the referral administration page shown in FIG. 50 to enter the patient selection sub-page of the transfer-out administration page shown in FIG. 51, and inputs the phone number of the patient to be referred on the patient selection sub-page; and correspondingly, the two-way referral module receives the phone number of the patient to be referred provided by the patient selection sub-page of the transfer-out administration page.

Third, the first doctor clicks "Next" on the patient selection sub-page shown in FIG. 51 to enter the transfer-out party selection sub-page of the transfer-out administration page shown in FIG. 52, and inputs the telephone number of the doctor (e.g., the second doctor) requested to accept the patient to be referred on the transfer-out party selection sub-page; and correspondingly, the two-way referral module receives the telephone number of the doctor requested to accept the patient to be referred supplied by the patient transfer-out party selection sub-page of the transfer-out administration page.

Fourth, the first doctor clicks "Next" on the transfer-out party selection sub-page shown in FIG. 52; and the two-way referral module associates a referral request containing the information of the patient to be referred and the information of the first doctor with the doctor requested to accept the patient to be referred (e.g., the second doctor), based on the phone number of the doctor requested to accept the patient to be referred.

Fifth, after the doctor requested to accept the patient to be referred (e.g., the second doctor) logs in to the health administration apparatus, the doctor requested to accept the patient to be referred (e.g., the second doctor) may see the above-described referral request on the transfer-person administration page of the referral administration page of the first individual service module shown in FIG. 53. For example, the doctor requested to accept the patient to be referred (e.g., the second doctor) may click "Accept Referral" or "Refuse Referral" to give feedback on the above-described referral request; and correspondingly, the two-way referral module receives the referral request feedback supplied by the doctor requested to accept the patient to be referred (e.g., the second doctor) via the transfer-person administration page of the referral administration page, and supplies the above-described referral request feedback to at least one selected from a group consisting of the authority administration module 101, the first individual service module associated with the first doctor, and the object service module associated with the patient to be referred.

Figure 38A:
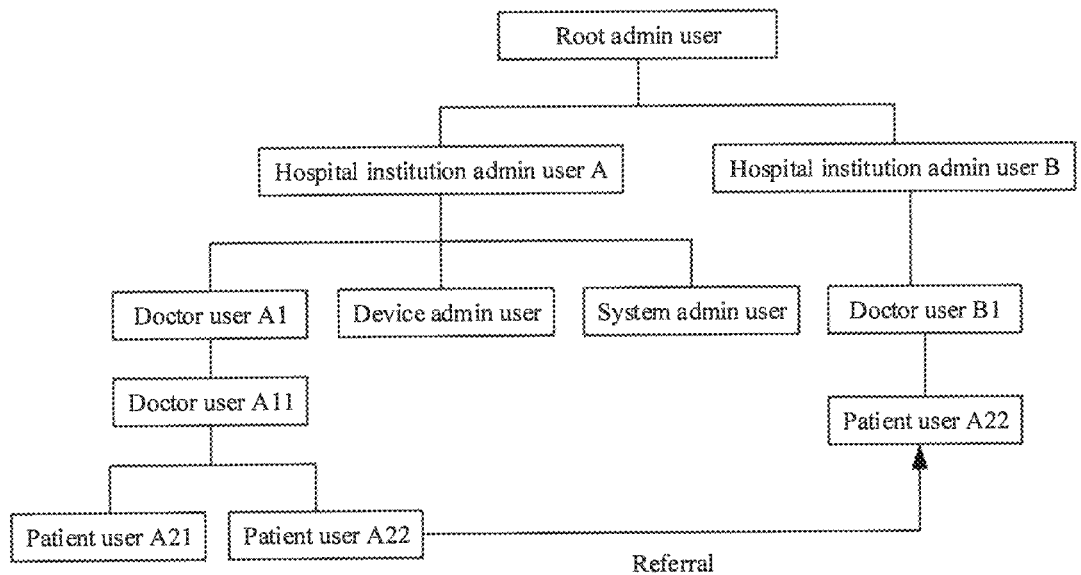
FIG. 38A is a schematic diagram of an administration authority of users in the two-way referral system provided by the embodiment of the present disclosure.
Figure 38B:
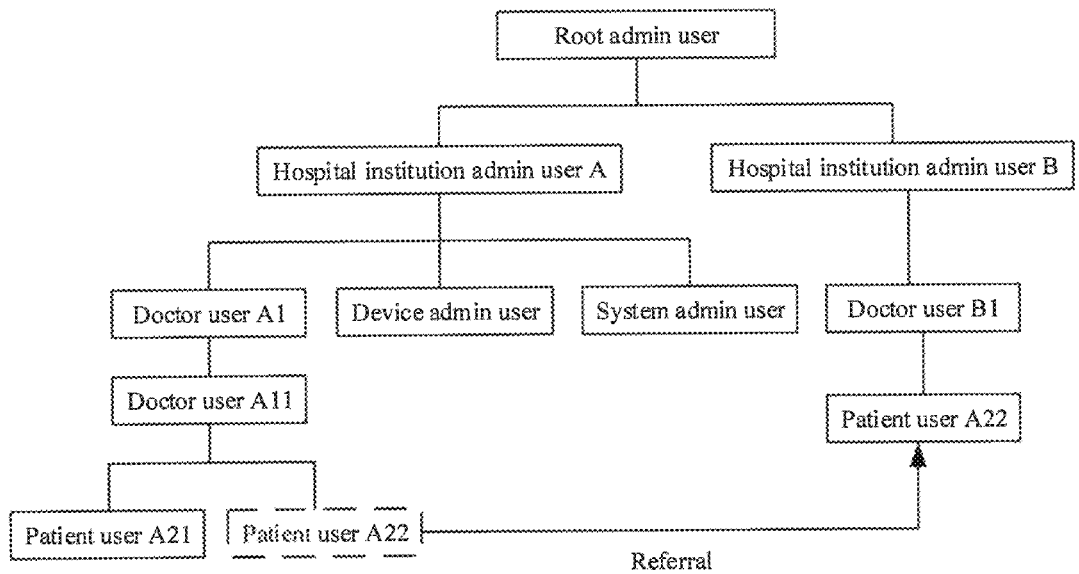
FIG. 38B is a schematic diagram of an administration authority of users in the two-way referral system provided by the embodiment of the present disclosure.

For example, in a case where the doctor requested to accept the patient to be referred (e.g., the second doctor) refuses the above-described referral request by clicking "Refuse Referral", the doctor requested to accept the patient to be referred (e.g., the second doctor) may also click "Refuse Referral" to enter a sub-page for inputting reasons for refusing referral to input a reason for refusing the above-described referral request; and correspondingly, the two-way referral module receives the reason for refusing referral, and supplies the reason for refusing referral as a portion of the referral request feedback to at least one of the first individual service module and the object service module. For example, in a case where the doctor requested to accept the patient to be referred (e.g., the second doctor) accepts the above-described referral request by clicking "Accept Referral", the two-way referral module supplies the referral request feedback (accept referral) to the authority administration module 101; and the authority administration module 101 is configured to change the administration authority of the patient to be referred. For example, as shown in FIG. 38B, the authority administration module 101 is configured to change the administration authority of the patient user to be referred from being administrated by the first doctor to being administrated by the second doctor; and in this case, the first doctor cannot view the information of the patient to be referred, and the second doctor can view the information of the patient to be referred. For example, by making the authority administration module 101 be configured to change the administration authority of the patient to be referred, the security of patient information can be improved and the above-described possible patient administration confusion problem can be addressed.

Sixth, in a case where the two-way referral module supplies the referral request feedback to the first individual service module associated with the first doctor, the first doctor may view the referral request feedback (or a referral status) supplied by the second doctor on the transfer-out administration page of the referral administration page shown in FIG. 50. For example, as shown in FIG. 50, in a case where the referral request feedback is that the referral is accepted, the referral status will be displayed as referral completed; and in a case where the referral request feedback is that the referral is refused, the referral status will be displayed as refuse referral, and the first doctor may click "Refuse Referral" shown in FIG. 50 to view the reason for refusing referral supplied by the second doctor.

For example, in a case where the referral request feedback is that the referral is accepted, the two-way referral module is further configured to supply the referral request feedback to the object service module associated with the patient to be referred; and in this case, the patient to be referred may view the information of the doctor who accepts the patient to be referred from "Referral Notice" on a main interface (home) of the object service module shown in FIG. 2A.

For example, the above-described first doctor may also be referred to as a first doctor user; and the above-described second doctor may also be referred to as a second doctor user.

For example, the two-way referral system provided by the embodiment of the present disclosure includes the authority administration module and the referral processing module; the authority administration module administrates users of a plurality of levels, so that each doctor user among the users of the plurality of levels administrates a patient user within his/her administration authority, and patient information of all patient users may be administrated in an isolated manner based on the administration authority of the doctor user, so as to effectively reduce probability of administration confusion events in the patient information administration process; and at the same time, the embodiments of the present disclosure can also effectively prevent the patient information of the patient users from being tampered with by a user having no administration authority, to ensure safety of the patient information; the referral processing module performs referral on the patient user to be referred, specifically, a referral request form visible to the second doctor user may be generated according to the received referral request carrying the user identification of the first doctor user and the received query identification of the second doctor user, the referral request form contains the information of the patient user to be referred administrated by the first doctor user and the referral information, so as to facilitate the second doctor user to check and review; and when receiving the referral request confirmation message fed back by the second doctor user according to the referral request form, by sending the referral request confirmation message to the authority administration module, the authority administration module responds to the above-described referral request confirmation message, and then synchronizes the administration authority of the patient user to be referred from the first doctor user to the second doctor user, and release the administration authority of the patient user to be referred to the second doctor user, so that the second doctor user may administrate the patient user to be referred, to achieve a purpose of accurately docking the patient information of the patient user to be referred to the corresponding doctor user who accepts the referral request. To sum up, the embodiments of the present disclosure can effectively solve the common problems of confused administration and docking of patient information in the referral process, and poor real-time performance of transferring the patient information, which effectively improves accuracy and efficiency of the referral process, and at the same time, effectively improves the refinement degree of patient information administration.

In one example, the two-way referral system 100 may perform referral on a patient user within the same hospital institution, or may also perform referral on a patient user between different hospital institutions.

For example, when performing referral on the patient user between different hospital institutions, the users of the plurality of levels according to the embodiment of the present disclosure may further include: at least one hospital institution admin user. The authority administration module 101 may also be configured to administrate the at least one hospital institution admin user. Referring to FIG. 38A and FIG. 38B (FIG. 38A and FIG. 38B only exemplarily show two hospital institution admin users, i.e., a hospital institution admin user A and a hospital institution admin user B; it can be understood that, in one example, the number of hospital institution admin users may be more than two), a level of a hospital institution admin user is higher than a level of a doctor user, and each hospital institution admin user administrates subordinate users who belong to his/her administration authority. The hospital institution admin users collectively belong to a root admin user; a level of the root admin user is higher than the level of the hospital institution admin user; the root admin user is used to administrate all hospital institution admin users, including administration operations such as creating and deleting hospital institution admin users.

In one example, the administrating, by a hospital institution admin user, subordinate users who belong to his/her administration authority, comprises: performing, by the hospital institution admin user, administration operations on user information of the subordinate users who belong to his/her administration authority; the above-described administration operations comprises but are not limited to: creating, deleting, modifying, and querying. The user information of the subordinate user may specifically be information related to the subordinate user.

For example, the above-described subordinate users may at least include: doctor users. In one example, the hospital institution admin user may create a doctor user; and the doctor user created by the hospital institution admin user is a doctor user who belongs to the administration authority of the hospital institution admin user. When the subordinate user is a doctor user, the user information of the subordinate user may specifically be doctor information of the doctor user, including: name, age, gender, contact information, working experience of the doctor user and other information related to the doctor user. A medical team usually contains a plurality of doctors, and there are a plurality of levels of doctors; for example, a chief physician administrates a subordinate deputy chief physician, then a level of the chief physician is higher than a level the deputy chief physician; the deputy chief physician administrates a subordinate general doctor, then a level of the deputy chief physician is higher than a level of the general doctor, and so on. In the embodiments of the present disclosure, there may be a plurality of levels of doctor users, an $n^{th}$-level doctor user administrates an $(n+1)^{th}$-level doctor user within his/her administration authority, an $n^{th}$-level is higher than an $(n+1)^{th}$-level; and n is a natural number. In one example, the administrating, by the $n^{th}$-level doctor user, the $(n+1)^{th}$-level doctor user within his/her administration authority includes: performing, by the $n^{th}$-level doctor user, administration operations on doctor information of the $(n+1)^{th}$-level doctor user within his/her administration authority; the above-described administration operations includes but are not limited to: creating, deleting, modifying, and querying. For example, referring to FIG. 38A and FIG. 38B, a level of a doctor user A1 is higher than a level of a doctor user A11; the doctor user A11 is a doctor user within administration authority of the doctor user A1; and the doctor user A1 administrates the doctor user A11.

Because each hospital is usually equipped with one or more medical devices, referring to FIG. 38A and FIG. 38B, subordinate users of each hospital institution admin user may also include: a device admin user; the authority administration module may also be configured to: administrate the administration authority of the device admin user. The administrating, by the device admin user, information of a medical device that belongs to the administration authority of the device admin user, may specifically include: performing, by the device admin user, administration operations on the information of the medical device that belongs to the administration authority of the device admin user, the above-described administration operations include but are not limited to: creating, deleting, modifying, and querying; the above-described information of the medical device includes but is not limited to: a medical device model, a medical device administrator, medical device ownership, and other medical device-related information.

For example, when a subordinate user contains a variety of role attributes such as a doctor user, a patient user, and a device admin user, in order to facilitate the administration of the role attributes of each subordinate user, referring to FIG. 38A and FIG. 38B, subordinate users of each hospital institution admin user may further include: a system admin user, the system admin user within the administration authority of each hospital institution admin user administrates role attributes of other users within administration authority of the hospital institution admin user. For example, other users administrated by the system admin user within the administration authority of each hospital institution admin user and belonging to the administration authority of the hospital institution admin user may include: a doctor user, a patient user, and a device admin user within the administration authority of each hospital institution admin user. The administrating, by the system admin user within the administration authority of each hospital institution admin user, role attributes of other users belonging to the administration authority of the hospital institution admin user, may include: assigning a role attribute to each user of the above-described other users. For example, in one example, it may be defaulted that, a role attribute of a doctor user is a first role attribute, a role attribute of a patient user is a second role attribute, and a role attribute of a device admin user is a third role attribute; when the system admin user assigns the first role attribute to a user, the user is a doctor user; when the system admin user assigns the second role attribute to a user, the user is a patient user; and when the system admin user assigns the third role attribute to a user, the user is a device admin user. Of course, it can be understood that, the role attributes listed above are merely exemplary; and in one example, the role attributes according to the embodiments of the present disclosure include but are not limited to the role attributes as listed above.

Figure 39:
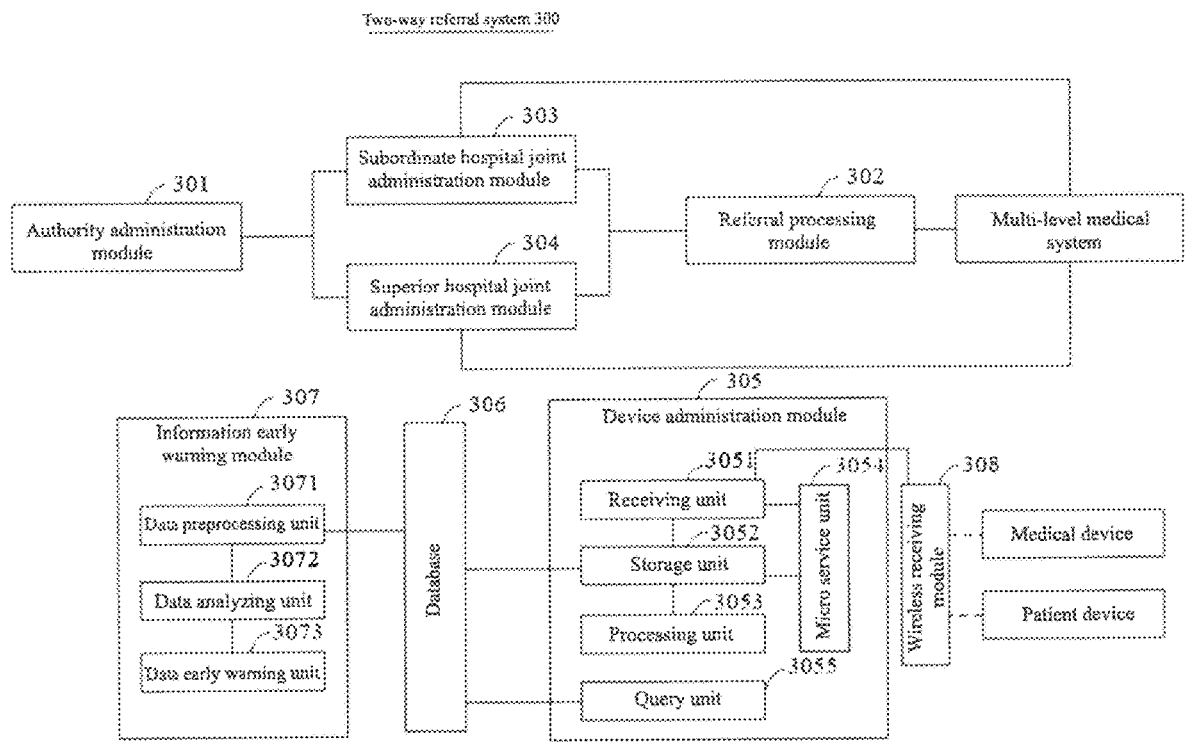
FIG. 39 is a structural block diagram of functions of another two-way referral system provided by an embodiment of the present disclosure.

In an optional mode, for example, in order to facilitate joint administration of a plurality of subordinate hospitals and to facilitate joint administration of a plurality of superior hospitals, the embodiment of the present disclosure further provides a two-way referral system 300, referring to FIG. 39, the two-way referral system 300 includes: an authority administration module 301, a referral processing module 302, a subordinate hospital joint administration module 303, and an superior hospital joint administration module 304.

For example, the subordinate hospital joint administration module 303 is configured to administrate users of a plurality of subordinate hospitals. In one example, the administrating the users of the plurality of subordinate hospitals includes: performing administration operations on information of the users of the plurality of subordinate hospitals, for example, performing administration operations on patient information of patient users of the plurality of subordinate hospitals, performing administration operations on doctor information of doctor users of the plurality of subordinate hospitals, and performing administration operations on device admin user information of device admin users of the plurality of subordinate hospitals. The superior hospital joint administration module 304 is configured to administrate users of a plurality of superior hospitals. In one example, the administrating the users of the plurality of superior hospitals includes: performing administration operations on information of the users of the plurality of superior hospitals, for example, performing administration operations on patient information of patient users of the plurality of superior hospitals, performing administration operations on doctor information of doctor users of the plurality of superior hospitals, and performing administration operations on device admin user information of device admin users of the plurality of superior hospitals. In one example, the device admin user information of the device admin user may include: information of the medical device within the administration authority of the device admin user, as well as account identity and account password, etc. registered by the device admin user during registration, and other information related to account attributes of the device admin user; for patient information, the above-described corresponding introduction to patient information may be referred to; and for doctor information, the above-described corresponding introduction to doctor information may be referred to; no details will be repeated here; and the above-described administration operations may include but are not limited to: creating, deleting, modifying, and querying.

In one example, in the subordinate hospital joint administration module 303, in order to facilitate administrating users of a plurality of subordinate hospitals, data tables having target information stored therein in the plurality of subordinate hospitals may be cascaded according to the target information, so that: when administration operations (e.g., deleting, modifying, and querying) are performed on the target information of a created (or registered) user, cascading administration operations may be specifically performed on the above-described target information, that is: a uniform administration operation is performed on the target information in all data tables containing the target information, for example, uniformly deleting the target information in all the data tables containing the target information (cascade deletion), uniformly modifying the target information in all the data tables containing the target information (cascade modification), and uniformly querying the target information in all the data tables containing the target information (cascade query), and so on. The above-described target information may include the above-described patient information, doctor information, device admin user information, and other information related to the user. In the embodiment of the present disclosure, by cascading the target information, data tables containing same information in different subordinate hospitals may be associated, which not only can effectively improve richness of information acquired when a user acquires information, but also can effectively improve efficiency of information processing through jointly administrating the information of users of the plurality of subordinate hospitals.

Similarly, in the superior hospital joint administration module 304, in order to facilitate administrating users of a plurality of superior hospitals, data tables having target information stored therein in the plurality of superior hospitals may be cascaded according to the target information (for details, the above-described corresponding introduction to the target information may be referred to; and no details will be repeated here), so that: when administration operations are performed on the target information of a created (or registered) user, cascading administration operations may be performed on the above-described target information (for details, the above-described corresponding introduction to the cascading administration operations may be referred to; and no details will be repeated here).

For example, if the above-described target information is a user identification of a patient user, data tables storing the user identification of the patient user includes: a data table 1 corresponding to case information containing the user identification of the patient user, a data table 2 corresponding to physical examination information containing the user identification of the patient user, and a data table 3 corresponding to medical device (a medical device used by the patient user) information containing the user identification of the patient user, the data table 1, the data table 2, and the data table 3 may be obtained by querying according to the user identification of the patient user, which effectively increases richness of information acquired when a user acquires information; for another example, if users with an allergic symptom are to be marked, relevant information containing the allergic symptom may be used as the above-described target information; and when a data table containing the relevant information of the allergic symptom is found according to the target information, users on all data tables may be marked, which improves information processing efficiency.

In one example, each hospital will be rated for its corresponding hospital level; the above-described hospital levels may include, in a descending order: tertiary hospitals, secondary hospitals, and primary hospitals; and in the embodiments of the present disclosure, superior hospitals may include: tertiary hospitals; and subordinate hospitals may include: secondary hospitals and primary hospitals.

The authority administration module 301 may implement the same functions as the authority administration module 101, and a difference between the two is that the authority administration module 301 is further configured to: correspond each superior hospital to a subordinate hospital belonging to the administration authority of the superior hospital. In one example, with respect to a case of two-way referral where a patient user is transferred between a subordinate hospital and a superior hospital in an administrative division to which the subordinate hospital belongs, the subordinate hospital belonging to the administration authority of the superior hospital is the subordinate hospital in an administrative division to which the superior hospital belongs, for example, a subordinate hospital within the administration authority of a superior hospitals in an area A is the subordinate hospital in the area A. In one example, when each superior hospital is corresponded to a subordinate hospital belonging to the administration authority of the superior hospital, the authority administration module 301 may establish a correspondence relationship between each superior hospital and the subordinate hospital belonging to the administration authority of the superior hospital. The patient information and doctor information of the subordinate hospital belonging to the administration authority of the superior hospital is visible to the superior hospital, and the patient information and doctor information of the superior hospital is invisible to the subordinate hospital belonging to the administration authority of the superior hospital.

The referral processing module 302 may implement the same functions as the referral processing module 102, and a difference between the two is that, a process that the referral processing module 302 receives a referral request carrying the user identification of the first doctor user and receives the query identification of the second doctor user to generate the referral request form visible to the second doctor user may specifically include that: the referral processing module 302 sends the user identification of the first doctor user and the query identification of the second doctor user to the superior hospital joint administration module 304 and the subordinate hospital joint administration module 303, if the first doctor user is a doctor user of the superior hospital, and the second doctor user is a doctor user of the subordinate hospital, the superior hospital joint administration module 304 determines a first superior hospital according to the user identification of the first doctor user, and the subordinate hospital joint administration module 303 determines a first subordinate hospital according to the query identification of the second doctor user; the first doctor user is a doctor user of the first superior hospital, and the second doctor user is a doctor user of the first subordinate hospital; thereafter, the authority administration module 301 determines whether the first subordinate hospital is a subordinate hospital corresponding to the first superior hospital, for example, the authority administration module 301 may determine whether the first subordinate hospital is a subordinate hospital corresponding to the first superior hospital, according to the corresponding relationship established between each superior hospital and a subordinate hospital belonging to the administration authority of the superior hospital; and when the authority administration module 301 determines that the first subordinate hospital is the subordinate hospital corresponding to the first superior hospital, the authority administration module 301 sends, to the referral processing module 302, a confirmation message that the first subordinate hospital is the subordinate hospital corresponding to the first superior hospital; and when receiving the confirmation message that the first subordinate hospital is the subordinate hospital corresponding to the first superior hospital sent by the authority administration module 301, the referral processing module 302 generates the referral request form visible to the second doctor.

If the first doctor user is a doctor user of a subordinate hospital, and the second doctor user is a doctor user of a superior hospital, the referral processing module 302 sends the user identification of the first doctor user and the query identification of the second doctor user to the superior hospital joint administration module 304 and the subordinate hospital joint administration module 303, so that the subordinate hospital joint administration module 303 determines a second subordinate hospital according to the user identification of the first doctor user, and the superior hospital joint administration module 304 determines a second superior hospital according to the query identification of the second doctor user, the first doctor user is a doctor user of the second subordinate hospital, and the second doctor user is a doctor user of the second superior hospital; thereafter, the authority administration module 301 determines whether the second subordinate hospital is a subordinate hospital corresponding to the second superior hospital, for example, the authority administration module 301 may determine whether the second subordinate hospital is a subordinate hospital corresponding to the second superior hospital, according to the corresponding relationship established between each superior hospital and a subordinate hospital belonging to the administration authority of the superior hospital; when determining that the second subordinate hospital is the subordinate hospital corresponding to the second superior hospital, the authority administration module 301 sends, to the referral processing module 302, a confirmation message that the second subordinate hospital is the subordinate hospital corresponding to the second superior hospital; and when receiving the confirmation message that the second subordinate hospital is the subordinate hospital corresponding to the second superior hospital sent by the authority administration module 301, the referral processing module 302 generates the referral request form visible to the second doctor.

When a patient user is transferred between different hospital institutions, the first doctor user and the second doctor user belong to different hospital institutions. In an optional mode, referring to FIG. 38A, when a doctor user A11 administrates a patient user A21 and a patient user A22, the doctor user A11 wants to transfer the patient user A22 to a hospital B (corresponding to the hospital institution admin user B in FIG. 38A), at this time, a doctor user B1 is invisible to the doctor user A11; the doctor user A11 may find the doctor user B1 through the mobile phone number, and then fill in a referral reason, select a patient user A22 to be referred, and submit a referral request form, and the referral request form is visible to the doctor user B1; when the doctor user B1 feeds back a referral request confirmation message according to the referral request form, in this case, the patient user A22 is not only visible to the doctor user A11, but also visible to the doctor user B1, and the patient user A22 is not only a user within the administration authority of the doctor user A11, but also a user within the administration authority of the doctor user B1.

In another optional mode, referring to FIG. 38B, when the doctor user A11 administrates the patient user A21 and the patient user A22, the doctor user A11 wants to transfer the patient user A22 to a hospital B (corresponding to a hospital institution admin user B in FIG. 38B), at this time, the doctor user B1 is invisible to the doctor user A11, the doctor user A11 may find the doctor user B1 through the mobile phone number, and then fill in a reason referral, select the patient user A22 to be referred, submit a referral request form, the referral request form is visible to the doctor user B1; and when the doctor user B1 feeds back a referral request confirmation message according to the referral request form, the patient user A22 is invisible to the doctor user A11, and meanwhile, the patient user A22 is visible to the doctor user B1; the patient user A22 is no longer a user within the administration authority of the doctor user A11, but a user within the administration authority of the doctor user B1.

When the doctor user B1 feeds back the referral request confirmation message according to the referral request form, for the patient user A22, a solid line in FIG. 38A and FIG. 38B indicates the existence of the administration authority with respect to the patient user A22 (and meanwhile is visible to the patient user A22), and a dotted line indicates that the administration authority with respect to the patient user A22 does not exist (and meanwhile is invisible to the patient user A22).

The above-described referral process not only implements a cross-administration authority referral function, but also maintains isolation of data.

In an optional mode, for example, medical measurement devices may include patient devices of patients and the above-described medical devices. In one example, with respect to some patient users with chronic respiratory disease, medical measurement devices are usually needed to monitor physiological data of the users for a long time; for example, with respect to a patient user with chronic obstructive pulmonary disease (COPD), it is usually necessary to monitor the physiological data corresponding to the patient user through a ventilator and a pulmonary function instrument; when the patient user with chronic disease is transferred, it is also usually necessary to transmit the above-described physiological data of the user who has been monitored for a long time to the referred doctor user; however, the amount of the physiological data of the user who has been monitored for a long time is usually large, which brings much inconvenience to the transmission process; and in order to solve the above-described problems, referring to FIG. 39, the two-way referral system 300 may further include: a device administration module 305. For example, the device administration module 305 includes: a receiving unit 3051, a storage unit 3052, a processing unit 3053, a micro service unit 3054, and a query unit 3055.

The receiving unit 3051 is configured to receive a medical measurement report uploaded by a medical measurement device, information of the medical measurement report at least includes: physiological parameters of a target patient user collected by the medical measurement device, and the target patient user is any one of the patient users.

The storage unit 3052 is configured to store the above-described medical measurement report.

For example, after receiving the medical measurement report uploaded by the medical measurement device, the storage unit 3052 may store the above-described medical measurement report. In one example, the above-described medical measurement report may be stored in a local database 306.

For example, when the storage unit 3052 stores the medical measurement report uploaded by the medical measurement device, the storage unit 3052 may store all information of the medical measurement report uploaded by the medical measurement device, or may also selectively store the information of the medical measurement report uploaded by the medical measurement device according to levels of importance of various types of information among the information of the medical measurement report uploaded by the medical measurement device. In one example, because real-time data usually has a higher reference value, when storing the medical measurement report uploaded by the medical measurement device, the storage unit 3052 may cache first information of the medical measurement report uploaded by the medical measurement device, an acquisition period of the first information is less than a first threshold. Among them, the information of the medical measurement report includes physiological parameter of the target patient user collected by the medical measurement device.

In one example, because real-time data collected within a period of time or data collected at a higher frequency (i.e., the acquisition period is less than the first threshold) within a period of time usually has a higher reference value, in order to acquire the above-described data (i.e., first information) with a higher reference value, the first information whose acquisition period is less than the first threshold may be cached, so that the first information may be supplied to a user for reference, or subsequent analysis processing is performed on the above-described data with a higher reference value to evaluate the user's health condition or generate an early warning message related to the user's health condition, etc. For example, with respect to a patient with respiratory disease, real-time data such as expiratory pressure, inspiratory pressure, and respiration frequency of the patient user acquired in real time usually has a high reference value, then the real-time data such as expiratory pressure, inspiratory pressure, and respiration frequency of the patient user monitored by the ventilator in real time can be cached, so that the user's health condition may be evaluated subsequently based on the above-described cached data or an early warning message related to the user's health condition may be generated to assist the user in monitoring the condition.

For example, at least one embodiment of the present disclosure provides a data collection module; and the data collection module has a patient personalized data query function and a personalized data classification function. For example, with respect to personalized data query, desired data may be quickly filtered out from the database by a specific query condition, for example, detection records of a patient over a period of time may be quickly indexed out according to keywords such as name, age, and disease characteristics of the patient, type of device used, and report date.

For example, the personalized data classification refers to automatically binding the data generated by the device to the patient by operating the device, and updating the real-time data of the patient with very low latency; for example, a certain brand of ventilator may be bound to the patient user identification according to a unique identification serial number (SN) of the device, so as to quickly bind high-frequency real-time data generated by the ventilator to the corresponding patient user.

For example, the data collection module has a personalized data cache function.

The data collection module according to at least one embodiment of the present disclosure allows the storage module to adopt a multi-level cache mechanism (or a data hierarchical storage mechanism) when storing the data collected by the data collection module. For example, the data collection module classifies the collected data, and allocates different levels of data to memories of corresponding levels, respectively.

For example, the data collection module may classify the collected data based on patients' personal situations (severity of illness conditions of patients), degrees of importance of data, the memory space to be occupied by data, and frequencies of querying patients' past data, put high-level data in a high-speed memory (e.g., cache), put medium-level data in a medium-speed memory (e.g., a random access memory), and put low-level data in a low-speed memory (e.g., a read-only memory or a fixed memory).

For example, by adopting the multi-level cache mechanism (or the data hierarchical storage mechanism), high-frequency query data can be cached, and selectively perform a write operation on important low-frequency data, which, thus, not only speeds up a query speed and an analysis speed, and improves timeliness of an early warning module, but also improves database communication efficiency and ensures high reliability and high availability of important data.

For example, before caching, respective types of data (e.g., data reports) are classified by importance level and query frequency according to patients' personal situations and data types of patients' devices; and data reports of different levels of importance and query frequencies are respectively cached, which may accelerate a data query speed and an early warning speed (e.g., a speed of generating early warning information based on the above-described data), thereby enhancing real-time performance of the chronic disease administration system (e.g., the health administration apparatus).

At the same time, the storage unit 3052 is further configured to: acquire third information matching a preset keyword in second information, and store the third information, an acquisition period of the second information is greater than a second threshold. In one example, the second information may be locally stored low-frequency data (data whose acquisition period is greater than the second threshold), for example, information changing at a low frequency, such as height and weight of a patient user, and a physical examination report of a patient user (generally, a user undergoes a physical examination once a year to acquire a corresponding physical examination report), etc. In one example, the above-described low-frequency data usually contains some high-reliability high-availability data; and therefore, in one example, in order to extract the above-described high-reliability high-availability data from the second information, a preset keyword may be set, and then the third information matching the preset keyword in the second information is acquired as the above-described high-reliability high-availability data, and the above-described third information is stored. In one example, the above-described high-reliability high-availability data may be extracted from the second information by many methods, for example, the above-described third information is extracted, by using an optical character recognition (OCR) technology, from a picture (e.g., a picture of a physical examination report taken by a user with a mobile phone camera) containing the second information and stored locally. In one example, the preset keyword may be set by a user according to actual situations.

In this way, adopting the multi-level cache mechanism, respective types of data reports are classified by importance level and query frequency according to patients' personal situations and data types of patients' devices before caching, and data reports of different levels of importance and query frequencies are cached, respectively, which may greatly accelerate an early warning speed and a query speed and enhance real-time performance of the system. A write operation is selectively performed on important low-frequency data, which improves database communication efficiency and ensures high reliability and high availability of important data.

In one example, the first threshold and the second threshold may be set by those skilled in the art according to actual situations, and will not be limited in the embodiments of the present disclosure.

The receiving unit 3051 is further configured to receive an association request carrying a device identification of the medical measurement device and the user identification of the target patient user.

The processing unit 3053 is configured to associate information of the medical measurement report uploaded by the medical measurement device with the target patient user according to the device identification of the medical measurement device and the user identification of the target patient user, when the receiving unit 3051 receives the association request carrying the device identification of the medical measurement device and the user identification of the target patient user. The above-described association request may be sent by a doctor user or a target patient user; the device identification of the medical measurement device is specifically identification information that can uniquely identify the medical measurement device, for example, a product serial number (SN) of the medical measurement device; the user identification of the target patient user is specifically identification information that can uniquely identify the patient user, for example, identification (ID) number of the patient user; when associating the information of the medical measurement report uploaded by the medical measurement device with the target patient user, the information of the medical measurement report uploaded by the medical measurement device may be bound to the target patient user, for example, the SN code of the medical measurement device is bound to the ID of the patient user, and then the medical measurement report uploaded by the medical measurement device is associated with the patient user according to the above-described binding relationship.

Before the device administration module 305 receives the medical measurement report uploaded by the medical measurement device, the device administration module 305 firstly needs to establish a connection with the medical measurement device. In one example, in an optional mode, the device administration module 305 may be directly connected with the medical measurement device through a wireless connection manner, and then the embodiment of the present disclosure further includes: a wireless receiving module 308, configured to receive a first connection request sent by the medical measurement device, and establish a wireless connection between the device administration module 305 and the medical measurement device according to the first connection request; in one example, the above-described wireless connection may be a Bluetooth connection, a wireless local area network WIFI connection, and the like.

Considering that data exchange formats of information of medical measurement reports uploaded by different medical measurement devices are diverse, in order to facilitate unified administration of the information of the uploaded medical measurement reports, the device administration module 305 may also include: a micro service unit 3054, configured to convert, after the receiving unit receives a medical measurement report, whose information is in a first data exchange format, uploaded by a medical measurement device, a data exchange format of the above-described medical measurement report from the first data exchange format to a target data exchange format corresponding to a type of the medical measurement device, according to the type of the medical measurement device, in order to facilitate unifying data exchange formats of medical measurement reports as the target data exchange format, so as to achieve the purpose of unified administration of the information of the uploaded medical measurement reports.

In one example, the exchange format of the information uploaded by the medical measurement device is converted into the target data exchange format corresponding to the type of the medical measurement device according to the type of the medical measurement device, data interaction logic thereof is encapsulated, and a document database is adopted for achieving the data persistence, so as to implement unified storage and administration of data of a variety of different devices. The target data exchange format is set by those skilled in the art according to actual situations, which will not be limited in the embodiment of the present disclosure.

In one example, the device administration module 305 further includes: a query unit 3055, configured to acquire a query identification information input by a user, query the database 306 according to the query identification information, and acquire information containing the query identification information and corresponding to the above-described query identification information. In one example, the above-described query identification information may be information such as a keyword that needs to be queried and input by the user according to actual needs. By specific query conditions, the required data may be quickly screened out from the database, for example, detection records of a patient over a period of time may be quickly indexed out according to keywords such as name, age, and disease characteristics of the patient, type of device used, and report date.

In an optional mode, for example, the two-way referral system 300 may further include: an information early warning module 307; the information early warning module 307 is connected with the device administration module 305, and is configured to analyze the information of the medical measurement report and determine, according to the analysis result, whether to generate an early warning message. In one example, the information early warning module 307 may include:

A data preprocessing unit 3071, configured to preprocess the information of the medical measurement report and generate a preprocessing result. In one example, the information of the medical measurement report may be preprocessed according to many methods, for example, performing statistics on the first information in the medical measurement device report (e.g., data queried at a high frequency or real-time data), and filling default data, and so on. A method for filling the default data may be set by those skilled in the art according to actual situations, which will not be limited in the embodiment of the present disclosure.

A data analyzing unit 3072, configured to analyze a preprocessing result of the data preprocessing unit 3071, and generate an analysis result. In one example, there may be many methods to analyze the preprocessing results, for example, acquiring information of a previously acquired historical medical measurement report of a target patient user according to a user identification of the target patient user, and analyzing the user in combination with the information of the historical medical measurement report and personal health information; the above-described method of analyzing the user may be set by those skilled in the art according to actual situations, which will not be limited in the embodiment of the present disclosure; and each piece of data in the analysis result may be input to a corresponding preset early warning analyzing model of the data early warning unit 3073 to generate an early warning result.

A data early warning unit 3073, configured to determine whether to generate an early warning message according to the analysis result of the data analyzing unit 3027. In one example, the data early warning unit 3073 may include a plurality of preset early warning analyzing models; after the data early warning unit 3073 receives the analysis result input by the data analyzing unit 3072, the data early warning unit 3073 may automatically match the above-described analysis result to a preset early warning analyzing model corresponding to the analysis result, and inputs the analysis result into the preset early warning analyzing model; the preset early warning analyzing model generates an early warning analysis result; and the above-described early warning analysis result at least includes: an early warning message generated to remind a user that there is an early warning situation about his/her health status, or a none-illness message generated to remind a user that there is no early warning situation about his/her own health status.

There may be many methods to analyze the information of the medical measurement report, for example, performing threshold analysis on the information of the medical measurement report, performing statistical analysis on the information of the medical measurement report, and so on; and a method of analyzing the information of the medical measurement report will not be limited in the embodiment of the present disclosure. In one example, the information early warning module 307 may further generate an analysis result report, which contains the analysis result of analyzing the information of the medical measurement report; and the analysis result may be used as a reference basis for the doctor user to make a referral decision for the target patient user.

For example, by making the two-way referral system 300 further include an information early warning module 307, the information early warning module 307 may be allowed to assess the patient's current physical condition and provide decision-making assistance opinions for referral. For example, in a case where the information early warning module 307 generates an early warning of a aggravation illness condition with respect to a certain patient, priority of a referral request (referral from a subordinate hospital to a superior hospital) with respect to the patient in the referral processing module 302 may be raised, or the system automatically initiates a request for referral from a subordinate hospital to a superior hospital, so that the patient may receive diagnosis and treatment services that match his/her illness condition. In this case, timeliness of referral may be improved and possibility of delays in the patient's illness condition may be reduced.

For example, the patient device includes a patient's own medical device and a hospital's outpatient medical device, and includes a ventilator, a pulmonary function instrument, and other instruments that can measure health data of the patient; a patient uses a device to measure and diagnose his/her own illness conditions, to form measurement records and reports; for a medical device owned by the patient, the report will be automatically bound to the patient user; and for a hospital's outpatient medical device, the report is bound to the patient by a doctor. Different medical devices generally have different business logics, for example, a ventilator may have real-time data and non-real-time data. Due to diversity in service logic and message formats, a micro-service architecture is adopted to formulate independent interaction standards for each category of devices, data interaction logic thereof is encapsulated, and a document database is adopted for achieving the data persistence, so as to implement unified storage and administration of a variety of different types of device data. For example, the patient device administration module is caused to adopt the micro-service structure, which may provide a corresponding independent service for each different type of smart terminals, implement a workflow of independent service, independent development, and independent deployment, and establish a unified standard for the data formats of the devices, thereby improving scalability and stability of the system.

For example, the referral processing module further includes a referral form queue, a retrieval system, and referral form format design. The referral form queue is configured to store a referral request initiated by a doctor; the retrieval system is configured to quickly lock a target referral doctor under various user frameworks; and the referral form format design includes design of respective fields of the referral form in the system.

For example, a doctor of a transfer-out hospital retrieves a doctor user of a receiving hospital through a mobile phone number, selects a patient user to be diagnosed, and fills in a referral reason to initiate referral; and the referral form will be added to a referral form queue of the doctors in the receiving hospital.

For example, the receiving hospital confirms the referral form after receiving the referral message, completely mounts the user to be referred under an authority tree node of a current receiving user, and releases data and operation authority with respect to the patient user.

Figure 40:
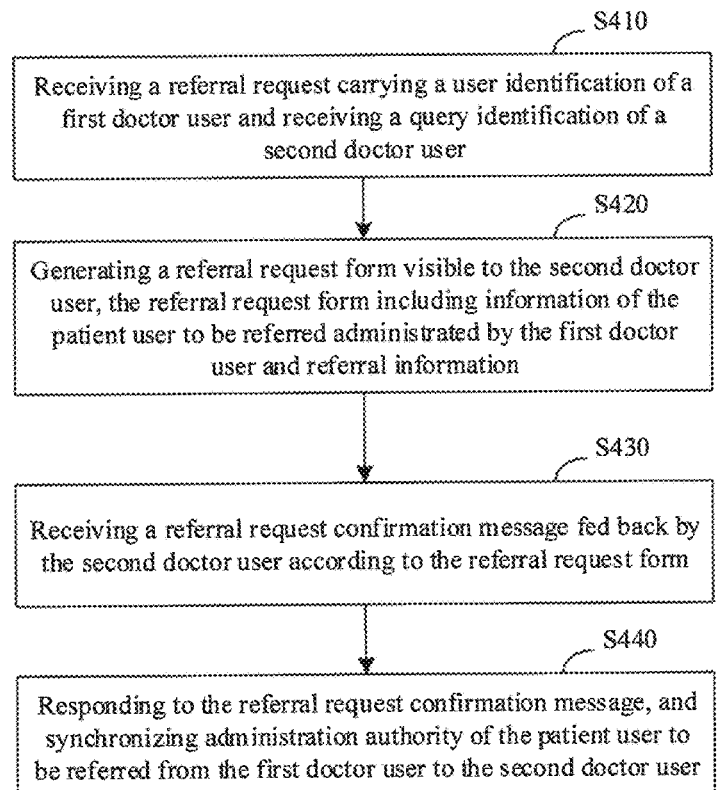
FIG. 40 is a method flow chart of an administration method of the two-way referral system provided by the embodiment of the present disclosure.

An embodiment of the present disclosure further provides an administration method of a two-way referral system, the two-way referral system includes users of a plurality of levels; the users of the plurality of levels include patient users and doctor users, a level of a doctor user is higher than a level of a patient user, and the doctor user administrates the patient user belonging to the administration authority of the doctor user; referring to FIG. 40, the administration method of the two-way referral system provided by the embodiment of the present disclosure includes:

Step S410: receiving a referral request carrying a user identification of a first doctor user and receiving a query identification of a second doctor user.

Step S420: generating a referral request form visible to the second doctor user, the referral request form including information of the patient user to be referred administrated by the first doctor user and referral information.

Step S430: receiving a referral request confirmation message fed back by the second doctor user according to the referral request form.

Step S440: responding to the referral request confirmation message, and synchronizing administration authority of the patient user to be referred from the first doctor user to the second doctor user.

In an optional mode, in the administration method of the two-way referral system provided by the embodiment of the present disclosure, a role attribute of a user may be administrated.

Figure 41:
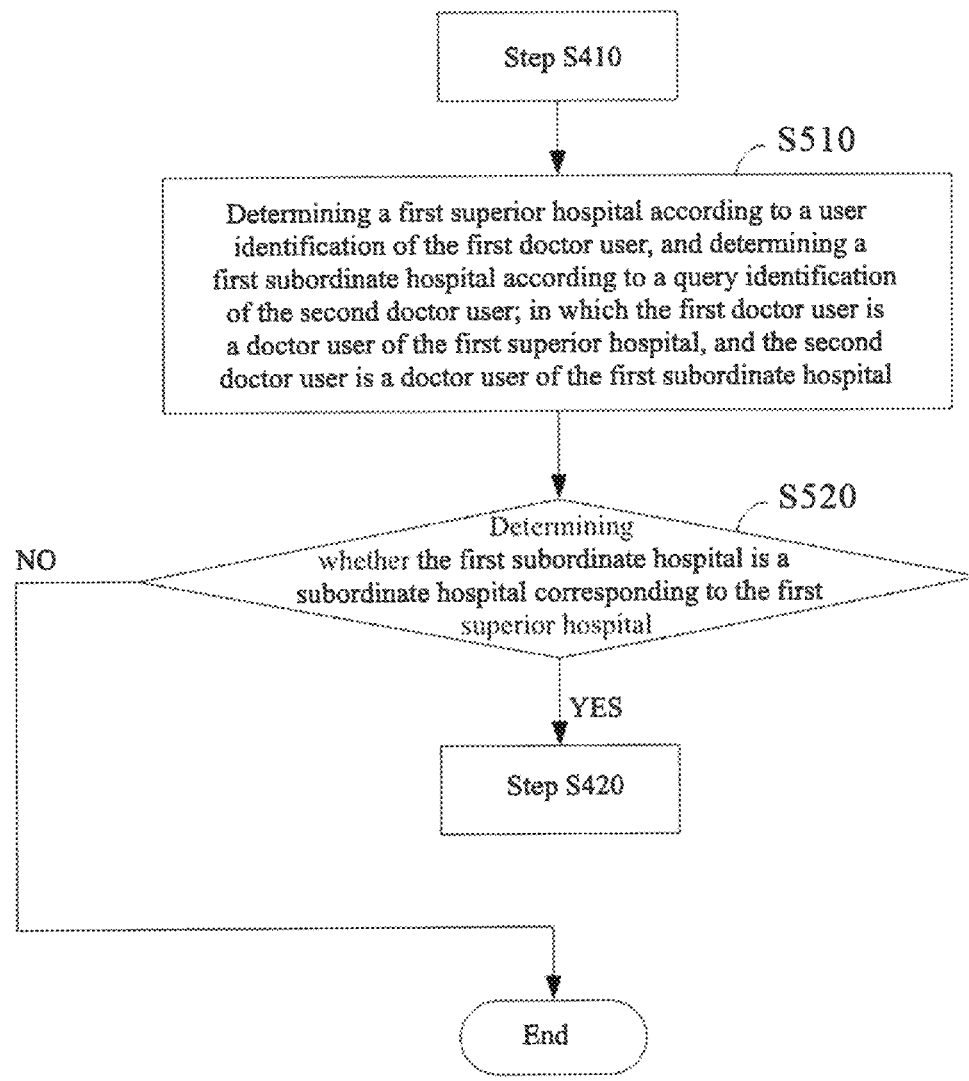
FIG. 41 is a method flow chart of an administration method of the two-way referral system provided by the embodiment of the present disclosure.

In an optional mode, in the administration method of the two-way referral system provided by the embodiment of the present disclosure, doctor users may include: a doctor user of at least one subordinate hospital and a doctor user of at least one superior hospital; and patient users may include: a patient user of at least one subordinate hospital and a patient user of at least one superior hospital. If the first doctor user is a doctor user of a superior hospital, and the second doctor user is a doctor user of a subordinate hospital, then after executing step S410, referring to FIG. 41, the embodiment of the present disclosure may further execute the following steps of:

Step S510: determining a first superior hospital according to a user identification of the first doctor user, and determining a first subordinate hospital according to a query identification of the second doctor user; in which the first doctor user is a doctor user of the first superior hospital, and the second doctor user is a doctor user of the first subordinate hospital.

Step S520: determining whether the first subordinate hospital is a subordinate hospital corresponding to the first superior hospital, if yes, executing step S420; if not, ending this process.

Figure 42:
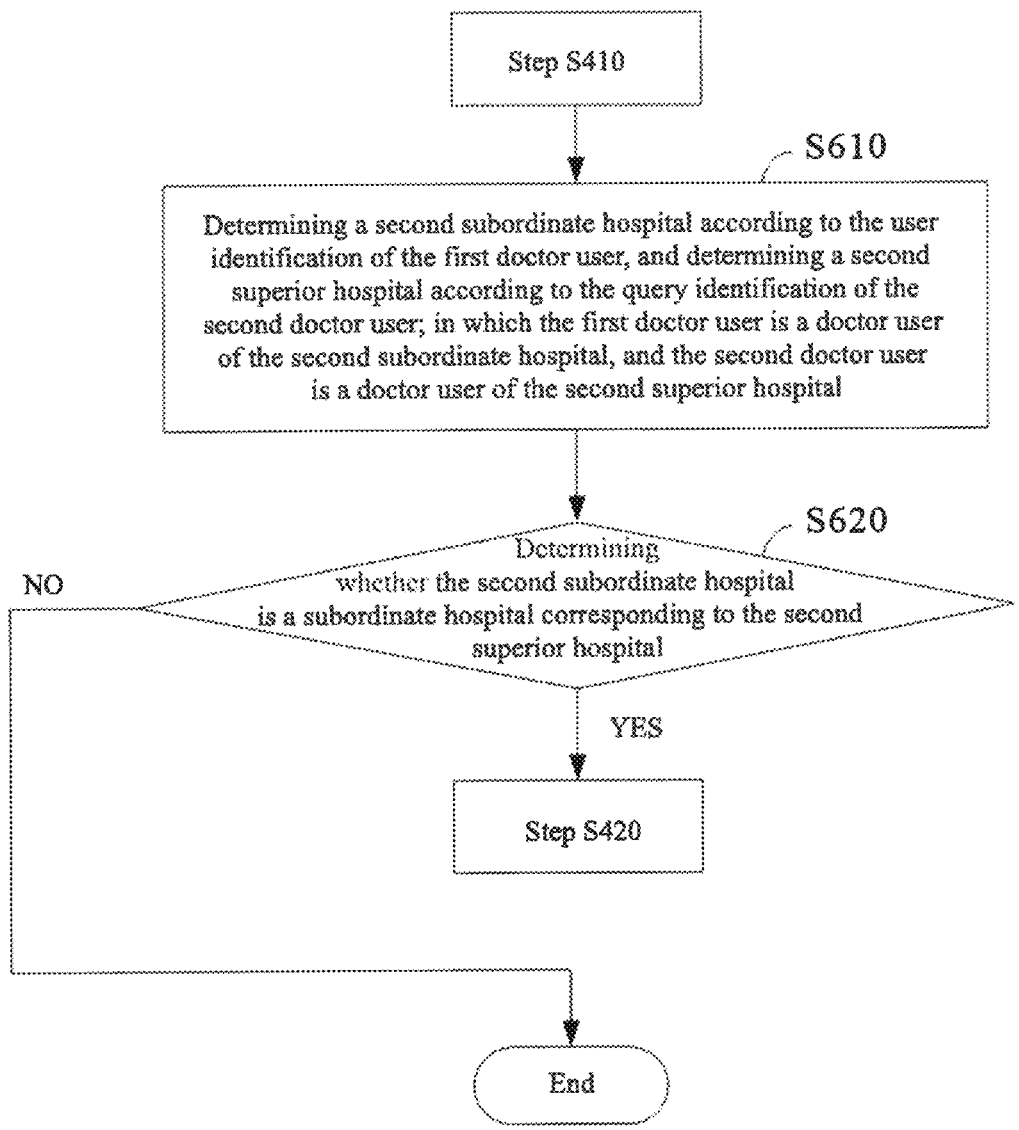
FIG. 42 is a method flow chart of an administration method of another two-way referral system provided by an embodiment of the present disclosure.

If the first doctor user is a doctor user of a subordinate hospital, and the second doctor user is a doctor user of a superior hospital, then after executing step S410, referring to FIG. 42, the embodiment of the present disclosure may also execute the following steps of:

Step S610: determining a second subordinate hospital according to the user identification of the first doctor user, and determining a second superior hospital according to the query identification of the second doctor user; in which the first doctor user is a doctor user of the second subordinate hospital, and the second doctor user is a doctor user of the second superior hospital.

Step S620: determining whether the second subordinate hospital is a subordinate hospital corresponding to the second superior hospital, if yes, executing step S420; if not, ending this process.

Figures 43, 44:
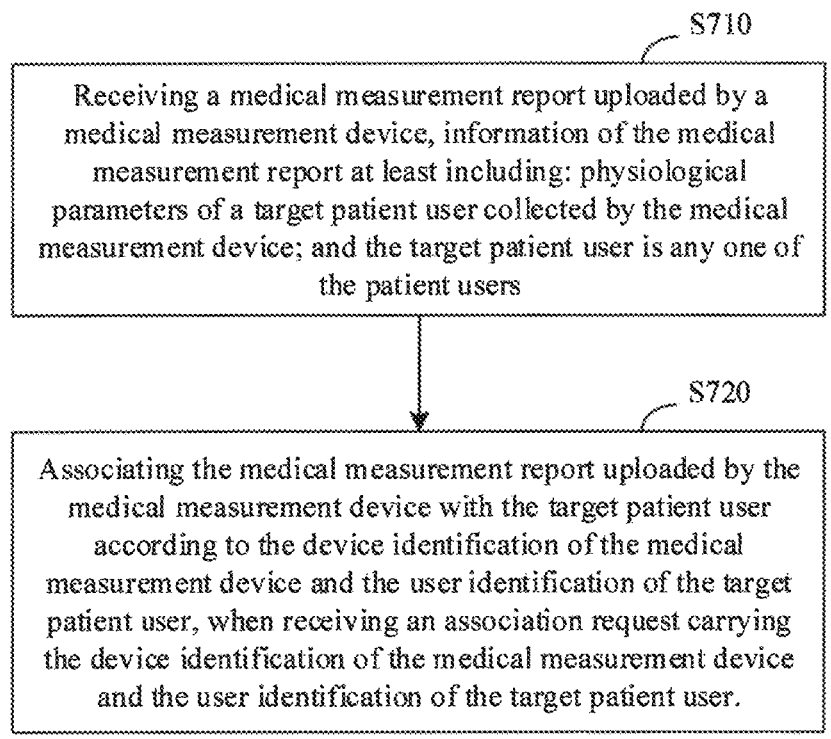
FIG. 43 is a method flow chart of an administration method of still another two-way referral system provided by an embodiment of the present disclosure.
FIG. 44 is a method flow chart of an administration method of still another two-way referral system provided by an embodiment of the present disclosure.

Further, referring to FIG. 43, the administration method of the two-way referral system provided by the embodiment of the present disclosure further includes:

Step S710: receiving a medical measurement report uploaded by a medical measurement device, information of the medical measurement report at least including: physiological parameters of a target patient user collected by the medical measurement device; and the target patient user is any one of the patient users.

Step S720: associating the medical measurement report uploaded by the medical measurement device with the target patient user according to the device identification of the medical measurement device and the user identification of the target patient user, when receiving an association request carrying the device identification of the medical measurement device and the user identification of the target patient user.

In an optional mode, after executing step S710, referring to FIG. 44, the embodiment of the present disclosure may further execute the following steps of:

Step S730a: caching first information of the medical measurement report uploaded by the medical measurement device, in which an upload period of the first information is less than a first threshold.

Step S730b: acquiring third information matching a preset keyword in second information, and storing the third information, in which an acquisition period of the second information is greater than a second threshold.

Step S730a and step S730b may be executed synchronously.

Figure 45:
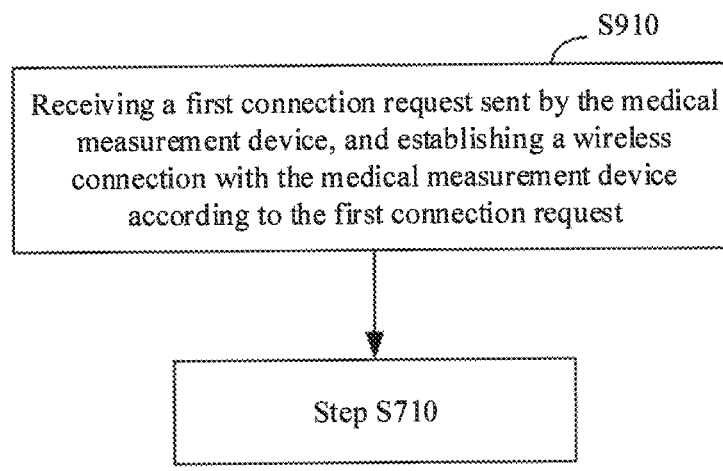
FIG. 45 is a method flow chart of an administration method of yet another two-way referral system provided by an embodiment of the present disclosure.

In an optional mode, referring to FIG. 45, before executing step S710, the embodiment of the present disclosure may further execute the following steps of:

Step S910: receiving a first connection request sent by the medical measurement device, and establishing a wireless connection with the medical measurement device according to the first connection request.

Figure 46:
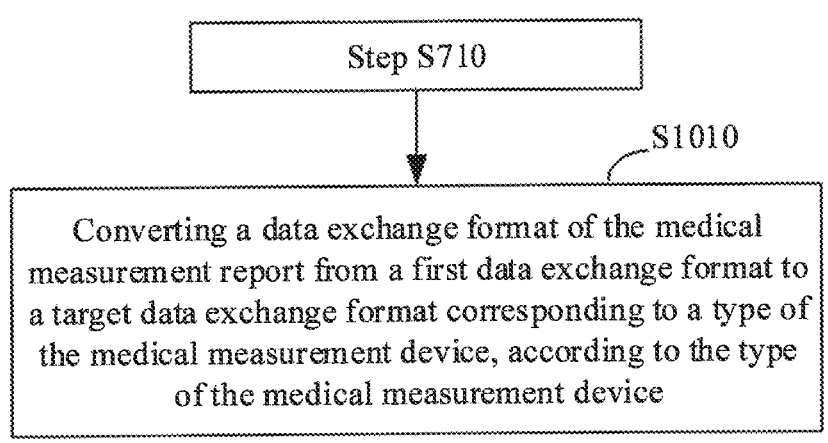
FIG. 46 is a method flow chart of an administration method of yet another two-way referral system provided by an embodiment of the present disclosure.

In an optional mode, referring to FIG. 46, after executing step S710, the embodiment of the present disclosure may further execute the following steps of:

Step S1010: converting a data exchange format of the medical measurement report from a first data exchange format to a target data exchange format corresponding to a type of the medical measurement device, according to the type of the medical measurement device.

Figure 47:
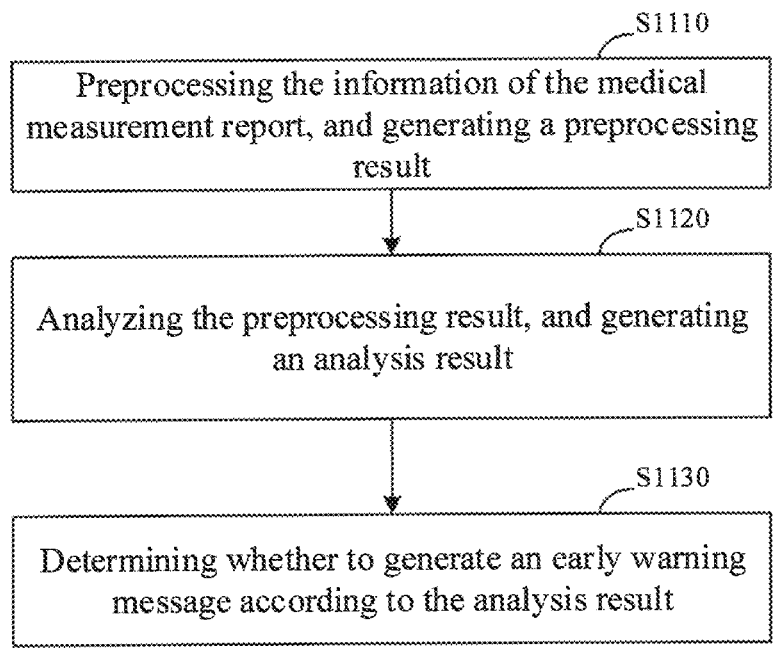
FIG. 47 is a method flow chart of an administration method of yet another two-way referral system provided by an embodiment of the present disclosure.

In an optional mode, referring to FIG. 47, after executing step S720, the embodiment of the present disclosure may further execute the following steps of:

Step S1110: preprocessing the information of the medical measurement report, and generating a preprocessing result.

Step S1120: analyzing the preprocessing result, and generating an analysis result.

Step S1130: determining whether to generate an early warning message according to the analysis result.

For all relevant contents of the respective steps involved in the above-described method embodiments, the functional descriptions of the corresponding functional modules in the above-described two-way referral system may be cited and referred to, and functions and beneficial effects will not be repeated here.

In a case where an integrated module is adopted, the two-way referral system includes: a processing unit and an interface unit. The processing unit is configured to control and administrate actions of the two-way referral system, for example, the processing unit is configured to execute computer programs or instructions to implement the functions of the two-way referral system. The interface unit is configured to support the interaction between the two-way referral system and other apparatus, for example, interaction with a medical measurement device. The two-way referral system may further include a storage unit, configured to store computer programs or instructions of the two-way referral system.

Figure 48:
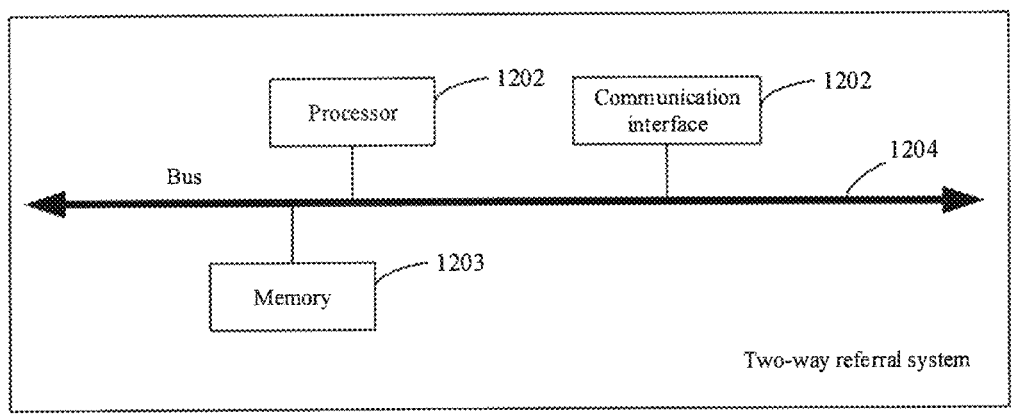
FIG. 48 is a structural block diagram of functions of another two-way referral system provided by an embodiment of the present disclosure.

By taking the processing unit as a processor and the interface unit as a communication interface as an example, the two-way referral system shown in FIG. 48 includes a communication interface 1201 and a processor 1202; the communication interface 1201 and the processor 1202 are coupled; exemplarily, the communication interface 1201 and the processor 1202 may be coupled through a bus 1204.

The processor 1202 may be a general-purpose central processing unit (CPU), a controller, an application-specific integrated circuit (ASIC), or one or more integrated circuits used to control execution of the programs of the solution of the present disclosure.

Of course, the processor 1202 may further be integrated therewith a storage apparatus storing the computer programs or instructions of the two-way referral system; or the storage apparatus may also be provided separately; for example, as shown in FIG. 48, a separately provided memory 1203 stores the computer programs or instructions of the two-way referral system. The memory 1203 may be a read-only memory (ROM) or other types of static storage devices that can store static information and instructions, a random access memory (RAM) or other types of dynamic storage devices that can store information and instructions, or may also be electrically erasable programmable read-only memory (EEPROM), compact disc read-only memory (CD-ROM) or other CD memory, optical disc memory (including compact discs, laser discs, optical discs, digital versatile discs, Blu-ray discs, etc.), magnetic disk storage media or other magnetic storage devices, or may also be any other medium that can be used to carry or store desired program codes in a form of instruction or data structure and can be accessed by a computer, but the present disclosure is not limited thereto. The memory may exist independently and is connected with the processor through a bus; the memory may also be integrated with the processor. The memory 1203 is configured to store computer programs or instructions for executing the solution of the present disclosure; and the execution is controlled by the processor 1202.

The communication interface 1201 is configured to support interaction between the two-way referral system and other apparatus, for example, interaction with a medical measurement device. The processor 1202 is configured to execute computer programs or instructions stored in the memory 1203, so as to implement the methods according to the embodiments of the present disclosure.

A person of ordinary skill in the art can understand that: all or part of the steps in the above-described method embodiments may be implemented by program instruction-related hardware; the foregoing program may be stored in a computer-readable storage medium; when the program is executed, the steps including the above-described method embodiments are executed; and the foregoing storage medium includes: ROM, RAM, magnetic disk, or optical disk, and various other media that can store program codes.

At least one embodiment of the present disclosure provides a health administration method, which involves a plurality of objects and a plurality of devices and includes: generating a device usage record of at least one object based at least on identity information of the at least one object among the plurality of objects and data generated by a device used by the at least one object, and providing the device usage record of the at least one object to a memory associated with the health administration apparatus.

Figure 54:
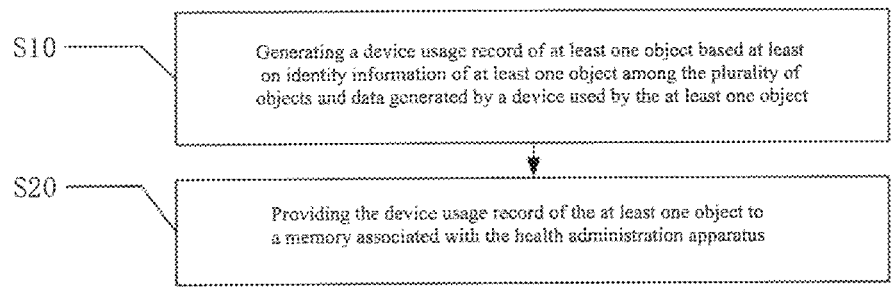
FIG. 54 is a schematic flow chart of a health administration method provided by at least one embodiment of the present disclosure.

FIG. 54 is a schematic flow chart of a health administration method provided by at least one embodiment of the present disclosure. As shown in FIG. 54, the health administration method includes the following step S10 and step S20.

Step S10: generating a device usage record of at least one object based at least on identity information of at least one object among the plurality of objects and data generated by a device used by the at least one object.

Step S20: providing the device usage record of the at least one object to a memory associated with the health administration apparatus.

In a first example, step S10 includes the following step S111 to step S114.

Step S111: acquiring a first identification code of a current object among the plurality of objects and an identification code of a first current device, the first current device being a device that has been used by the current object.

Step S112: using the identification code of the first current device to query the memory associated with the health administration apparatus, to acquire latest device-related data originating from the first current device and transferred to the memory.

Step S113: using the first identification code of the current object to query the memory, to acquire identity information of the current object.

Step S114: associating the identity information of the current object with the latest device-related data, to generate the device usage record of the current object.

For example, the acquiring the first identification code of the current object among the plurality of objects and the identification code of the first current device includes: acquiring the first identification code of the current object and the identification code of the first current device from an object service module of a terminal for the current object.

For example, step S111 to step S114 may be executed in an order of step S111, step S112, step S113, and step S114. For another example, step S111 to step S114 may be executed in an order of step S111, step S113, step S112, and step S114. For another example, step S111 to step S114 may be executed in an order of step S111, step S112+step S113 (i.e., step S112 and step S113 being executed simultaneously), and step S114.

For example, in the first example, the health administration method further includes step S115.

Step S115: generating a barcode of the first current device based on the identification code of the first current device.

For example, step S115 may be executed before step S111. For example, a device administrator may print a barcode (e.g., a two-dimensional code) of the first current device generated based on the identification code of the first current device and post the barcode of the first current device on the first current device. For example, after the barcode of the first current device has been posted to the first current device, there is no need to execute step S115.

For example, in the first example, the health administration method further includes step S116.

Step S116: using the object service module to acquire the identification code of the first current device by a barcode scanner scanning the barcode of the first current device.

For example, an object (e.g., a patient currently seeking medical consultation) may use the object service module to acquire the identification code of the first current device by scanning the barcode of the first current device by the barcode scanner. For example, step S116 may be executed before step S111 and after step S115.

For example, in the first example, the health administration method further includes step S117.

Step S117: making the first current device allow the device-related data generated by the first current device to be transferred to the memory via a third-party platform.

For example, step S117 may be executed before step S116 and after step S115, that is, the device-related data generated by the first current device is firstly transferred to the memory via the third-party platform; then the object (e.g., the patient currently seeking medical consultation) uses the object service module to acquire the identification code of the first current device by scanning the barcode of the first current device by the barcode scanner; and the object service module provides the acquired identification code of the first current device to the memory, and associates the identification code of the first current device with the first identification code of the current object.

It should be noted that, the device-related data generated by the first current device may also be transferred to the memory associated with the health administration apparatus via other applicable methods.

For example, for specific implementation modes or specific descriptions of the first identification code of the current object, the identification code of the first current device, the first current device, the memory associated with the health administration apparatus, and step S111 to step S117, the embodiment shown in FIG. 4 may be referred to, and no details will be repeated here.

In a second example, step S10 includes the following step S121 to step S123.

Step S121: acquiring the first identification code of the current object among the plurality of objects and an identification code of a second current device; the second current device being a device to be used by the current object.

Step S122: using the first identification code of the current object to query the memory associated with the health administration apparatus, so as to acquire the identity information of the current object, and creating a correspondence relationship between the identity information of the current object and the second current device.

Step S123: in a case where a data receiver associated with the health administration apparatus receives device-related data originating from the second current device, associating the identity information of the current object with the device-related data, so as to generate the device usage record of the current object.

For example, the acquiring the first identification code of the current object among the plurality of objects and the identification code of the second current device includes: acquiring the first identification code of the current object and the identification code of the second current device from the object service module of the terminal for the current object.

For example, step S121 to step S123 may be executed in an order of step S121, step S122, and step S123.

For example, in the second example, the health administration method further includes step S124.

Step S124: generating a barcode of the second current device based on the identification code of the second current device.

For example, step S124 may be executed before step S121. For example, a device administrator may print a barcode (e.g., a two-dimensional code) of the second current device generated based on the identification code of the second current device and post the barcode of the second current device on the second current device. For example, after the barcode of the second current device has been posted to the second current device, there is no need to execute step S124.

For example, in the second example, the health administration method further includes step S125.

Step S125: using the object service module to acquire the identification code of the second current device by scanning the barcode of the second current device by a barcode scanner.

For example, an object (e.g., a patient currently seeking medical consultation) may use the object service module to acquire the identification code of the second current device by scanning the barcode of the second current device by the barcode scanner. For example, step S125 may be executed before step S121 and after step S124.

For example, in the second example, the health administration method further includes step S126.

Step S126: making the second current device allow the device-related data generated by the second current device to be transferred to the data receiver associated with the health administration apparatus via a Bluetooth gateway.

For example, step S126 may be executed before step S123 and after step S122.

For example, step S124, step S125, step S121, step S122, step S126, and step S123 are executed in sequence; in this case, firstly, the object (e.g., the patient currently seeking medical consultation) uses the object service module to acquire the identification code of the second current device by scanning the barcode of the second current device by the barcode scanner; and the object service module provides the acquired identification code of the second current device to the memory, and associates the identification code of the second current device with the first identification code of the current object; secondly, the first identification code of the current object and the identification code of the second current device associated with each other are acquired from the object service module, and a correspondence relationship between the identity information of the current object and the second current device is created; and then, the device-related data generated by the second current device is transferred to the data receiver associated with the health administration apparatus via the Bluetooth gateway.

It should be noted that, the device-related data generated by the second current device may also be transferred to the data receiver associated with the health administration apparatus via other applicable methods.

For example, for specific implementation modes or specific descriptions of the first identification code of the current object, the identification code of the second current device, the second current device, the memory associated with the health administration apparatus, and step S121 to step S126, the embodiment shown in FIG. 5 may be referred to, and no details will be repeated here.

In a third example, step S10 includes the following step S131 to step S133.

Step S131: providing unassociated data of at least one device of the plurality of devices, the unassociated data being configured to be displayed in a terminal, where a first individual service module is located, for an individual.

Step S132: receiving, from the first individual service module, a second identification code of the object corresponding to the unassociated data.

Step S133: associating the object corresponding to the unassociated data with the unassociated data, so as to generate a device usage record of the object corresponding to the unassociated data.

For example, step S131 to step S133 may be executed in an order of step S131, step S132, and step S133.

For example, step S133 includes the following step S1331 to step S1332.

Step S1331: using the second identification code of the object corresponding to the unassociated data to query the memory associated with the health administration apparatus, so as to acquire the identity information of the object corresponding to the unassociated data; and Step S1332: associating the identity information of the object corresponding to the unassociated data with the unassociated data.

For example, step S1331 and step S1332 may be executed in sequence.

For example, for specific implementation modes or specific descriptions of the unassociated data, the first individual service module, the individual, the second identification code of the object, the identity information of the object, and step S131 to step S133, the embodiment shown in FIG. 6 may be referred to, and no details will be repeated here.

In a fourth example, step S10 includes the following step S141 to step S142.

Step S141: receiving the identity information of the current object among the plurality of objects and device-related data generated by a third current device and associated with the identity information of the current object, the third current device being a device that has been used by the current object.

Step S142: generating the device usage record of the current object at least based on the identity information of the current object and the device-related data generated by the third current device and associated with the identity information of the current object.

For example, step S141 and step S142 may be executed in sequence.

For example, the receiving the identity information of the current object among the plurality of objects and the device-related data generated by the third current device and associated with the identity information of the current object includes: acquiring, from a second individual service module, the identity information of the current object among the plurality of objects and the device-related data associated with the identity information of the current object and generated by the third current device, which are associated with each other.

For example, in a fourth example, the health administration method further includes step S143 to step S145.

Step S143: making the third current device be configured to be associated with an object identity information data acquisition terminal; the object identity information data acquisition terminal having the second individual service module built in.

Step S144: using the object identity information data acquisition terminal to acquire the identity information of the current object among the plurality of objects and to provide the identity information of the current object to the second individual service module.

Step S145: using the second individual service module to acquire, based on an identification code of the third current device, the device-related data generated by the third current device and corresponding to the identity information of the current object, and associating the device-related data and the identity information of the current object with each other.

For example, step S143 to step 145 may be executed in an order of step S143, step S144, and step S145. For example, step S143 to step 145 may be executed before step S141 to step S142.

For example, in the fourth example, the health administration method further includes step S146.

Step S146: using the second individual service module to acquire basic information of the current object.

For example, step S146 may be executed after step S144 and before step S145.

For example, in at least one example of the health administration method, the basic information of the current object is selected from height, weight, and age of the current object.

For example, in the fourth example, the health administration method further includes step S147.

Step S147: using the second individual service module to acquire, based on the identity information of the current object, a query result provided by the health administration apparatus as to whether the current object exists in the memory; if the query result is that the current object exists in the memory, acquiring the basic information of the current object from the memory; if the query result is that the current object does not exist in the memory, acquiring the basic information of the current object; and providing the basic information and the identity information of the current object to the memory, to complete registration of the current object.

For example, step S147 may be executed after step S144 and before step S145.

For example, in the fourth example, the health administration method further includes step S148.

Step S148: using the second individual service module to provide at least a portion of the basic information of the current object to the third-party platform, and to acquire a predicted value of physical sign information of the current object from the third-party platform.

For example, step S148 may be executed after step S147 (or step S146) and before step S145.

For example, in the fourth example, the health administration method further includes step S149.

Step S149: using the second individual service module to acquire information of the individual and the identification code of the third current device, and to bind the individual to the third current device.

For example, step S149 may be executed before step S143.

For example, in the fourth example, the health administration method further includes step S1491.

Step S1491: using the second individual service module to associate the current object with the individual bound to the third current device, at least based on the identity information of the current object, and using the second individual service module to provide an association relationship between the current object and the individual bound to the third current device to the memory associated with the health administration apparatus.

For example, step S1491 may be executed after step S147 (or step S146) and before step S145.

For example, in the fourth example, the health administration method further includes step S1492.

Step S1492: using the second individual service module to generate, at least based on the device-related data generated by the third current device and associated with the identity information of the current object, a report of the current object.

For example, step S1492 may be executed after step S145.

For example, in at least one example of the health administration method, the object identity information data acquisition terminal includes a monitor and a printer; the monitor is configured to display the report of the current object that is generated at least based on the device-related data; and the printer is configured to print the report of the current object that is generated at least based on the device-related data.

For example, for specific implementation modes or specific descriptions of the identity information of the current object, the third current device, the device-related data associated with the identity information of the current object, the device usage record of the current object, the object identity information data acquisition terminal, the second individual service module, the identification code of the third current device, the basic information of the current object, the third-party platform, the identification code of the third current device, the individual bound to the third current device, the report of the current object, step S141 to step S149, step S1491 and step S1492, etc., the embodiment shown in FIG. 8 may be referred to, and no details will be repeated here.

In a fifth example, step S10 includes the following step S151 to step S153.

Step S151: acquiring the second identification code of the current object among the plurality of objects and an identification code of the fourth current device; the fourth current device being a device to be used by the current object.

Step S152: using the second identification code of the current object to query the memory associated with the health administration apparatus, so as to acquire the identity information of the current object, and to create a correspondence relationship between the identity information of the current object and the fourth current device.

Step S153: in a case where the data receiver associated with the health administration apparatus receives the device-related data originating from the fourth current device, associating the identity information of the current object with the device-related data, so as to generate a device usage record of the current object.

For example, step S151 to step S153 may be executed in an order of step S151, step S152, and step S153.

For example, in step S151, the acquiring the second identification code of the current object among the plurality of objects and the identification code of the fourth current device includes: acquiring, from the first individual service module of the terminal for the individual, the second identification code of the current object among the plurality of objects and the identification code of the fourth current device.

For example, in the fifth example, the health administration method further includes step S154 to step S155.

Step S154: allowing a monitor of a terminal where the first individual service module is located to display a list of currently unused devices.

Step S155: using the first individual service module to select at least one device among the currently unused devices as the fourth current device, acquire the second identification code of the current object, and associate the second identification code of the current object with the identification code of the fourth current device.

For example, step S154 to step S155 may be executed before step S151 to step S153. For example, step S154 to step S155 may be executed in sequence.

For example, for specific implementation modes or specific descriptions of the second identification code of the current object, the fourth current device, the identification code of the fourth current device, the memory associated with the health administration apparatus, the identity information of the current object, the data receiver associated with the health administration apparatus, the device-related data originating from the fourth current device, the first individual service module, the list of currently unused devices, the second identification code of the current object, and step S151 to step S155, etc., the embodiment shown in FIG. 13 may be referred to, and no details will be repeated here.

For example, in addition to step S10 and step S20, the health administration method further includes step S31.

Step S31: using the object service module to acquire, from the memory, a device usage record of the object associated with the object service module, and to provide the device usage record of the object associated with the object service module to a monitor of the terminal where the object service module is located.

For example, step S31 may be executed after step 20.

For example, in addition to step S10 and step S20, the health administration method further includes step S32 and step S33.

Step S32: generating a barcode of an individual based on the identification code of the individual.

Step S33: using the object service module to acquire the identification code of the individual by scanning the barcode of the individual by a barcode scanner, and to provide a first identification code of the object associated with the object service module and the identification code of the individual to the memory, for establishing an association relationship between the individual and the object associated with the object service module.

For example, step S32 and step S33 may be executed in sequence. For example, step S32 and step S33 may be executed before step S10; and for another example, step S32 and step S33 may be executed after step S20.

For example, in addition to step S10 and step S20, the health administration method further includes step S34.

Step S34: using the first individual service module for the individual, to acquire the identity information and the device usage record of the object associated with the individual, and to provide the identity information and the device usage record of the object associated with the individual to the monitor of the terminal where the first individual service module is located.

For example, step S34 may be executed after step 20.

For example, for specific implementation modes of step S31 to step S34, reference may be made to the related embodiments of the health administration apparatus, and no details will be repeated here.

For example, in addition to step S10 and step S20, the health administration method further includes step S40.

Step S40: grading a plurality of members belonging to an organization, and enabling a member of an $N^{th}$-level in the organization to have an authority to acquire data of a member of an $M^{th}$-level in the organization, N being a positive integer greater than 1, and M being a positive integer greater than or equal to 1 and less than N.

For example, in addition to step S10, step S20, and step S40, the health administration method further includes the following steps S50 to S70.

Step S50: receiving a statistical data viewing request sent by the member of the $N^{th}$-level;

Step S60: acquiring data of at least some members among members from a first-level to the $N^{th}$-level based on the statistical data viewing request;

Step S70: analyzing the data of the at least some members to acquire a statistical result, and outputting the statistical result.

For example, step S50 to step S70 may be executed after step S40. For example, step S50 to step S70 may be executed in an order of step S50, step S60, and step S70.

For example, the statistical result includes at least one item selected from a group consisting of: the total number of objects associated with the at least some members, the number of newly added objects associated with the at least some members, gender distribution of the objects associated with the at least some members, regional distribution of the objects associated with the at least some members, and level distribution of the objects associated with the at least some members.

For example, for specific implementation modes of step S40 to step S70, reference may be made to the example shown in FIG. 16, and no details will be repeated here.

Figure 57:
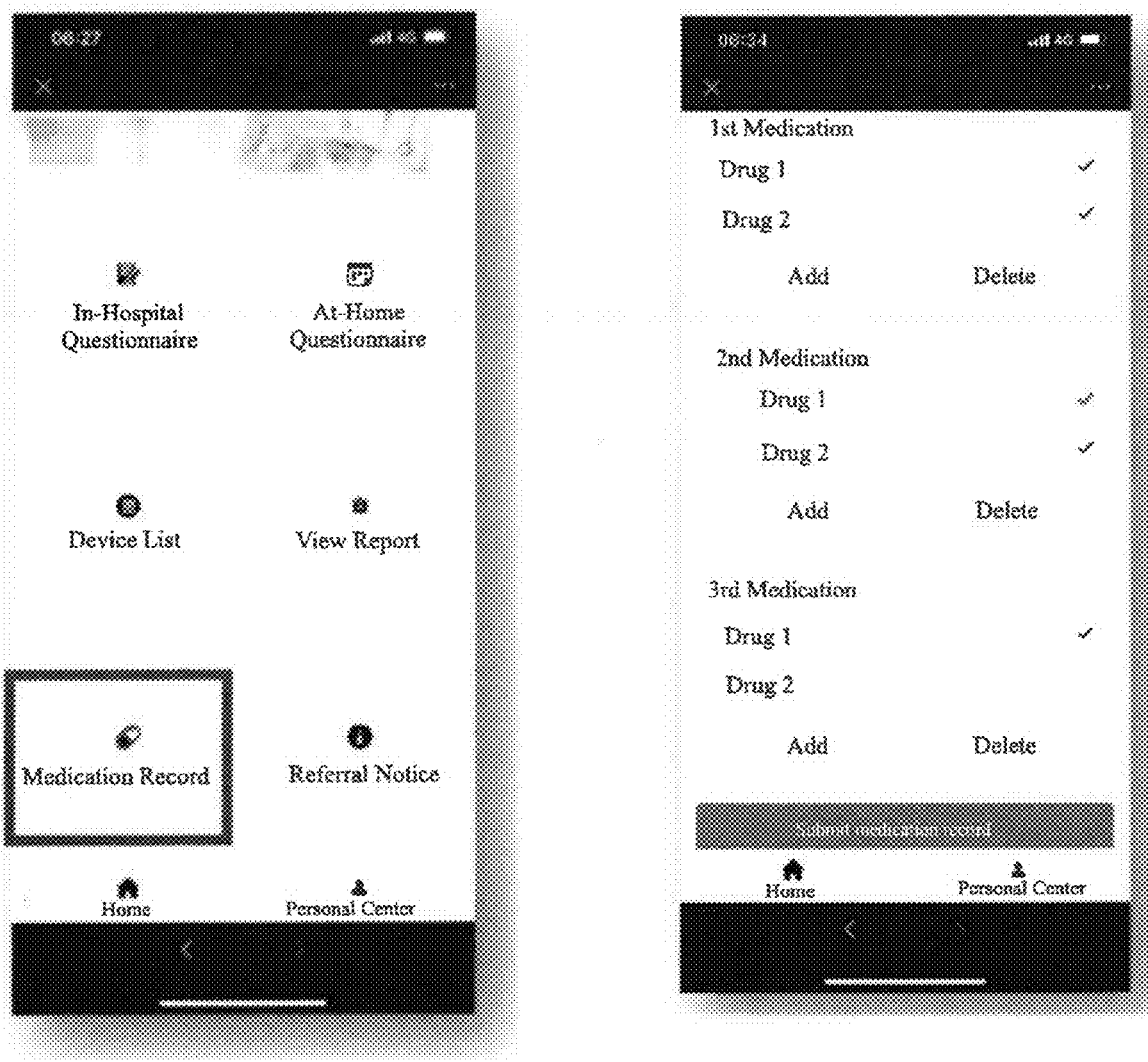
FIG. 57 shows another schematic diagram of an object service module provided by at least one embodiment of the present disclosure and a schematic diagram of a medication record input interface of the object service module.

For example, the object service module is configured to generate object medication record data according to a medication record filling operation. Exemplary description will be given below in conjunction with FIG. 57. FIG. 57 shows another schematic diagram (a left diagram of FIG. 57) of an object service module provided by at least one embodiment of the present disclosure and a schematic diagram (a right diagram of FIG. 57) of a medication record input interface of the object service module.

For example, after a medical worker provides a medication plan for the patient currently seeking medical consultation, the object (the patient currently seeking medical consultation) may click on "Medication Record" shown in the left diagram of FIG. 57 to enter the medication record input interface shown in the right diagram of FIG. 57 to fill in the medication record; and correspondingly, the object service module is configured to generate the object medication record data according to the medication record filling operation. For example, the object may fill in the medication record according to a predetermined period (e.g., every day), or may also fill in the medication record immediately after taking the medicine.

For example, the health administration method provided by at least one embodiment of the present disclosure further includes: receiving, from the object service module, the object medication record data generated according to the medication record filling operation, and providing the object medication record data to the memory associated with the health administration apparatus.

Figure 58:
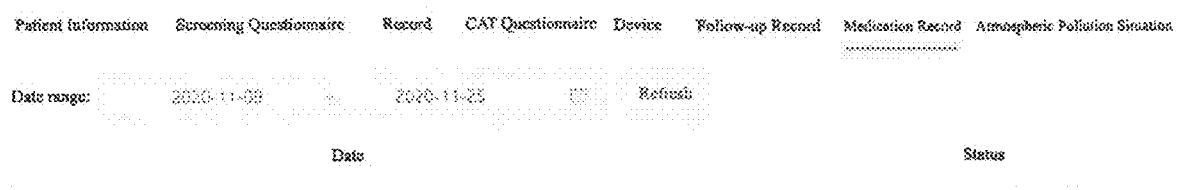
FIG. 58 is a schematic diagram of an object medication record in the object detail page of the first individual service module provided by at least one embodiment of the present disclosure.

For example, the health administration method provided by at least one embodiment of the present disclosure further includes: providing the object medication record data to the first individual service module. For example, the first individual service module is configured to display the object medication record. FIG. 58 is a schematic diagram of an object medication record in an object detail page of the first individual service module provided by at least one embodiment of the present disclosure. For example, an individual (a medical worker) associated with the object may view the object medication record of the object associated with the individual via the object detail page of the first individual service module. For example, when the object's illness condition has not improved for a long time, and is repeated or deteriorates, the individual (the medical worker) may check whether the object has followed the doctor's instructions to take medicine regularly and quantitatively, to prevent the individual from mistakenly thinking that the previously formulated medication plan is ineffective for the object and changing the medication plan. For example, the individual (the medical worker) may check, according to a predetermined period, whether the object follows the doctor's instructions and take medicine regularly and quantitatively, and remind the object to take medicine when the object does not comply with the doctor's instructions to take medicine regularly and quantitatively, so as to improve the object's compliance. For example, the individual (the medical worker) may check whether the object follows the doctor's instructions and takes medicine regularly and quantitatively before follow-up or before formulating a medication plan for a next period, so that follow-up or medication plan formulation is more targeted.

For example, the object service module is further configured to acquire atmospheric condition data, which is acquired via the object service module, of a geographic location (e.g., a city or a district of the city) where the object using the object service module is located. For example, the object service module is configured to acquire (e.g., via a terminal where the object service module is located) the geographic location of the object using the object service module, and acquire (e.g., acquire from the network) the atmospheric condition data of the geographic location where the object using the object service module is located. For example, the atmospheric condition data may be atmospheric pollution situation data. For example, the atmospheric condition data may include concentration of pollutants (e.g., sulfur dioxide) related to a target disease. For example, in a case where the object service module is implemented as a WeChat applet, the object service module may acquire authorization by the object for collecting the atmospheric condition data of the geographic location where the object is located through the WeChat, and collect (e.g., according to a predetermined period, for example, every day) the atmospheric condition data of the geographic location where the object is located under the authorization by the object.

For example, the health administration method provided by at least one embodiment of the present disclosure further includes: acquiring, from the object service module, the atmospheric condition data, which is acquired by the object service module, of the geographic location where the object using the object service module is located, and providing the atmospheric condition data to the memory associated with the health administration apparatus.

For example, the health administration method provided by at least one embodiment of the present disclosure further includes: providing the atmospheric condition data of the geographic location where the object using the object service module is located to the first individual service module. For example, the first individual service module is configured to display the atmospheric condition data of the geographic location where the object is located.

Figures 59, 60:
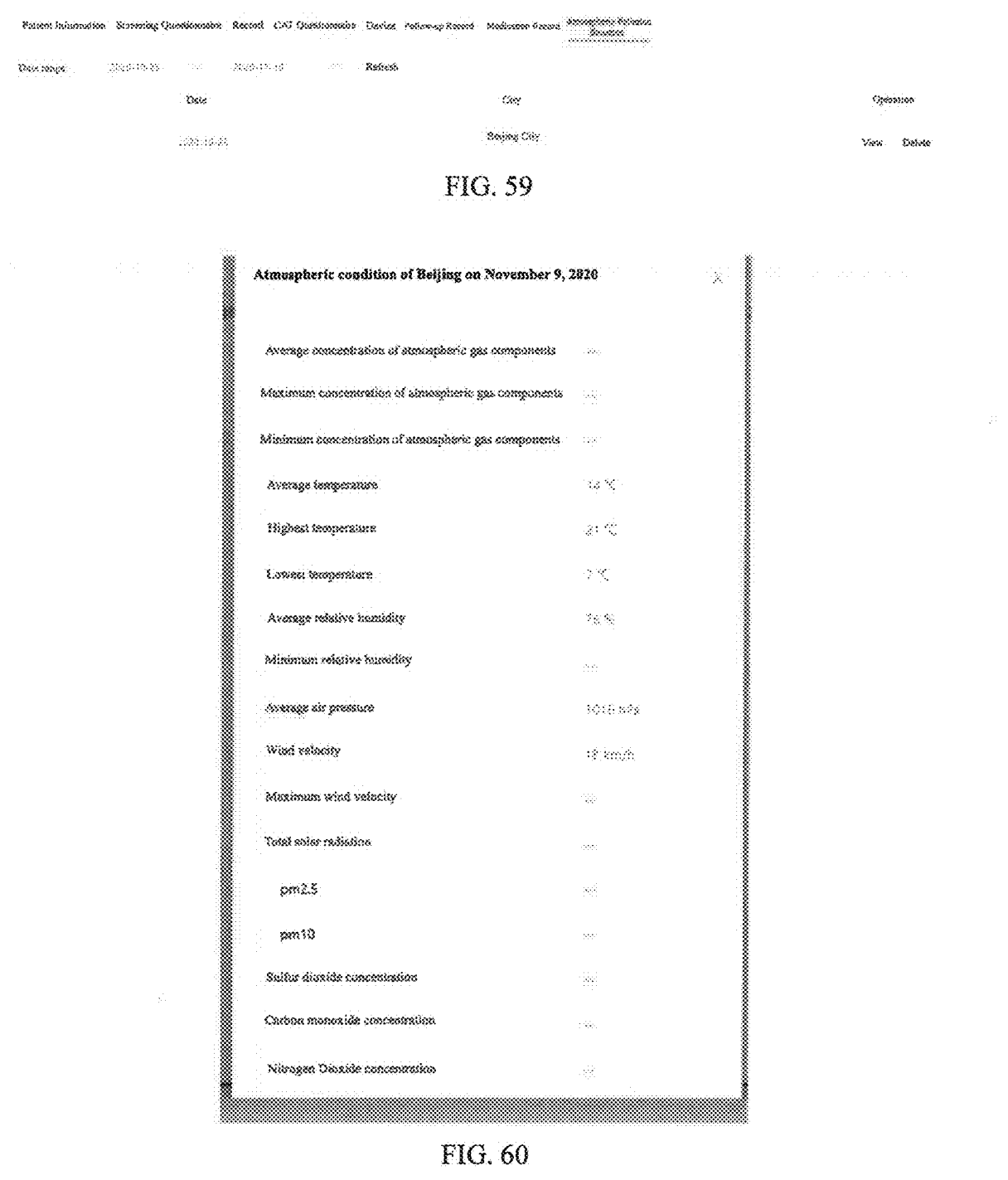

FIG. 59 is a schematic diagram of atmospheric condition (an atmospheric pollution condition) data in the object detail page of the first individual service module provided by at least one embodiment of the present disclosure; and FIG. 60 is a schematic diagram of an atmospheric condition (an atmospheric pollution condition) data display page provided by at least one embodiment of the present disclosure.

For example, an individual (a medical worker) associated with an object may view an atmospheric condition data list of a geographic location (e.g., Beijing) where the object associated with the individual is located via an object detail page of the first individual service module shown in FIG. 59. For example, the individual (the medical worker) associated with the object may click on "View" below "Operation" to enter the atmospheric condition (an atmospheric pollution condition) data display page shown in FIG. 60.

For example, when the object's illness condition has not improved for a long time, and is repeated or deteriorates, the individual (the medical worker) may view the atmospheric condition data of the geographic location where the object is located, analyze, in combination with the object's illness condition data, whether the atmospheric condition of the geographic location where the object is located has an adverse effect on the object's illness condition, advise the object to take corresponding countermeasures (e.g., insist on wearing protective appliances) when the atmospheric condition of the geographic location where the object is located is likely to have an adverse effect on the object's illness condition, and observe whether the object's illness condition is improved after taking the corresponding countermeasures.

For example, by making the object service module be further configured to acquire the atmospheric condition data of the geographic location where the object using the object service module is located, recommendation (e.g., health prescription) acquired by the object may be more targeted, dosage for the object may be reduced, and a rehabilitation period of the object is shortened.

For example, the first individual service module is configured to generate object visit situation data according to an object visit situation filling operation (or an entry operation). For example, an individual (a medical worker) associated with the object may visit the object, to acquire more information about the object (e.g., information that is not suitable for the object to fill in via a questionnaire).

For example, by making the first individual service module be configured to generate the object visit situation data according to the object visit situation filling operation, more detailed information about the object may be acquired, and thus more targeted health prescription may be specified for the object, which, thus, can improve compliance with the health prescription and shorten time required for treatment.

For example, a visit to an object (e.g., follow-up) may include an initial visit and subsequent visits. For example, the initial visit may be conducted after the object submits a questionnaire (e.g., a screening questionnaire) and before the object undergoes a physical examination. For example, information of the initial visit may be used by a doctor to determine at least one item selected from a group consisting of physical examination items that the object should participate in, determining at least one of illness condition and severity of the object (e.g., for grouping the objects), and formulating health prescriptions. For example, the subsequent visits may be conducted according to a predetermined period, for example, a subsequent visit is conducted every three months or so.

For example, according to a location where the object is located when the object is visited, visits to the object (e.g., follow-up) may include hospital follow-up and non-hospital follow-up. For example, the hospital follow-up refers to that: when the object is visited, the object is in a medical institution (e.g., a medical institution where the individual associated with the object is located). For example, the non-hospital follow-up refers to that: when the object is visited, the object is in any place (e.g., the object's home; via telephone, video, or other means of communication). For example, when the object needs to go to a medical institution to participate in physical examination items, the object may participate in the hospital follow-up; for example, when the object goes to the hospital for seeking medical consultation with respect to a target disease, the object may complete a baseline visit and related physical examination items, and in the 12th month after the baseline follow-up, the object may participate in the hospital follow-up and related physical examination items. For example, in the 3rd, 6th, and 9th months after the baseline follow-up, visits to the object by the individual may be completed, for example, at home.

FIG. 61 is a schematic diagram of a follow-up record page in the object detail page of the first individual service module provided by at least one embodiment of the present disclosure. FIG. 62 is a schematic diagram of a new follow-up content page of the first individual service module provided by at least one embodiment of the present disclosure.

For example, as shown in FIG. 61, the individual (the medical worker) associated with the object may click on a new follow-up record on a "follow-up record" page of the object detail page to enter the new follow-up content page shown in FIG. 62. For example, in the new follow-up content page shown in FIG. 62, the individual associated with the object may enter a follow-up date, a follow-up type (e.g., baseline follow-up or subsequent follow-up), and a follow-up content. For example, the doctor may determine the follow-up content based on the basic information of the user and the results of the questionnaire submitted by the user. For example, the follow-up content may include screening questionnaires, assessment forms, change forms, medical financial burden forms, anxiety and depression scales, and so on.

FIG. 63 is a schematic diagram of a portion of a chronic obstructive pulmonary disease screening questionnaire fill-in page provided by at least one embodiment of the present disclosure. For example, the individual associated with the object may acquire relevant information from the object based on questions shown on the page after entering the chronic obstructive pulmonary disease screening questionnaire fill-in page shown in FIG. 63, and fill out the questionnaire based on the relevant information acquired from the object. For example, the first individual service module is configured to generate object visit situation data based on an object visit situation filling operation (e.g., a questionnaire filling operation, an assessment form filling operation, and a change form filling operation).

Figures 64, 65, 66:
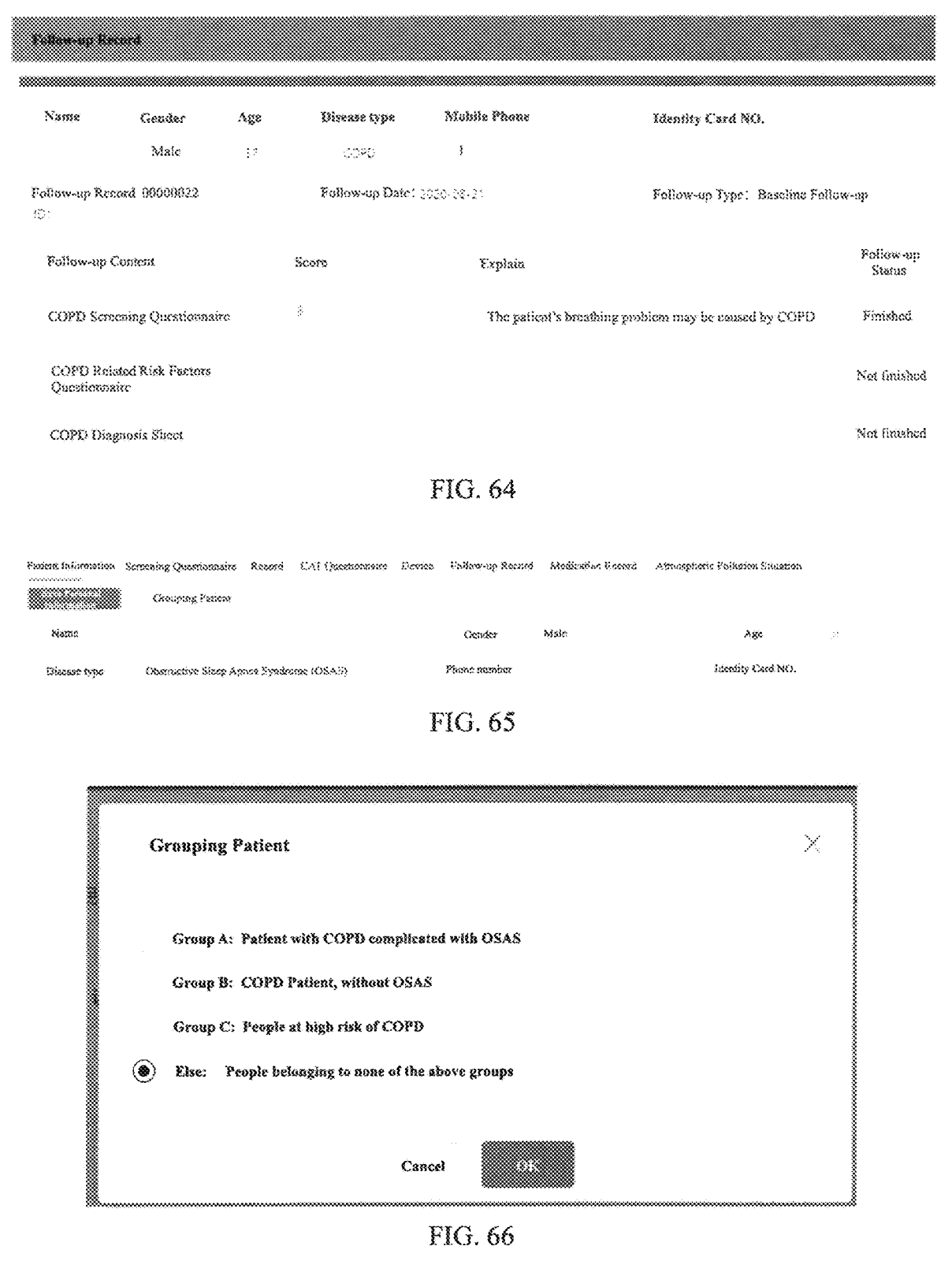

FIG. 64 is a schematic diagram of a follow-up content view page of the first individual service module provided by at least one embodiment of the present disclosure. For example, the individual associated with the object may view a completion situation of the follow-up content from the follow-up content view page shown in FIG. 64, and may click "View" (not shown) below "Operation" to view the completed follow-up content.

For example, the health administration method provided by at least one embodiment of the present disclosure further includes: acquiring, from the first individual service module, the object visit situation data generated according to the object visit situation filling operation, and providing the object visit situation to the memory associated with the health administration apparatus.

For example, by acquiring, from the first individual service module, the object visit situation data generated according to the object visit situation filling operation, and providing the object visit situation to the memory associated with the health administration apparatus, a plurality of medical workers may view the object visit situation data, thereby preventing the object from repeatedly participating in the follow-up during referral.

For example, the first individual service module is configured to assign an object to an object group matching the object according to an object grouping operation. Exemplary description will be given below in conjunction with FIG. 65 and FIG. 66.

FIG. 65 is a schematic diagram of the object detail page of the first individual service module provided by at least one embodiment of the present disclosure. FIG. 66 is a schematic diagram of a patient grouping page of the first individual service module provided by at least one embodiment of the present disclosure.

For example, one may click "Patient Information" on the object detail page of the first individual service module to enter the patient information page shown in FIG. 65; click "Group Patients" shown in FIG. 65 to enter a patient grouping page shown in FIG. 66; and then select an object group that matches the patient. For example, in a case where the object is determined to be a patient with chronic obstructive pulmonary disease (COPD) and with obstructive sleep apnea syndrome (OSAS), the object is assigned to a group A. For another example, when it is determined that the object is neither a COPD patient nor an OSAS patient, the object is not grouped (or the object is assigned to a patient group with non-target disease).

For example, by making the first individual service module be configured to assign an object to an object group matching the object according to an object grouping operation, applicable attention may be given to different groups of objects, so that efficiency and effect of object administration may be improved.

For example, the health administration method provided by at least one embodiment of the present disclosure further includes: acquiring, from the first individual service module, object grouping data generated according to an object grouping operation, and providing the object visit situation to the memory associated with the health administration apparatus.

For example, examples of application scenarios of the health administration apparatus and the health administration system will be described below. For example, the health administration apparatus may further include a first individual service module and a memory; and the health administration system includes a plurality of devices (e.g., a pulmonary function instrument, a respiratory screening instrument), a health administration apparatus, an object service module, a second individual service module, and an object identity information data acquisition terminal. It should be noted that, for sake of clarity, a patient and a doctor are used to represent an object and an individual, respectively, and a pulmonary function test and sleep screening are used as physical examination items for the object to participate in.

For example, the application scenarios of the health administration apparatus and the health administration system involve the following step S811 to step S830.

S811: filling in, by the patient, a screening questionnaire via the object service module. For example, the patient may click on "In-Hospital Questionnaire" shown in FIG. 2A or FIG. 57 to fill in the screening questionnaire. For example, the "In-Hospital Questionnaire" is a questionnaire filled out in the hospital.

S812: viewing, by the doctor, a questionnaire result via the first individual service module. For example, the doctor may click "View Details" shown in FIG. 3A to enter an object detail page shown in FIG. 3B, and click "Screening Questionnaire" in the object detail page shown in FIG. 3B to view the questionnaire result submitted by the patient and a questionnaire score (e.g., a score automatically acquired based on the questionnaire result).

S813: supplementing, by the doctor, patient information via the first individual service module. For example, the doctor may click "Patient Information" in the object detail page shown in FIG. 3B to enter a patient information page, and add the patient information (e.g., supplementary information other than simple information filled in during patient registration) on the patient information page.

S814: creating, by the doctor, a follow-up record via the first individual service module. For example, the doctor may click "New Follow-up Record" on the "follow-up record" page in the object detail page shown in FIG. 61 to create the follow-up record.

S815: filling in, by the doctor, follow-up forms one by one as needed via the first individual service module. For example, after clicking "New Follow-up Record", the doctor enters a new follow-up content page shown in FIG. 62, selects a content of this follow-up, and fills in the follow-up forms one by one.

S816: performing a pulmonary function test on the patient. For example, a portable pulmonary function instrument can be used to perform the pulmonary function screening on the patient; the pulmonary function instrument and the object identity information data acquisition terminal (e.g., a POS printer) are connected with each other via Bluetooth; and the second individual service module (e.g., the respiratory rehabilitation service APP) is used in (e.g., built in) the object identity information data acquisition terminal. For example, one may click "Pulmonary Function Screening" shown in FIG. 9A to enter an object information input interface of the second individual service module shown in FIG. 12A. And then patient identity is registered by scanning an identity card via the POS printer (or may also by typing in a mobile phone number), so as to enter an object information confirmation interface of the second individual service module; after clicking "OK", one may use following voice prompts of the pulmonary function instrument; and after use, click "End Screening" on a third current device usage page of the second individual service module shown in FIG. 12C to enter a report display and print page of the second individual service module shown in FIG. 12D. For example, one may click "Save" on the POS machine to save the report, or may also print the report (e.g., a thermal report).

S817: checking, by the doctor, a pulmonary function result of the patient. For example, a doctor may click "View Details" shown in FIG. 3A to enter the object detail page shown in FIG. 3B, and click "Record" shown in FIG. 3B to enter a record page shown in FIG. 3C and view an outpatient-service device, select a corresponding pulmonary function report, and click "View Details" to view the report.

S818: performing sleep screening on the patient. For example, the patient scans a two-dimensional code of a device (e.g., a pulse oximeter) to bind to the device; then takes the above-described device back to the residence for home sleep monitoring; takes the above-described device to the hospital a next day; and uploads data through a Bluetooth gateway. For example, for a detailed content of the record generated based on data output by the above-described device (e.g., the pulse oximeter), reference may be made to the example shown in FIG. 5, and no details will be repeated here. For example, the patient may click on "Device List" shown in FIG. 2A to enter the device list detail page to view the above-mentioned device taken away by scanning; and click "Unbind" on the device list detail page to be unbound with the above-described device after finishing using the device.

S819: checking, by the doctor, a sleep screening result via the first individual service module.

For example, the doctor may click "View Details" shown in FIG. 3A to enter the object detail page shown in FIG. 3B, and click "Record" shown in FIG. 3B to enter the record page shown in FIG. 3C and view the outpatient-service device, select a corresponding sleep screening report, and click "View Details" to view the report.

S820: grouping, by the doctor, patients via the first individual service module. For example, the doctor may comprehensively consider the pulmonary function report, the sleep screening report, the baseline follow-up result, the questionnaire result submitted by the patient, and the basic information of the patient to determine a group of the patient, and assign the patient to a matched object group on the patient grouping page shown in FIG. 66.

S821: binding the patient to a personal treating device. For example, the doctor may allocate a personal treating device (e.g., at least one selected from a group consisting of a ventilator and an oxygen generator) to the patient according to the patient's illness condition; the patient scans the above-described personal treating device to be bound with the above-described personal treating device, and then takes the above-described personal treating device back to the residence for use. For example, after the patient finishes using the personal treating device and turns off the personal treating device, data of using the personal treating device by the patient is provided to the above-described second record creation sub-module; the second record creation sub-module creates a device usage record based on the above-described data of using the personal treating device by the patient, and provides the above-described device usage record to the memory associated with the health administration apparatus. For example, for detailed contents of the record generated based on the data output by the above-described personal treating device (e.g., at least one selected from a group consisting of a ventilator and an oxygen generator), reference may be made to the example shown in FIG. 5, and no details will be repeated here.

S822: viewing home treatment report of the patient. For example, after the patient finishes using the personal treating device and turns off the personal treating device, the doctor may view the record of the patient using the personal treating device via the first individual service module, and the patient may view the record of the patient using the personal treating device via the object service module. For example, the user may click on "Device List" shown in FIG. 2A, to enter the device list detail page to view the above-described personal treating devices taken away by scanning, and may click on "Unbind" on the device list detail page to be unbound with the above-described personal treating device after finishing using the above-described personal treating device.

S823: filling in, by the patient, a CAT questionnaire. The patient clicks "At-Home Questionnaire" in FIG. 2A to enter an at-home questionnaire fill-in page, and fills in (fills in at home) questions involved in the at-home questionnaire (CAT questionnaire) and submits the at-home questionnaire.

S824: viewing, by the doctor, the CAT questionnaire via the first individual service module. For example, the doctor clicks "CAT Questionnaire" shown in FIG. 3B to view a filling situation of the CAT questionnaire of a certain patient on a certain day.

S825: filling in, by the patient, a medication record via the object service module. For example, the patient clicks "Medication Record" shown in FIG. 57 to enter a medication record input interface, types in the medication record, and submits the same.

S826: checking, by the doctor, the medication record via the first individual service module. For example, the doctor clicks "Medication Record" shown in FIG. 58 to view a medication record of a certain patient within a specified date range.

S827: checking, by the doctor, an atmospheric condition in a region where the patient is located via the first individual service module. For example, the doctor may click on "Atmospheric Pollution Situation" shown in FIG. 59 to view an atmospheric pollution situation of a geographic location where a certain patient is located within a specified date range.

S828: referring, by the doctor, the patient via the first individual service module. For example, the doctor may click "Initiate Referral" as shown in FIG. 50, and respectively input telephone numbers of the patient and a target doctor on pages shown in FIG. 51 and FIG. 52, to transfer the target patient to a corresponding target doctor (of either a superior hospital or a subordinate hospital).

S829: accepting, by a receiving doctor (a doctor who receives the referred patient, the above-described target doctor, and a referred doctor as described later), referral via the first individual service module. For example, after the receiving doctor accepts the referral via a page shown in FIG. 53, the referral succeeds. For example, a referring doctor shares patient information with a referred doctor.

S830: receiving, by the patient, a referral notice via the object service module. For example, the patient may receive the referral notice pushed by WeChat on his/her mobile terminal.

Figure 55:
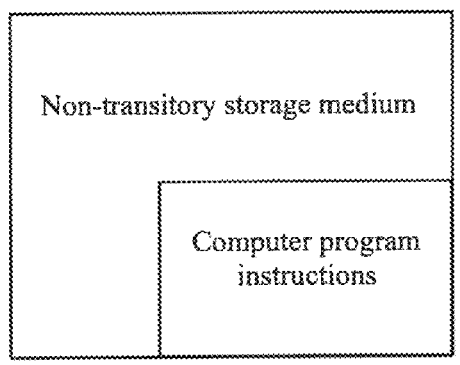
FIG. 55 shows an exemplary block diagram of a non-transitory storage medium provided by at least one embodiment of the present disclosure.

At least one embodiment of the present disclosure further provides a non-transitory storage medium. FIG. 55 shows an exemplary block diagram of a non-transitory storage medium provided by at least one embodiment of the present disclosure. For example, as shown in FIG. 55, the non-transitory storage medium stores computer program instructions, when the computer program instructions are executed by a processor, the computer program instructions cause a computer to execute a method, including: generating a device usage record of at least one object based at least on identity information of the at least one object among the plurality of objects and data generated by a device used by the at least one object, and providing the device usage record of the at least one object to a memory associated with the health administration apparatus.

For example, for specific implementation modes or related descriptions of the generating a device usage record of at least one object based at least on identity information of the at least one object among the plurality of objects and data generated by a device used by the at least one object, and providing the device usage record of the at least one object to a memory associated with the health administration apparatus, the health administration method provided by at least one embodiment of the present disclosure may be referred to, and no details will be repeated here.

Figure 56:
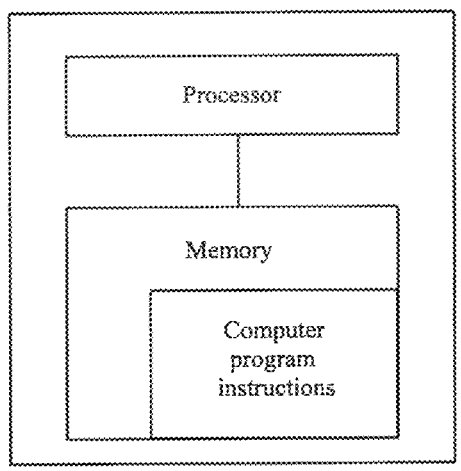
FIG. 56 shows an exemplary block diagram of a health administration apparatus provided by at least one embodiment of the present disclosure.

At least one embodiment of the present disclosure further provides a health administration apparatus. FIG. 56 shows an exemplary block diagram of a health administration apparatus provided by at least one embodiment of the present disclosure. For example, as shown in FIG. 56, the health administration apparatus includes a processor (e.g., a processor including hardware) and a memory. The memory stores computer program instructions suitable for execution by the processor; and when the computer program instructions executed by the processor, the computer program instructions cause the processor to execute a method, including: generating a device usage record of at least one object based at least on identity information of the at least one object among the plurality of objects and data generated by a device used by the at least one object, and providing the device usage record of the at least one object to a memory associated with the health administration apparatus.

For example, for specific implementation modes or related descriptions of the generating a device usage record of at least one object based at least on identity information of the at least one object among the plurality of objects and data generated by a device used by the at least one object, and providing the device usage record of the at least one object to a memory associated with the health administration apparatus, the health administration method provided by at least one embodiment of the present disclosure may be referred to, and no details will be repeated here.

For example, the processor is, for example, a central processing unit (CPU) or other forms of processing units with a data processing capability and/or an instruction execution capability; for example, the processor may be implemented as a general-purpose processor, and also a single-chip microcomputer, a micro-processor, a digital signal processor, a dedicated image processing chip, or a field programmable gate array, and the like. The memory may include, for example, a volatile memory and/or a non-volatile memory, and may include, for example, a Read-Only Memory (ROM), a hard disk, a flash memory, and the like. Correspondingly, the memory may be implemented as one or more computer program products, and the computer program products may include various forms of computer-readable storage media; and one or more computer program instructions may be stored on the computer-readable storage media. The processor may run the program instructions, to implement desired functions. The memory may also store various other application programs and various data, as well as various data used and/or generated by the application programs.

Although the present disclosure has been described in detail with general description and specific implementations, it is obvious to those skilled in the art that some modifications or improvements may be made on the basis of the embodiments of the present disclosure. Therefore, these modifications and improvements made without departing from the spirit of the present disclosure all fall within the protection scope of the present disclosure.

What have been described above are only exemplary implementations of the present disclosure, and not intended to limit the scope of protection of the present disclosure, and the scope of protection of the present disclosure is determined by the appended claims.

The invention claimed is:

1. A health administration method, for managing a plurality of objects and a plurality of devices, the method comprising:
   automatically generating a device usage record, of a device that is used by at least one object among the plurality of devices, of the at least one object based at least on identity information of the at least one object among the plurality of objects and data generated by the device that is used by the at least one object, and providing the device usage record of the at least one object to a memory associated with a health administration apparatus;
   wherein the automatically generating the device usage record, of the device that is used by the at least one object among the plurality of devices, of the at least one object based at least on the identity information of the at least one object among the plurality of objects and the data generated by the device that is used by the at least one object, comprises:
   acquiring a first identification code of a first current object among the plurality of objects and an identification code of a first current device, wherein the first current device is a device that has been used by the first current object;
   using the identification code of the first current device to automatically query the memory associated with the health administration apparatus, to acquire latest device-related data originating from the first current device and transferred to the memory;
   converting in real time a data exchange format of the latest device-related data, acquired from the automatic query, into a target data exchange format corresponding to a type of data format of the first current device according to the type of the first current device, so as to obtain latest device-related data after format conversion;
   using the first identification code of the first current object to automatically query the memory, to acquire identity information of the first current object; and
   automatically associating the identity information of the first current object with the latest device-related data after format conversion to automatically generate a device usage record of the first current object;
   wherein the health administration method further comprises:
   acquiring, from an object service module, atmospheric condition data, which is acquired by the object service module, of a geographic location where an object using the object service module is located, and providing the atmospheric condition data to the memory associated with the health administration apparatus;
   wherein the object service module is implemented by at least one selected from a group consisting of a network end, a mobile end, and a desktop end.

2. The health administration method according to claim 1, wherein the acquiring the first identification code of the first current object among the plurality of objects and the identification code of the first current device comprises: acquiring the first identification code of the first current object and the identification code of the first current device from the object service module of a terminal for the first current object.

3. The health administration method according to claim 1, further comprising:
   making the first current device allow device-related data generated by the first current device to be transferred to the memory via a third-party platform.

4. The health administration method according to claim 1, wherein the automatically generating the device usage record, of the device that is used by the at least one object among the plurality of devices, of the at least one object based at least on the identity information of the at least one object among the plurality of objects and the data generated by the device that is used by the at least one object, comprises:
   acquiring a first identification code of a second current object among the plurality of objects and an identification code of a second current device, wherein the second current device is a device to be used by the second current object;
   using the first identification code of the second current object to automatically query the memory associated with the health administration apparatus, to acquire identity information of the second current object and to create a correspondence relationship between the identity information of the second current object and the second current device; and
   in a case where a data receiver associated with the health administration apparatus receives device-related data originating from the second current device, automatically associating the identity information of the second current object with the device-related data to generate a device usage record of the second current object.

5. The health administration method according to claim 1, wherein the automatically generating the device usage record, of the device that is used by the at least one object among the plurality of devices, of the at least one object based at least on the identity information of the at least one object among the plurality of objects and the data generated by the device that is used by the at least one object, comprises:
   providing unassociated data of at least one device of the plurality of devices, wherein the unassociated data is configured to be displayed in a terminal, where a first individual service module is located, for an individual;
   receiving, from the first individual service module, a second identification code of an object corresponding to the unassociated data; and
   associating the object corresponding to the unassociated data with the unassociated data, to generate a device usage record of the object corresponding to the unassociated data;
   wherein the first individual service module is implemented by at least one selected from a group consisting of a network end, a mobile end, and a desktop end.

6. The health administration method according to claim 1, wherein the automatically generating the device usage record, of the device that is used by the at least one object among the plurality of devices, of the at least one object based at least on the identity information of the at least one object among the plurality of objects and the data generated by the device that is used by the at least one object, comprises:
   receiving identity information of a third current object among the plurality of objects and device-related data generated by a third current device and associated with the identity information of the third current object, wherein the third current device is a device that has been used by the third current object; and
   generating a device usage record of the third current object based at least on the identity information of the third current object and the device-related data generated by the third current device and associated with the identity information of the third current object.

7. The health administration method according to claim 6, further comprising:
   making the third current device be configured to be associated with an object identity information data acquisition terminal, wherein the object identity information data acquisition terminal has a second individual service module built in;
   using the object identity information data acquisition terminal to acquire the identity information of the third current object among the plurality of objects and to provide the identity information of the third current object to the second individual service module; and
   using the second individual service module to acquire, based on an identification code of the third current device, the device-related data generated by the third current device and corresponding to the identity information of the third current object, and associating the device-related data with the identity information of the third current object;
   wherein the second individual service module is implemented by at least one selected from a group consisting of a network end, a mobile end, and a desktop end.

8. The health administration method according to claim 6, further comprising: using a second individual service module to acquire basic information of the third current object and to acquire, based on the identity information of the third current object, a query result provided by the health administration apparatus as to whether the third current object exists in the memory;
   if the query result is that the third current object exists in the memory, acquiring the basic information of the third current object from the memory;
   if the query result is that the third current object does not exist in the memory, acquiring the basic information of the third current object, and providing the basic information and the identity information of the third current object to the memory, to complete registration of the third current object;
   wherein the second individual service module is implemented by at least one selected from a group consisting of a network end, a mobile end, and a desktop end.

9. The health administration method according to claim 6, further comprising: using a second individual service module to associate, at least based on the identity information of the third current object, the third current object with an individual bound to the third current device, and
   using the second individual service module to provide an association relationship between the third current object and the individual bound to the third current device to the memory associated with the health administration apparatus;
   wherein the second individual service module is implemented by at least one selected from a group consisting of a network end, a mobile end, and a desktop end.

10. The health administration method according to claim 7, further comprising: using the second individual service module to generate, at least based on the device-related data generated by the third current device and associated with the identity information of the third current object, a report of the third current object.

11. The health administration method according to claim 10, wherein the object identity information data acquisition terminal comprises a monitor and a printer;
the monitor is configured to display the report of the third current object that is generated at least based on the device-related data; and
the printer is configured to print the report of the third current object that is generated at least based on the device-related data.

12. The health administration method according to claim 1, wherein the automatically generating the device usage record, of the device that is used by the at least one object among the plurality of devices, of the at least one object based at least on the identity information of the at least one object among the plurality of objects and the data generated by the device that is used by the at least one object, comprises:
acquiring a second identification code of the first current object among the plurality of objects and an identification code of a fourth current device, wherein the fourth current device is a device to be used by the first current object;
using the second identification code of the first current object to automatically query the memory associated with the health administration apparatus, to acquire the identity information of the first current object and to create a correspondence relationship between the identity information of the first current object and the fourth current device; and
in a case where a data receiver associated with the health administration apparatus receives device-related data originating from the fourth current device, automatically associating the identity information of the first current object with the device-related data to generate a device usage record of the first current object.

13. The health administration method according to claim 1, further comprising: receiving, from the object service module, object medication record data generated according to a medication record filling operation, and providing the object medication record data to the memory associated with the health administration apparatus.

14. The health administration method according to claim 1, further comprising: generating a barcode of an individual based on an identification code of the individual.

15. The health administration method according to claim 14, further comprising:
using a first individual service module for the individual to acquire identity information and a device usage record of an object associated with the individual, and to provide the identity information and the device usage record of the object associated with the individual to a monitor of a terminal where the first individual service module is located;
using the object service module to acquire the identification code of the individual by scanning the barcode of the individual through a barcode scanner, and to provide a first identification code of an object associated with the object service module and the identification code of the individual to the memory, for establishing an association relationship between the individual and the object associated with the object service module;
wherein the first individual service module is implemented by at least one selected from a group consisting of a network end, a mobile end, and a desktop end.

16. The health administration method according to claim 1, further comprising:
grading a plurality of members belonging to an organization, and enabling a member of an $N^{th}$-level in the organization to have an authority to acquire data of a member of an $M^{th}$-level in the organization,
N being a positive integer greater than 1, and M being a positive integer greater than or equal to 1 and less than N.

17. The health administration method according to claim 16, further comprising:
receiving a statistical data viewing request sent by the member of the $N^{th}$-level;
acquiring data of at least some members among members from a first-level to the $N^{th}$-level based on the statistical data viewing request;
analyzing the data of the at least some members to acquire a statistical result, and outputting the statistical result.

18. A health administration apparatus, comprising: a processor and a memory, wherein the memory stores computer program instructions suitable for being executed by the processor; and when executed by the processor, the computer program instructions cause the processor to execute a following method, comprising:
automatically generating a device usage record, of a device that is used by at least one object among the plurality of devices, of the at least one object based at least on identity information of the at least one object among the plurality of objects and data generated by the device that is used by the at least one object, and providing the device usage record of the at least one object to a memory associated with the health administration apparatus;
wherein the automatically generating the device usage record, of the device that is used by the at least one object among the plurality of devices, of the at least one object based at least on the identity information of the at least one object among the plurality of objects and the data generated by the device that is used by the at least one object, comprises:
acquiring a first identification code of a first current object among the plurality of objects and an identification code of a first current device, wherein the first current device is a device that has been used by the first current object;
using the identification code of the first current device to automatically query the memory associated with the health administration apparatus, to acquire latest device-related data originating from the first current device and transferred to the memory;
converting in real time a data exchange format of the latest device-related data, acquired from the automatic query, into a target data exchange format corresponding to a type of data format of the first current device according to the type of the first current device, so as to obtain latest device-related data after format conversion;
using the first identification code of the first current object to automatically query the memory, to acquire identity information of the first current object; and
automatically associating the identity information of the first current object with the latest device-related data after format conversion to automatically generate a device usage record of the first current object;
wherein the method further comprises:
acquiring, from an object service module, atmospheric condition data, which is acquired by the object service module, of a geographic location where an object using the object service module is located, and providing the atmospheric condition data to the memory associated with the health administration apparatus;

wherein the object service module is implemented by at least one selected from a group consisting of a network end, a mobile end, and a desktop end.

19. A health administration system, comprising a health administration apparatus and a plurality of devices;

wherein the health administration apparatus comprises: a processor and a memory, the memory stores computer program instructions suitable for being executed by the processor; and when executed by the processor, the computer program instructions cause the processor to execute a following method, comprising:

automatically generating a device usage record, of a device that is used by at least one object among the plurality of devices, of the at least one object based at least on identity information of the at least one object among the plurality of objects and data generated by the device that is used by the at least one object, and providing the device usage record of the at least one object to a memory associated with the health administration apparatus;

wherein the automatically generating the device usage record, of the device that is used by the at least one object among the plurality of devices, of the at least one object based at least on the identity information of the at least one object among the plurality of objects and the data generated by the device that is used by the at least one object, comprises:

acquiring a first identification code of a first current object among the plurality of objects and an identification code of a first current device, wherein the first current device is a device that has been used by the first current object;

using the identification code of the first current device to automatically query the memory associated with the health administration apparatus, to acquire latest device-related data originating from the first current device and transferred to the memory;

converting in real time a data exchange format of the latest device-related data, acquired from the automatic query, into a target data exchange format corresponding to a type of data format of the first current device according to the type of the first current device, so as to obtain latest device-related data after format conversion;

using the first identification code of the first current object to automatically query the memory, to acquire identity information of the first current object; and automatically associating the identity information of the first current object with the latest device-related data after format conversion to automatically generate a device usage record of the first current object;

wherein the method further comprises:

acquiring, from an object service module, atmospheric condition data, which is acquired by the object service module, of a geographic location where an object using the object service module is located, and providing the atmospheric condition data to the memory associated with the health administration apparatus;

wherein the object service module is implemented by at least one selected from a group consisting of a network end, a mobile end, and a desktop end.

* * * * *